US010577590B2

(12) United States Patent
Shin et al.

(10) Patent No.: US 10,577,590 B2
(45) Date of Patent: Mar. 3, 2020

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/303,504

(22) PCT Filed: Mar. 13, 2015

(86) PCT No.: PCT/KR2015/002470

§ 371 (c)(1),
(2) Date: Oct. 21, 2016

(87) PCT Pub. No.: WO2015/156509

PCT Pub. Date: Oct. 15, 2015

(65) Prior Publication Data

US 2017/0037380 A1 Feb. 9, 2017

(30) Foreign Application Priority Data

Apr. 10, 2014 (KR) ........................ 10-2014-0042911

(51) Int. Cl.

| | |
|---|---|
| ***C12N 7/00*** | (2006.01) |
| ***A23K 20/153*** | (2016.01) |
| ***A23K 20/147*** | (2016.01) |
| ***A23K 20/10*** | (2016.01) |
| ***A01N 63/00*** | (2020.01) |
| ***A23L 2/52*** | (2006.01) |
| ***A61K 35/76*** | (2015.01) |
| ***C11D 3/48*** | (2006.01) |

(52) U.S. Cl.

CPC ............... *C12N 7/00* (2013.01); *A01N 63/00* (2013.01); *A23K 20/10* (2016.05); *A23K 20/147* (2016.05); *A23K 20/153* (2016.05); *A23L 2/52* (2013.01); *A61K 35/76* (2013.01); *C11D 3/48* (2013.01); *A23V 2002/00* (2013.01); *C12N 2795/10121* (2013.01); *C12N 2795/10131* (2013.01); *C12N 2795/10132* (2013.01)

(58) Field of Classification Search

None

See application file for complete search history.

(56) References Cited

U.S. PATENT DOCUMENTS

| | | | | |
|---|---|---|---|---|
| 7,211,426 | B2 * | 5/2007 | Bruessow | A61K 35/76 435/235.1 |
| 8,021,657 | B2 | 9/2011 | Bruessow et al. | |

FOREIGN PATENT DOCUMENTS

| | | | |
|---|---|---|---|
| CN | 101724607 | A | 6/2010 |
| KR | 10-2011-0041670 | A | 4/2011 |
| KR | 10-1101376 | B1 | 1/2012 |
| KR | 10-1260645 | B1 | 5/2013 |
| KR | 10-1381793 | B1 | 4/2014 |
| KR | 10-1381795 | B1 | 4/2014 |
| KR | 10-1381797 | B1 | 4/2014 |
| KR | 10-1381798 | B1 | 4/2014 |
| WO | 2013/073843 | A1 | 5/2013 |
| WO | 2013/157813 | A1 | 10/2013 |

OTHER PUBLICATIONS

Bihannic et al., Vet. Res., 45(76):1-12 (2014).*
Nguyen et al, J. Vet. Sci., 12(2):159-164 (2011).*
Nagy et al., Vet. Res., 30:259-284 (1999).*
Zhang, Zootaxa 3148:1-237 (2011).*
Cha et al., "Effect of Bacteriophage in Enterotoxigenic *Escherichia coli* (ETEC) Infected Pigs", 2012, Journal of Veterinary Medical Science, vol. 74, Issue 8, pp. 1037-1039.
Dini et al., "Isolation and Selection of Coliphages as Potential Biocontrol Agents of Enterohemorrhagic and Shiga Toxin-producing *E. coli* (EHEC and STEC) in Cattle", Journal of Applied Microbiology, 2010, vol. 109, Issue 3, pp. 873-887.
Jamalludden et al., "Isolation and Characterization of Nine Bacteriophages that lyse O149 Enterotoxigenic *Escherichia coli*," Veterinary Microbiology, 2007, vol. 124, pp. 47-57.
NCBI, GenBank Accession No. HQ829472.1, Sep. 7, 2011.
International Search Report dated Jun. 18, 2015 of PCT/KR2015/002470 which is the parent application and its English translation—4 pages.
Extended European Search Report dated Nov. 10, 2017 in corresponding European Patent Application No. 15776278.2—9 pages.
Endersen et al., "Phage Therapy in the Food Industry", Annual Review of Food Science and Technology, Jan. 9, 2014, vol. 5, No. 1, pp. 327-349.
Kim et al., "Evaluation of bacteriophages for prevention and treatment of diarrhea due to experimental enterotoxigenic *Escherichia coli* K88 infection of weaned piglets", Korean J. Vet. Serv., 2011, vol. 34, Issue 4, pp. 341-352.
Bourdin et al., "Coverage of diarrhoea-associated *Escherichia coli* isolates from different origins with two types of phage cocktails", Microbial Biotechnology, 2014, vol. 7, No. 2, pp. 165-176.
Jamalludeen et al., "Evaluation of bacteriophages for prevention and treatment of diarrhea due to experimental enterotoxigenic *Escherichia coli* O149 infection of pigs", Veterinary Microbiology, 2009, vol. 136, pp. 135-141.
Yan et al., "Effect of Bacteriophage Supplementation on the Growth Performance, Nutrient Digestibility, Blood Characteristics, and Fecal Microbial Shedding in Growing Pigs", Asian-Aust. J. Anim. Sci., Oct. 2012, vol. 25, No. 10, pp. 1451-1456.

(Continued)

*Primary Examiner* — Thomas J. Visone
(74) *Attorney, Agent, or Firm* — Knobbe Martens Olson & Bear LLP

(57) ABSTRACT

The present invention relates to a novel bacteriophage ΦCJ28 (KCCM11466P) and a composition containing the same as an active ingredient. Further, the present invention relates to a method for preventing and/or treating infective diseases caused by enterotoxic *Escherichia coli* (ETEC) of animals excluding humans by using the composition.

2 Claims, 3 Drawing Sheets

Specification includes a Sequence Listing.

(56) References Cited

OTHER PUBLICATIONS

Brussow, "Phage therapy: the *Escherichia coil* experience", Microbiology, 2005, vol. 151, pp. 2133-2140.
Loc-Carrillo et al., "Pros and cons of phage therapy", Bacteriophage, Mar./Apr. 2011, vol. 1, No. 2, pp. 111-114.

* cited by examiner

【Fig. 1】
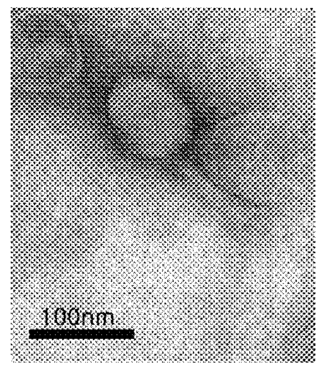
【Fig. 2】
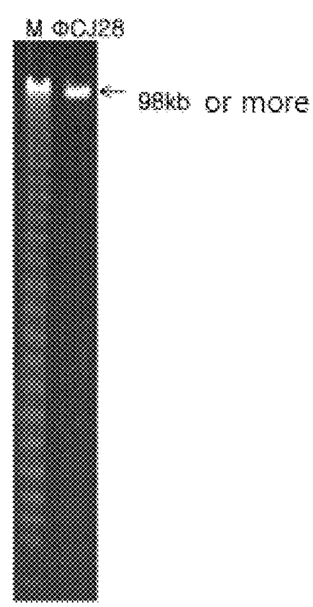

【Fig. 3】
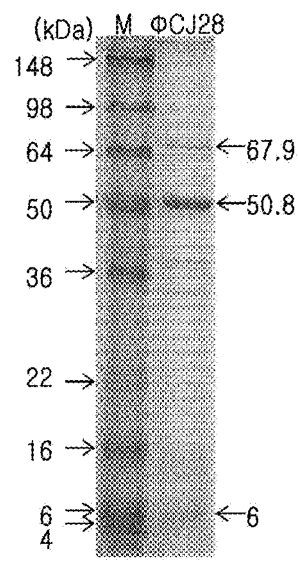
【Fig. 4】
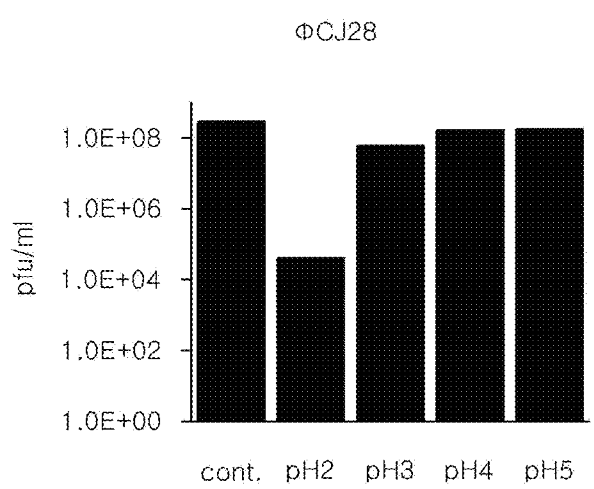

【Fig. 5】
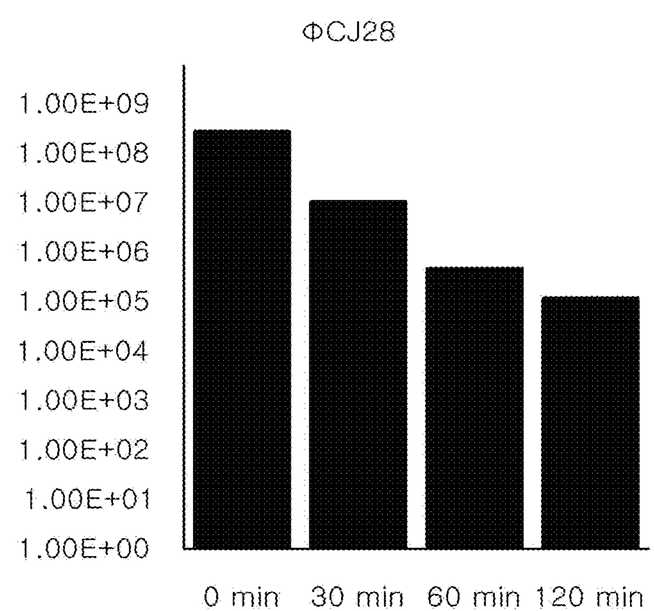

SEQUENCE LISTING

<160> NUMBER OF SEQ ID NOS: 1

<210> SEQ ID NO 1
<211> LENGTH: 171499
<212> TYPE: DNA
<213> ORGANISM: Artificial Sequence
<220> FEATURE:
<223> OTHER INFORMATION: Novel Bacteriophage CJ28

<400> SEQUENCE: 1
aaatacgttg ggtccaaccc attgaatatg caaccattat atcactcatt tcaataagcg 60
ttttggctgc ttcaaaagtc attacattag aggtttccgc tgtttgggtg aatttaccgt 120
ccatggagtg gatataatgg tcataatgaa tctgggtatc ttgctcgttt aaatcaaact 180
tgacaaagca acgtttttcc tcggacaatc cacgaacacg gttagtaata gtatcccaat 240
attcatcgat gtaaatacct tcaagagaaa aagcttcatg ctcgttaaga ttagacttga 300
caatttcaat aatatctgaa ggcttaagac ctgattcaag aagctcttgg attttagcca 360
atttctcagc attgccttga gggtccattt tatcaaattt tttagcttct tcaaaatgtt 420
gctcagggcg agcactcaca cctttaccaa agtagaaagg ttttttgttt tcatctacta 480
aacgatatac ctgataaatt gtttcttgat tgtaagccat tttaaatctc ctttagttga 540
taggtctata gtatcatgcc tacaggagat gtaaactgat tttataaata ttaatttaac 600
aggaggataa catgggcagt attttttacc aaatctggaa attggccgaa aagaaagaca 660
agaaaatgat gttaggtttt cttgcactag atgtattcct ttggaatctt ctggtagtcc 720

```
ctgtagccgc tagtcaaggt gtaattttac cagcggttac aatggagcac gtgttaagca    780
tagttgggtt ctttagcgga attcctgcct aaatcttgga atattttgaa agtctcattt    840
ttgccattaa accttgggct atattagctt tcatatatgc cagtacatca tttatatcgg    900
ctttatcttt cataaccata tcatttatat ctttagaagg ccatggggcc ttgtcccaga    960
atagaaccct ttcgccagca tcaactaatc gttgcatacg cttaattgtg tcaggatggc   1020
ggggttcatt gtccattacc caggcacgag tttctttaca tggaactata gccaagtcca   1080
atgacccacc agtaattgct attgcattcg gtacgaataa tgaatcgata ggaccttcca   1140
ttacccacac caactgacgt tcgtcaactg tatccattcc atatattttt gtagcttggt   1200
catgagcttt tattgtaata tatttttgtg gagcgtcttt acgtaaggct cgaccctgaa   1260
aactttcaat ttgtttattc ttattgaaaa ttggaataac caaacgaggc tcaggcattt   1320
ctttagaata ggtccctgga ttgacagagt tcaccaatgc aggccattct ttagtaaacc   1380
acagccggtt ccatttgttt tcaggaatgc aacgtaacgt cacatatttt ataataggat   1440
ggtccttcgg cattctatct aatcgttcac agaaattaag cttttcgatg acaggcatct   1500
tagctttaat tttttcagat atctccacct taggtgcagc ttgtctcccg aacgattgct   1560
ctttatgttt ctcaagaata tattcacgat ataaatcagg ctcatattcg tatagatact   1620
tcttaattcc tgctgaataa tcacagttaa aacagtgcag cataatagag ccgtcattgg   1680
caggataggc ccaaaaacga gctttgttct catctttttg ggagtcaccg catacacgac   1740
aacggcagtt taatttaaaa tcactaccag ttacttgtct gaatttaggt tggtaattca   1800
aggcacgtac agcaaattct ttatcgacat atgacattat ttttccttgg gccctaaatt   1860
aatagagcca ttatatcatt cgttttcgga tttttcttta cgctttttag atgggatttg   1920
ttcaggccct ttgttgacga ccgcgcctga ggtagttccg gaggcaatag cagtaggatt   1980
accacctgca tcgcctgcga ccatatcttc gttcataact tctttaaaag atttcatagg   2040
ctcctggcct tatttatatt acgaaaatag ctttatcacc atttgcatca gtgacttcat   2100
aggtatcttc gtggtaaagt ggaataatcc aagtcgcacc atcaccagca ataatatgga   2160
tagcttcttg gtcttttgat acgatttcat attcttcgaa taattcgaat acagaaatct   2220
tagagcccgt acacattgca ctcatattgt tcccttcttt taatcagttg gcgatgagcc   2280
tttttaagtt tacgaagctg acgtttagtt ggccgtgcaa cataagcttg agtagttact   2340
cgtccaaaaa caccgtactt aggtgaagga gaatcgataa agacttccca ctgacaagag   2400
taactataca cggctttaga gaattgagtt aagacaaaca tattaacctc gattcataaa   2460
agcattaaaa atttggtcat caattgaata aaccggggct tccagaattt tcaacagact   2520
gtttttgata tacttgctag ggatatccat attaacgcca tcattcaatt cgttgtccgg   2580
gaggatatct ttaaattcga atccatcaaa ctcaaccttg tcaggaatac cttcagcgaa   2640
aaaataaacc aattggtgca ttgtattgca tgaaaataat ttagacctca ccgcaataag   2700
ttcttgccaa tggtttaatt ctctgttaag aagtttatga gccattgtaa ttcgatcatc   2760
actatcaaca agaaaataac ccaggtattg gtggtcgtcg ctccaaaaca tcctgtatgc   2820
ttgtgcattt ggatttttac aacgaagctt tttaataact aaatttctgt taatcttatt   2880
cacctgtcac ctctttaacg atatttttgt tatcgaaatt ggcatcacaa tacaaaacat   2940
agttatattg cataacacca cctgaagcta attggtctga cacttcttta gccatatcag   3000
ggcggtcacg tttagtgatg ttcatgatat cagcataaat ctgatgttca accgattctt   3060
```

-continued

```
ggtctgcagt catagaccat tcacaaaggt ctttatccaa tccggccgtt accggagccg   3120

tgccacatga tgctactgta aggattgctg cgattaataa ctttttcatt tttaactcct   3180

cgttagttga taggtccata gtatcactac catagaccgt tgtaaacttt attttaacga   3240

atcttctaaa taaattttac ggaatttacg ttttgtctgg cgaatctgac gcttagtagg   3300

cttcacagga aattcgaaga actctacgta ttcttgttca taatcattgt gaccgactga   3360

aagaactagt tcccagttgc ttacagtacg ttggataaac atattatgct taccaaaaga   3420

tttgttccaa aaagaactgg gagttggttt cattagtacg atattcattt attcctcgcc   3480

ttcatgttta tgggcaattt cttcgaattc gttgtcacag tctatacagg ttgcattgtc   3540

ccaagcatca aataccgctt ggtcttcgcg gaccgaacaa ccacatacta cacactcaac   3600

ttcttccatt tagatttcct caatacgggc atcatgttca taaacttcta cgtcgtcgac   3660

atacgcctta accaaaatac tattgacttc agcgaattgg gtagtcaccc acacgatatc   3720

gttttcacgc actgaagctt ctttggtagc ggtatcgccg ttggtgaaat ggccgacaaa   3780

ttttacttta attgattcag acatttagat ttcctcacag aaggcccatt cagcatgata   3840

aaccgtagcg cctttagtat catttaaaca aatcacatct accggagcaa ttacacgata   3900

aagacgaggt tctcctccca ctgaacgagc tgcacgtcca gcataaatct tagccaaacc   3960

gatatcttca gtaaagaaca cacgatttag gtttttctta cgaccggttt cagacaaaac   4020

tcctgtttcc tcaggaggac aaagcatatt accgatatta gcaacactac aacttccatg   4080

ataatacact ttatattctg ctttacagtc gatggttttc attttgttct ccaagttgat   4140

aggtctatag tatcacgcct acaggagatg taaaccctta aaaacaaaaa aggagccgaa   4200

gctccttaaa atttgataga tgctgctaaa tcgtccaaat cacttctatt aacacgcgtc   4260

tgtcgattga cctcggcctg tcgattcatc tcacctgtag cctcacgaac agtgttcact   4320

ggacctggat tggaatcgtc ttcaacttcg taccaacgtt gatttccttt cttaacacca   4380

atcttaaatt tgttgtagta gctcttatcg ccataacgag atttaagctg cttaaccatc   4440

tgcataccca tctgagcaaa ctcttctgtc tcgaccacac ctaacatgaa gtctgcagta   4500

tgtgcaatac caaaggattc agcaatatca gccatatcga tttcggctgc aacgttcgca   4560

ccacgagtag tctgggctgc tgtccacagc aataatttct tctctactgc aagcccacgt   4620

agttcttcgg cgaccatctt aatcaatccg taactgtttt cagagaaaac tttcgtacgg   4680

gatgatgcac agatagccaa gtagtcaacg ataaccacct gagggacaaa gttttgtttg   4740

agcttgtatt cgtttaataa tgcacggaat gtatcggcat tcgcaccgcc agtaggatac   4800

tgtttaatct ttaaacgacc taaggtagca gttgaacgcc atttatccat cttagcttta   4860

tattcaggcc aagagacgtg accatcatca atatcgtcta gtgatacatc cagaaggttg   4920

gcgtcgatac gcttagcaca tacttcctct gccatctcca tggagatata aagaacatcg   4980

tatccagatt gaagataatc agcagccaat gaacaaagac caagagactt acctacgttt   5040

gttcctgcca acaatacgtt ttcagtacca aactcggcgc cgcccttggt aatcttattc   5100

agaatattaa gacggaatgg aaccttacgt gctttatcgg aataactttt gaatcgttct   5160

tcatagtcat ccatccagtc atgacctaat tcagaatcga aacaaatcga taatgcatca   5220

cgcatgatat ccggaatggc accgatacct ggaagttttc tattttgttg ctcaaccgga   5280

aggtcggcat tagtttggat ttcaatgatt tttgaagttg cattatacat cgctgctttc   5340

tgaacgtatt tctccgtctc tttaaccaac cattcttggt cttcaggtcc ggcattcagt   5400

gaacttaaaa gctctttagc gccttggtgt tcaacttctg aaagcgtact gttatctaac   5460
```

```
gcaatactca atgcattctt agaaggcact gcattatatt cattgacgtg ttttttaatt   5520
tctttgaaaa gggtctttgc aggaccctgg tcaaaataag aatcattcat ataaggccag   5580
accttagtga aataatcact attgcctagc agttgagcca aaatagtttc taccacttcc   5640
accacctctt agatttaatt ttatccagtt cttcttgtat ttgcattgta acacattttt   5700
ctacatgaag cgctagctct tcttttcggt cttcggaagg tgttccgaaa tcaaccgaca   5760
cttttccatc tttctcaata acaatattca tcacataaac gatgtgagca gtgccatcgg   5820
gtaaagtaag cataatttcc tgcttaaccg aacccattga cttacggatt atatctaatg   5880
atttctcata ataacgaggg tcactaggac cctcttcggt atctttaaca aaattatcta   5940
aatcagataa atcagtcatg gtcactcaca aaattcatat tttctaaatc gttttcgata   6000
tcagcagcgc tttgggtatt tccacctaat ttaacagcaa cgttcttaga gacacgagag   6060
ttaataaggt cgttcactgc atcgtcaact tctttaatag aattaattgc accgagctta   6120
tacttattct cgattgcttc acggaacggg gcatgtttaa acagcggtcc ccagaactca   6180
acacaatcgg tagctttagc acgccatgct ttttcttctt gaaccatttc gcctgtggtt   6240
tcgtcaagga atgcacgatt ataccaacca gctttaggtt tcacgacaaa gccgatatca   6300
gtagccattt caagcaatcc actgaatggg tcgataccgc cttcaaagtt aacggtgata   6360
gggaacgttg atttctcttt aaccgtacga gatttctcag ccttcagtgt aaagtcataa   6420
cctgtgagct cggtaccatc tttaacctga cgtttagaga taaagaacac ggtagaagca   6480
gagtacagaa taccagtacc accacccata atctctttag gatacattcc accaatttcc   6540
atagccgtat ggttgattgc tacacaaggg atatccttga tggtcagata aggcgttacg   6600
atacggaaca gagatttcag tgacttagca cgggtcatat cacctacaac tttctcgttc   6660
aaagcatctt cggtttcttt cttagaagcg gtgttaccaa tggagtcgat aaagataata   6720
accttttcgc cacgagtaat ttcttctaac tggttggtca tatcaacttt aagctgttcg   6780
actgactgga ttggtgtatg aaccacacgt tccaaatcaa cacccatcga acggaaataa   6840
gattctgaag caccaaactc agagtcatag aacaaacaaa ttgcgtctgg atatttcttc   6900
atatacgccg caaccatggt aagtccgaac aacgttttaa agtgtttaga tggagcagca   6960
aagattgtca aacctgattg taagcctgca ttcaacgcac cacctaatgc aatattcagc   7020
atagggatac gagtaggaac ttcgtcacga ccattaaaca atttagattt ggtcaggtcg   7080
gcagtcattt tagaagtaga agctttaatc aaacgggatt ttaaatcgga cattatattt   7140
ttccataggc accattatat tttactcacg ttttaagata gggtaattat atcacttcac   7200
atttacagcg ttaaaggacc acgtcctcat aacttggcat ttcgtgctca gaatggatat   7260
gggcaccgaa ataaatgaat tcagccagac caggatggaa tactaaaccg ggattctcat   7320
gataaatgat atgaggtctt gatttcagaa tctgataata ttcaacctta ctcggtttga   7380
atttaataat ctctacatca ggacgatagt tttcgcgctt aaatgaatca ttcgggtcgg   7440
taatataaag tcgagcacct tcagccgcag cttggtctac aactctttcg aattgataac   7500
atttatctga gatacggaac ggatggaaaa taccatcaat tttaataggc gctagacctt   7560
cagagtaacg ctcaattacc gccggattaa ttaccttttg gtctacaaaa atcttatcag   7620
aggacgcacc tcgtgacacc aggacgtctt tctggcattg attcaggact gtagtataaa   7680
tcgaacgttc aactgaagac acgtcggtat caatgaactc atcgatgtaa taacgaggaa   7740
cttcagggtc cattgtaatg ttaaagttga attgtacagt ctgagtgcca tcataacctg   7800
```

```
tgatatcggt tactaatcct gagcagtcat agtattcgat taacgaatca acaacgaact   7860
cattttcaga ccaaaaatgt ttacgggttt cataagcatt ttctttatac caaagtggta   7920
cgaaattcag ttcagggaac aattcaatac attctttgat atcgctcgaa tttctaggat   7980
aagccagata atcacctggg cgagcacggt ttaaatggag ttgaaaatta ccgtccttaa   8040
ggacggcata ttcacctgtt tcgtaactac gcatactgaa aataggaacg ataaacagac   8100
tcatttcagg aatcctcgaa cgtagtcaaa atcacgttca aatacatgtg cactaaccat   8160
agtatgggaa tacgtaccca gaccaacacc acactgttca gcaataaagg ccatcagttt   8220
accctgcaga tagaaatcca gctgcataac gatagcacag ttctgtgaac gcatatgagt   8280
gtgtgcatac agacgtccat cacgaatata atatgttacc gaatcggtac atggatattc   8340
tagggattcg tcagaatcaa ggagggcttg gtcttgttct tggagaattt ggaacacaac   8400
tcgtctcgag ttaggctttt ctttaagctc tttaagtagg gctgggagtt gggccacaat   8460
tcgaggtcca tagaaagtgt tgaagtttgc aggcaatacg tcacttttcg gcttatcaat   8520
gaacttagca acattaggat attccttaaa tgcttcggcg gcgtcagtac caccagaaat   8580
cataaatttc cagaaagatt cggcataatc atagttgata cgattaatac gagggtcggt   8640
gaatttatag gtgcttgcat ccagtacttc taccgaagca gaaccaattt cataacaacg   8700
gccgatacga gaatcaactg caaactgtgg agcttccagg atttcttcgt tcatttgctt   8760
aaacgcgttt tcaaaactaa cagcggtaat gtgtttcatt tattcacctt attttcaata   8820
tattcattca gacgttttaa ttctaccata tcgacgttaa gcaagttatt atggccgtcg   8880
tgatttaaga ttttaaacac gttttcaaaa catgtttcat attgccggat agttagattg   8940
aactcatctt tggttaattt aataaggtcg tcttcgaagt cttcatctaa tgggttacgg   9000
gttaaaataa cctcaataat attgaattca gatttaaacc ctttccaatc ttccagttct   9060
acataagggt ccatttcacc acgaaggaat ccagagtaaa caatattact aggatatcca   9120
cggtctaaga tgtagacaaa attagggtct aaaaacttat ataaggtttc gactaaagcc   9180
ttatcgttat cagtccctaa tgaaatgcat ttgccattaa tctttttagg aaaatcaata   9240
agacgatatt tcttatcaga taaaagtgat tcaattaaag tagacttccc ggaattatcc   9300
gggccgtcga taacaattat ttttggtttc acggatgata tgccttatag gtttcaagag   9360
ttccttcacg aaccatttct ttaaagtggt caggtcggat tgctcggtca tcgatgataa   9420
aagtataact cggcttatgt gtaagcagat tatgatattt caatccaatc ttttcaaggt   9480
tcttaaccaa tgcaggaact acttcaacca agattcgacc aggtccacat gaagtcatac   9540
cacgagcagt gaacaacgta atctcataac cttcatcata aagcttatta atcatggaca   9600
ccatttcggt gtctggttta aagttttcat aatcacggtc gtggttccaa accgtgattg   9660
tattatcgat gtcaaaacat aaatggggct tattttctac tcgatgcgac attaaatttt   9720
cttccattgt ttgtggagtt cagtagaacc cgtaggttta tattttacac cagtttctcg   9780
gtcaagcaaa acccacttat caggacaacg agtaataatt tgagccgtaa tagggtcgcg   9840
aacttcatca acgaattcac ctgtgataag cttacgctta cgaggatgcc gcttcagcag   9900
cacactcagt tgatataaac cattgtaata agcacccaga gctttcagag ggttattttt   9960
aaagtaacct gccaatgcca tccagataac agcaatccag agcttgtgct taaatgtaca  10020
cattggaata tcatctaaag gcataacctt ttcaatatca acgaatacac gagttccgtt  10080
acgagttaag ccgccccata gagggtcaga gttaaatttg tcataaccgt cgatagaata  10140
aagcacctta gcttcgtcat aaatcgcagg gcctttagaa ctattaccaa aataaccacg  10200
```

```
tgggtcgatg attttaatat caccttcgtc cgacaacata atattactgt agtgcgggtc  10260
accatgaata agttggtacg gttctttatg ttcagacaga atttctagtg catgacgaag  10320
aagtttttct gggtcgccta ccttaaagtc attgacatgg gtaatgccct gtggagcaaa  10380
gccttcaatc aatccggcaa tagaagcatt acgaatcagg accttgtcca atacttcttt  10440
cttaacatca gaataccatt gctcatcgga tggattatcg atagttccac cgaatgaacg  10500
caatgcacta acgaccttat aaaccatgag gactttagtt tctttagaca taaaccggta  10560
ggcatctgcc atggtgcgac caaagatacg ttccatttta atgaattcac ccggagcaaa  10620
gtctacaatg ctcggaacga attcagaatc aatagaattg taccaattga tttctttaga  10680
ttggatttct ttacctaatt cgttggtagg tactttaatg gccagattct cagtgaactc  10740
taatttatta aattcacggt taatttcaga atcttcatgg gccttagcca gtttcaattt  10800
gtcaccgaca tcaactacaa agtccagctt acgttctgtc aaatggacca ttgaatccag  10860
gttgtcggca aggtcttcgc cataatacag actgttaaaa cctgtccaat tggctacttg  10920
atacaaacca actacaccac cgccagtacc aatttcacgc aagtacggtt cttcaaatgt  10980
aaaacgacag tcagtcccgt aggtataaca gtagtcatta tcccactcaa ctttatgacc  11040
ctcaggaatg atgtcacacc agttaaacag gacattgtgc ccgatgatat cttcagcaat  11100
gcaatcgata gcatgagctg aaccattggc cacatctacg ttacgaatag tgaatttagg  11160
cttatcacta ttaatcatgt taatggattt aatatagcct ttaacgaggt cgttaaattt  11220
gctgtgaata accagaataa tttcatctga ttggttacta tacaaatcat acaaatgttt  11280
taatactgta tgctgtttgt agttaaccaa taccttaggg atttcgttag taattggata  11340
caaccgtgag ccaagacccg cgcctaaaat aacaaccttt ttcattatct gttcctcaag  11400
tgaatgtagg tacattatac actattttta ataaattggt attgcttaaa tcttatcttt  11460
accgatttcg atgcactgtt ctattgctgc tggcactttg gtcttgagct tattgatttg  11520
tttcttataa tcacgggctt tatcgaaact ctcggtttcg agcatttcgt aataacgagc  11580
ctcatggata gaaatctgta gattgatatg atttacgcac atcgcataca gtttctgttt  11640
tttgtacaaa tcgtcttgac gcttcatttc tgcctggtgt ttggctagta ccgcttcacg  11700
cttggactct tgttcgcgtt ggaattcgat ttccctttga gcatattttg cacagttatt  11760
accacattga ttattagctc gggtgtacac aagtccagaa cctgcacgga atttcatttc  11820
gccatcgaat tgtttctgtt cagctgcgat acgagcttta ccaacttcat cggccgaaac  11880
tgcatcacca tattggactg cgcaacctga taggagcata ctcattgcga taattaactt  11940
tttcataata tcctcaatta aaacagttat acttaatttg tgctataaga ataatccatc  12000
cgatgattag tgtcggaatc attggtggaa ttgccactgc ccaataaacg gtaaaggcgg  12060
tcattataag aaataaaata attattttca ttgcttaaca ataatgattt gcgcgtttga  12120
tttacgttca gcgacgatag cccatattaa agccactacc caaccaatca tcgtccaacc  12180
caacaggaga ttaaggaaga aaattcctac attactacga gtgcctcgca gaagagctaa  12240
aatccatggt aaaaagtaac cgatgaacat aatagccaga gaaccaaatc ctaaaacacc  12300
agcactaacg attaaagctt ccattgtaat ttcctcatgt agttgatagg aaggatacta  12360
ccacgttcca tgtggtatgt aaacacttaa aagtcgaaca tatcaaataa tgttgctttt  12420
ttctcgtagt cgattttagc agattcagta aaaccggtca gaggcttgat aaaggtcttt  12480
tggaaaagta cgttgtagtc catccaacgg aggacttggt cacgaatctg aaccggaagt  12540
```

```
tcaatacctg atggccatgc catacaagct tcaccaaacg ggttgccttc tttaagcggc  12600
agtacatata ccttttcacc atcaacgata cgaggcatag tcaaatcacc tgcagaagca  12660
cgcatgtaag ctaagcaacc tttgatgtgg tacgggcatt tagaaccagg gaatccacct  12720
tcattatatt tctcgatgtt gttagcactg gatactgcag caatgcttac atagttcagt  12780
tcgttaaatt ccttattaaa ctgtttgaaa tattcttgca aagaggcctc gccttcttga  12840
agcatacgac ggatacattc cttcagagct ttctgaactg ctttaggtgt acttgatttc  12900
tgagtttcca gacccatgat tttcaagtgt ggttcggcat aacgagtacc ttccatgtcc  12960
caaacgttca gtgcataacg tttcttgcct gtccagaatc cgccaagacc tttagaacca  13020
agtggaggac cagcgatagc ttctcggtcc atgaacatca agtgctgttt gttgttcata  13080
tactcgcaca tctcacggaa gcctgcatca atagccggtt ccatacgttc acgtgcaaat  13140
ttatctaaga agtcaaccca atggttagta tcacggaatt tatcttcgcc tactttattg  13200
atgattgcat ccgccttaac ataaatggag tcagtatcgc catagagcac gaacttctga  13260
ttttcagttt tacacacact attcagatat tcgttaacct tacgttcaat ccattggagg  13320
gccatttgac caaacaatgt gattgcagtt gcgttcctga ggtcgtagta gcggaaccat  13380
acgttaccaa gtgcaccata aagggagttg ataagcaact tacggttaat ctgagcagtg  13440
ttacctgcaa cttcagtgag ctcggctttc ttcaacattt ctcttaaaga aggcgctgac  13500
agtgctttaa tctgggcttt gatttcgtca gagaagtcaa aacgataatc gatatccagt  13560
gggctatcaa ctgagagatt aggattttcc aatgcttctt taattaactc accattacgt  13620
tgagctgcaa gcatgtaacc tttatgttct ttacgctgca agaatacctt ggtgatttct  13680
gtcggaatca caccttcacg gtctttataa tacatcatgc cgttaggaga gcaactgtag  13740
acatcgctag gacgctgagc agttccggca atatattcat gtatcggtgc gttagcgaat  13800
gtgcctgcga tggtctctgg gcttatattc acttgtcgaa tgatactcgg gtacagagat  13860
gtaaggtcga aactcattac atatttgtaa gcgttaggaa taggttcctt aacgaaagca  13920
ccaggataag gttggaccac gtgtgaacga gcttgtggaa tgaccttgcc ttgttcttta  13980
aggctattaa agataatagc atcccaagtc ttaattggac tgaacactga ctgaatctgc  14040
atcttagcat aataacccat gtccaaactc agaagaatga actggcgttt catatcaatc  14100
tgcactacac gatatacgtc gataatgtta taggaaatat atcgttggtg gttcgtctca  14160
cgtaacttgg agattggacc atcatatttc aacttaccta ctttcaattc atattcagaa  14220
acataatcca aagaataaga aggctggttg gtaaagctga attttttata caggtcgata  14280
taatccagaa cagagatacc gaacaatgta ataatttcac gagcaccgta catgttctcg  14340
ataactttaa cacgggtctt acgatgcggg cttaatcgct tagcagtatt ctcaccaaac  14400
agatttttca gacggttata aacgtatggt acgtcaaacg actcaacgtt ccatccagtc  14460
aaaatcacag gagttttctg ttgccagaaa ttcaaatact caagcatcat ttcttcttcg  14520
gaattaaacg gaagataaac gattttgtca atgatttctt gtggaacttc gtcaccacct  14580
tcttcttgga gtttctcagc gattttaatc gaccactctt caacagtacc ataaggcgaa  14640
actaaaaggt cgaatacata gaatttatcg tcaatcgagt cgtagtgggt aatggcatcg  14700
ataggatgtt tagcctgagc tggttcaggg aatccatcag gagatgttac ctcgatgtcg  14760
aagttagcaa tacgaatctt agaagaatca tatctgattt ctttacgata ggtatcagac  14820
aaataggcca atttatagtc gtccatacct agggcttcga ggcccatatc gtccatacgt  14880
ttcatccatt gggatgcatc acgcatagag tcgaattctt tcttaacaca acctttacca  14940
```

```
tagatatcaa tgtattttac ggcttgctct gggttagcat gcataaacat tgtaggcttg  15000
taaggaactt cacgactacg ttcgttacca tttttatcga tgtaacgttc gagaatatta  15060
tcaccgattt gttcgactgt caaatagaat tcttgcattt catttccttt atagacgagt  15120
gattgtcttt tgtttgttga tgaatcatta tactccaaaa agggaccgaa gtccctttgc  15180
ttaaatttct attgtaaaac gtttaatgga tggattgcca tattcgtctt tagttctaat  15240
catagcctgg aaaactcgtt gacctggatg tagtaactta tggaggtcct tttgaaattc  15300
tatttggagc tcttcggaaa ggtcaaaaac agtttgagtt ggggaaagtc cgtatacctc  15360
tttaaggcgt tcacacgttt caatttcaag aatcatatta attaccaatg gtgtacttgg  15420
acagtagttc ccagtcattt ttctgcttaa aggaaatgac acggaaatta ttagtgattt  15480
cgaacagctc agagtcgtct acgatatcaa tcagtcccca ctccttaaga agctgggcaa  15540
tcgaatcacg acgttggtag tcttcaccat cgatatcaac ttgacggcca tccatacgca  15600
acatctcttt aaagtggacg atataatata gcccttgttt ttgcagaatg tggcaggatt  15660
gatatagttt cttttcttta ttattagcga tacccatacg agttagggtc tctttcactt  15720
tcaagaagtc ttcaggttgt ttcagagtaa tttcaatcat tttaatttac cattccaatg  15780
ctttcttttt caagtctttt tgttctttaa catttttagt tacggatttc aggaactcgt  15840
ccgtaaccaa ccctttcatc ttcttaagca ccgccggaag atggccttta attttataag  15900
tctcgagata acgataagcg tcatcattat taattgaatg gtatttcatc aataaacgag  15960
taataaaaac cacactaact tcatcatcat gggccttagc ccatttacca aatctcttac  16020
ccttaggaac cgcatgtaaa agatagttga agtggcttg gtcatcaagt ttcagacagt  16080
taaccattgc agctggcata atgcaatcta catgctggct caaactattg tcgagccaaa  16140
attgattata gttttccgat tgagccaagt tacgttgttt cttaccatat gtgatatcgt  16200
tcataatggc aaacaattcg ttttcagcct tttctttaaa tgaatcggcc aaggcttgaa  16260
tagcagcatc gttacgctgt ttccaagcaa cttcatgttc gttcagttca acgtcatcat  16320
caaaaagact tatagccatt ggagctccag agcaagttgg atgaacagat aagtcatgtg  16380
aatttctggg ttagccgcaa taccgtggta ttggttattt tcaccgacaa tttcatacat  16440
tctaacaatg ctcggcccag gcaatttacc gtagagttcg ttagccagtg acataataaa  16500
gttggaatag tcattgacat ggcgtggagc taatgcacgg agttctttaa agtttttatc  16560
tttcagtgca gccactactt catcgatagg cgaattggta ttcattacaa tactcagaat  16620
gcctgtatcg attttaccac tggatgagta acggtccagt tggttaactg ttttacggaa  16680
gtcaggaaag ttttgtttaa ctaaagcagc aataacttta aggtcttcga cttcgatatt  16740
ttcgttttta cagattgcta cagcacgatg aatcatttct ttcatcatgg atgtttggtc  16800
tgccggagtg gcttcaccaa atttaataac acgacaacgg gattgaagtg gaccgataat  16860
accatcaata ttgtttgctg taataattac agaacagttt gaggaatagg cttctaagaa  16920
cgaacgaagg tgacgttgag cttcagcaac accagcacgg tcgaattcgt cgataacaat  16980
taccttacgc ttaccttcga tagatttgga agatgcaaaa cgagtaagtt cattacgaac  17040
gaaatcaata cggcagtcag aaccgttaac aaacagcatg tctgaatttg tatcagcaca  17100
caatgcttta gctacggtag ttttacctgt gcctggtgaa gaagagacta ggataatgtt  17160
agggattagg cccttattaa caatggcttg gagggtttct ttatcatgcg caggcagaat  17220
acactcagat aaagtacctg gacgatattt ctgttcgaac atgaattcat tattgtttac  17280
```

```
tgtaagcata ttaatttcct caggtttgtt tttacattat actccaaggg aggagattcc  17340
tccctatgct ttagaacgag tggcttgagc ctgcttccat agccaataca taagaagctt  17400
gtgaaccttc aaacttggcg gcgaaacgag catcctgacc ttcaccacga gcccatagca  17460
atacatggta atcagcaggc atcattttca tattagtttt gttgataatg aatttgaatt  17520
cagggccatc atggtctgca accactaagg aatacaatgg acgtgccagg tccttatcat  17580
caacttgctt gtagccattt attacaattt taccattgtc tacagtaata gcaaatgtat  17640
caatactcag accagaggac acacgcatca gctgctggta atcttcagct ttaaggtcaa  17700
aaataacttc agccaccggg aatggaatag ctttgcttgg gaatgcaatt gtacttgggt  17760
cggcaatagg ccacttaata gttgaacgtt ggtctttaat aattaaagtg gtttggtctt  17820
cacttaccga aacttcagca ctatcggata ccaatgatag aatacttaag aagccgttca  17880
aatcgtagat tgcggcttcg atatcaaagg tatcacttac agtagcttca ccataacttg  17940
cacctgttac tgaacgagtt agaatagtgt taccaggttt aagcatgata cctgggttaa  18000
taccggagaa gtttttcaga atgttaagag tttctttaga gaatttcata atgtttcctt  18060
atcaagtcaa aaattaatta agcaataacg atcatttgtt tacgaatgga ttcaggcaga  18120
gattcaatat actctggaat ctgggaagca acaatagcac cggcttcaag caactgttcg  18180
tcaaaatcta cgcaataatc atcttcgaga cgttcagaac catcacggtc gataaccagt  18240
ttagcacctg cggccagtga atcattatag tggcgacgca taatttctac ccacttatcg  18300
gatacgtcgt tatcaatgat accgtagagc atgaacttag tttcttgtgg aagagattgc  18360
aggcgacgtg cagagtcagt atcaatattc agtacccatg atttacggat acggttttgg  18420
ttatgtgggt tggaatcagt acgaatggtt ttaacttgga tatctttaac agtaatagcg  18480
ttagcaaaca taatattttc tctcatttgg ttggtagatg tattataaat caatatttta  18540
aagcacttaa cgtttaatca aagtattcat aaacgaacca ggctgggttt ctgttcgaca  18600
tgattctatc atactctgac ttaaaagcat ttcggagata atcttcagta acaagatgtt  18660
cgtctccaga gaagttgtta actaaaacat atctctttat ttcaggaacg gccaacaaat  18720
gctggcctgt tataaaatca ctcattccat caccgtgaat cgtccaactt tcttcatttg  18780
aagatgttgg ccataagctt gtgggtcatg gtctcggtga gagataatga acacgttcgt  18840
atcctcaagg ctattcaaga tggttgcaat ggtcttaacg ccttcagcgt cagtagcact  18900
gtcaaatacc tcatcaagaa ttaacgtgct gatattaaca cctgatacct tagaagcaat  18960
atcacgccat gtaaaaagta gtgcgatatc aatacgtgct ttctcaccct gtgaaaatga  19020
agcataacta aagtcttcac gtccacgtga tttaatcgtc tcattgaact cttcgtctag  19080
tgtaaagacg tagtcggctt ccataatctt caaataagaa tttatctgct tattaaagat  19140
aggaatgtat ttcttaataa tggaaccttt aatacctgtg tccttcaaca tttctgtcag  19200
aattccacga tgatattttt ccattaccaa ggacgatttg gtagagacga ttttatcaag  19260
ctctgcttga agcgcggcaa tctcttcagc attacttacg aactcagcag ctgcttggtc  19320
gattaatact ttaacttttt tagctttctc tacagcagta atggcttgtt gcttatgagt  19380
agctatctga gatttaatag ccagtgcttt attacgttgt tcggttactt ggtccttaat  19440
gagcttgagt tcttggtact gctcattaat cttatccaaa gatttttgaa gctcaaagtt  19500
cttatcctta attttagtaa ggatatttcc atgctcttcc aatccttgca tacacgtagg  19560
gcagtggccg cctgtttcgt ataatttcac aaccttagta aaggttgcca tatcattctt  19620
gattgcaaat cctttattgc tcaggtcact catagagttg ctagggtcat catcgactat  19680
```

```
gacattgagt aattcatcag tcagtttttc tatattgccc ttcgcagtcc tggcttcttt  19740
aacgagctca tcgtacattg tttgtagacg tgctgcattt tcaccggata atttacgctg  19800
acgttcttcg ttgtcattat aaattttaat ttgctgggta atagaatcct gtttaacgtc  19860
gattacttgg atttggctat tagtctcacg aatcaaagat ttgttcaact tgtccatatc  19920
cgctaataca gaaacctcta acaggtcttc cacaagcttt cggcgcgcag ggtcgacaa   19980
acccatgaaa ggggtatacc ctgctgtacc aagtacgaca atctgtttga aactggcata  20040
tgacattccg ataagctgtt caaattctgc ttggaagtct ttactgctgg cagattcatc  20100
aagacgttca ccgccacaag agatttcaaa aacgtttggt ttttgcccgc gtttgatgta  20160
gtattctttg ccatcatatt ccatccacag ttcgaccaaa aggtctttct tattacttga  20220
gttaattaat tgccctttct taacatcacg aaaaggctta ccgaacagag caaatgtaac  20280
ggcttcaagg aacgtagatt taccagcgcc atttttaccg gtgactaagg tcttttggac  20340
cttgtcaagt tggattgtaa taggttgctg gcctaccgac ataatatttt tatacgttac  20400
tttctttaac ttaaaagtct tcatcgttat aagcatcctt gatgcatgat tcagccatat  20460
gaattaatgt ttctggagta tcatctacca ttacattaaa gctaaattcc acagcccaat  20520
cagtagcaac ataaacttta ataagctcgt tggtatcacg agtgctcacg gcttcaaacc  20580
agaacttaat gatattcgtt tggttatcgt catcaataac gatgcagtcg tgttctagtt  20640
caagtcctga tttttgaatt catctaaagt catcgtgtaa cctcattata aagttgtgca  20700
gccatagtct taagggcttt aacatcgtct tcagtgtggc catcaggaag ggcattgata  20760
taatcataca tcatgtccaa gagggattta acttcatctt cctcttcaga atcatcgata  20820
tcaacactgt tatctacctt agacacgata cgtaaagaat ggacaacctt ttcaagctct  20880
gattcgaact tagtaagacc gtcatcaatt ttatcgacta taacacgaac tgcgatattt  20940
gtaaaatctt tgtaatcgat agtcgcattt ggataatgaa tcttacggtg ccaacaggtt  21000
tcattaatga cgaaatccat cttatgagtt tctgtatcga aaatccagaa gccgcgaggg  21060
tcgttttcat caccagcagt cagggtccat ggggtaccaa tatacttaac gtttgctgca  21120
tcagaaatag tatggaagtg cccagaccat acctgcttat acttcttaag gaaatcaggt  21180
tctaaaccat gggatttcat tcctttatag aaatagaaac catttaattc ccagtgacct  21240
atacagaaat ctgccgtggt atttttgata tggtccatga tatcggtcgt gttttcttca  21300
cacatccatg gaatcaaatc aatttcggtg ccatcaaagt taaccgtagt aggtttctca  21360
ataaccttga tatggtcata tttacccaga acttcagaag cagcgttcgg tgtcaaggta  21420
tttttgtagt gggcatcgtg gttgcctacg acagtataca tggtaatgcc gttggtttta  21480
agcaaatctg aaatatgtct agcaaattcc atgcacttat gagtaattgc tttacgaaca  21540
tcaaatatat caccgtactg aatccataca gtaatgccat ttgctttaga ataattgatg  21600
gcatctttga tgccggccaa ttggatgttt tgcacccaag ggtcgtcgtt cttcactcca  21660
aggtgccagt cacctgtgtt taatattttc ataagccaag cgccgttatt gcagtgcaaa  21720
ataaaattat tgaaatgaac ccgtcaggag tagaaaagaa tcctatccaa caggctcgtg  21780
tgaatgtgta gaatgccatg aataacacga catatcctaa aaatagttcc atatgttctc  21840
ctcagttggt tcattttatc atccgaatat aaagcaaaaa aggagcctaa gctcctttac  21900
caactaatac accatacaga ggttcgtgat tagacctgaa cttgataggc ttatatgtaa  21960
tagtaccttc attttctgct ttaatacgag cggcttcaaa tttaagcaac atctcatttt  22020
```

```
tgtcagattt aatcttatca aaatccatcg aattcgtcat tcatacaacc tcttaaactt  22080
tttcgtattc gtctttcatt agccacctgt ccatgttatc atcgttgcca ccatttctta  22140
agttggtgtg aatccaccca aaccttggct acaggctcaa tcttaaaaat accatcagaa  22200
tattggccca tcattttata ttcggtttcg gactgcttaa tacagatatt accgtatgag  22260
cgaagtctaa aggcggcccc aataagaagc cgtttaaagg gtttatttac tagggccatt  22320
gacgatttcc caaatttgtt tgcgggtaga ttcccacatc aattgaacaa gttcatcagt  22380
aacaggttga cggtaaatac cacgtaattt aattaaagcg tacttatatg cttcaaagtt  22440
gttttcaagt acagcgcctt gggcatggag atttaaacga cggatttcac gagcattctt  22500
cttaagaatc ttagccgctt gagaattagc ttctttaata ttatgctctt ctaaacgttg  22560
ctgggcttct tcaatttgct catcggtcaa ttgagaaatg tcacggcttt gcatattatt  22620
cctttggagt caattcaata gtgaagtaga aattagcgtt ctcaacatga taacgataat  22680
ctacgttatt gtcaggagaa gtgaattcaa tattcctgac gttaagtggg tcaatatcaa  22740
taggaaggcc tttaacatcc cgtaatatca atttaataaa ataagggagt gcttcgaagt  22800
cttccattcc atctaaaagt ggagtgatat taatctgatg ttccatataa aaaatccagt  22860
tcaccaactt taggttcggc actcttatca gaccctggtg ctttagttaa agaggtttca  22920
tactgtgtca ttttatcgta gatatcttgg ataaaggttt catctgcaat acctaccata  22980
tcgtcatcat tactgtcata gacattatgg acgaagtagc tatatttctt tgccatttct  23040
ttacgttctt ttttgatacg ctgaacgaag gcattaaaac aagccatagt gatatatgca  23100
tgcgggttgt cgtattttgt ttcgtcgaag ttgtgaagac ctttaatcga agcttcgatt  23160
ccatcagcta tcatttcctg ccgccaagat tgggtatatc ctgagaagtt gaaacgcttg  23220
ctgaggcctt ctgctataag cataatagcc aatcctatag tatcattttg tctaatgatt  23280
ttattagggt cggtattagc atataattcc tgcttccaac ttgtaatagc tttaagaagc  23340
tccttgttat ttacataatt attttttgtt aacttcacct gattcataag ccctcttaaa  23400
cctatcaact agtggtctaa aattatttat cgtatacgga taacccagtt cacagcattt  23460
gcgccagaat ttagaataac tagggcgtcc ttccttaatc caaagttcat ggaactcatc  23520
atataataca tatgttggat ttttagcaaa cttggaataa ttctctatag agtaatattc  23580
tttgttcttt ttacttttgg cctctctaac ttcaggattg gcattatatt ctttatggat  23640
tcgccgcatc atttctcgat gctcttcgtt ttcccaagac tttttaatag agttggaaac  23700
ccgctcttta tattcagggt cctgccagcg ttcggtaact tctttagact gttcttcaag  23760
tctttccggt gtcggaggag cataaccacc tataccacca ggtttcatat tgacacagtt  23820
agttatttcg gacatagcat tttctaccaa aagctcttca aattcaaaag caagctcact  23880
tgtctcaaaa taacataagg cctctatatt aaaagagcat ttccctgagg ccttagcatc  23940
ttctacgaat ttgccactac cgacataccc gtcatctata aatccggtgt gtttaccgaa  24000
atagtaataa gtatcatttt cggattttat agtggtcata taacaatagt gcataacgat  24060
taatctttaa tttaaataat gaatctatta tataccaatt ggcttaaagc atcaacggag  24120
taagcaataa gcctgaaata ctgtttcaag gatttttttg aactcttcaa aggaaggggc  24180
tccttcaaac ccttggcttt gaatgtaaag acagaattgt tggtaaagga ccaaatattc  24240
tgattggttg tatttggaaa tatgagactt ccacacttcg gaagtctctc cacaaacaaa  24300
ctcaacattc atatagctat ctattaagaa aatccctagt ccttcgtagg cgagggtggt  24360
ggatacgggt ttcattgtag gaatcgagct ccttccaatg cgtcatccag attatcaaac  24420
```

```
tcgtccacgt aatcaacacc gccaacttcg tccttcgcat acaaccaata ctggtggaat  24480
tcatattcaa taataaagtg ggcaccttca atctggagag ccccatcacc gttaaattga  24540
actgcataac ctgtaaagcg gacatcattc aagagttctt ctttcatagc aatcatttcc  24600
aagtttttat cgtaattaga gagttttatt ttaatcattt aaataatcct caaattcatt  24660
taatgtcatg ccttcgtccc aagctatttt tgggtcaggc attttcatat aagtggtctt  24720
agagcttata ggaaatatcc tgaaatcacg atgacttcca cttagcatct tagccgcttt  24780
tataatagtt tcaatattat tcatcatggg cgtacgttgg aacccggcta aagctttaag  24840
gactattata accgatacat cttcaggcaa attactcatt tagccgcctt aacaatttta  24900
aggtcaacga atttttcttt acgttggttt ttcatacgac ggatagtttt atccgagatt  24960
tcaccagggg cccaagcttt agattcaaca ccaaaggcag cgacatcgaa ttcatcaagg  25020
atatattgaa ccaggatttc acgaataccg ttcttaccaa ttttctggtc tttagagtgc  25080
atgattggta atagttcagc aacccattgg tcaagaacct gaggagttac aaaacctgtt  25140
ttcatcagtt cgtttacttt atcgaaagcg aaagagttca gtacgttttt aatagcttgt  25200
gacataataa tttcctcagt tttaaagtta taatccgtgg gaccattata ctctggtccc  25260
aagagtttgt aaactatttt tgtgctttag cgcctttcca gccttcatac atcattgctg  25320
cggaaattaa caaagcaccc gagcaacttg aatatttgtg attccaaaac cagttcagaa  25380
atacttcgtc atcaatacct tgagctatca tattttcaaa gaactgacga cgagcttcag  25440
caattcgctg tgataattta gattcaggat tcatttaaat tttccaattg ccattttcat  25500
caatgaattt aacccagtca tttaccgacc acttggttgt atcgcctttt ggagcaacat  25560
ttaaagtata tagcccctgc ttaaaaagca ttcgtttgat attcatattt tcctcagctg  25620
taacgataac actcgtttga tttacgtttt gcaactcgat gagaagtatt gtaatcaggc  25680
tcatcatcgt tgtaaacatc ttttttcagc tttctcactt ctttacgaag ctggcgattc  25740
atttcattct taacttcgga atcaacgcct ctcatacgtt tccacttgtc agaacggaag  25800
atattttctt caaccagttc ctggcttaca ccgtccggtg ctttgcggcg acccgaataa  25860
taaaaatctt ttacagacaa ttctttacga cggatagttt tacccatagt tacctcagca  25920
gtttgcatca ataagatttt taatgtaatt aacgtctgca atactcagat cgagtttaat  25980
agctttcaga cgttcatcca gagtaaggaa agttactcgc ttccaattct taacagggca  26040
gcaataagtc ttaggaccgt tagcgatttc aatattttta tctgtgatgg tgataaaaat  26100
caagcgtaca taatcgagat tcagggtgat gacatttctc tttgcatgta ttttcaggct  26160
catgagttaa tttcctttgc tactgaacaa aatacagaac ggtcgcacac cattaacgga  26220
gcatcagggt gagtcaaagg ttgataccat acatcgagat ttgttacctt tgttacttga  26280
acagggtagc catttactga ataatactgg tcgactttaa tttctttatc ttggatagtc  26340
ataatgttct cctcatgtgt tgataggata gactataaca cgtgaggaga ggaagtaaac  26400
actaatcttc aattaaatct cggtcatagc caagttcaat caaaagtgac ttaaaggcag  26460
gaatattttc tattttctta ttatcgacaa agatgacagg atagcgtatc gctaagctct  26520
tgaagcctgc gcgtttggcc aatgatacta taagaggctt gtcatatacc gcgccagacg  26580
gcgtctggtt aatcacagga tagaaagtat gtgggataga aagggaattt aggagcgata  26640
gaactgcaat gcaccctgga cagcgcatga ctgcctcagg gataccgtag atttcgattt  26700
tagttaactt ttggtccaca ggaaataact ccttggtagt cccaggtttt tagaacttcg  26760
```

-continued

```
tcctcactag ttccatacgg gacgtaaatc tgaataagaa atccggtatc gtcgaagctg  26820
aaataaaccg tcggtttgat tccgtgaatc tctgatagag catagatgtc cttgaggtct  26880
tcttccttat cgacaaagaa ttccgggttc aggtcacagt catggaagta ccaatcatca  26940
ccgaatttgt cccatgcggt ccaattcaaa gctacatatt cttcaaaacg tttcattctt  27000
tcaccttcat cattttagaa ataacaccat ggacagactg gattcgtttt tcgaactcgg  27060
acccttcaag accttttca gtactcaggg caccgataat aacaaacagt aatccaaacg  27120
ggatgaccag gattaaaagg cacacgataa acagggcaaa tgtaatattg gccaggatat  27180
cagaaacagc attacgaaat ttgttcatta aagaacccac atgttagtta caacaaataa  27240
ccattgagca ggatactcaa cacccataat acgcaccgca tcgttcagag attcgattaa  27300
agcataaaat gtgtagccat aaaaattaat catttaagcg atttcctcag ttgtttttg  27360
aatgaatcca ccatttgttt cttagtggca gattcattat aagtcattcc gtgtgaaagc  27420
atttcagcaa tcatttcttc cttacccaac ctgctgaact ctttggtttt atcaggaacg  27480
aaattaggat gaatattgtt ttcagtataa tcagctttca gatagaccag caaattctct  27540
aaccattcga ggtagtcaac gttttgacct ttaagaccag aacggttgaa cttatgcttc  27600
atttgtcctt ctgcagcatt gcacaggtta catagtaaac cacgaacctt accggctttt  27660
ggcccgttta actcgtggtc gtggtcaagg tggttacttt gaacatcagg gtttaattca  27720
cgtttacaaa tcaaacactt accatgttgt gcatcataaa gtttttgttt ttcttctttg  27780
tataatttgc cggtcaacaa cataataaac ccttaccatt attagataag ggtatttatt  27840
aatatcctaa tagtttagca gtgcaactta gcactaacaa caatccgaat aaaacaactc  27900
ctacccaaaa taccgtaata agagcctcca tatcagaccc catagaatga acgatgcaaa  27960
cgtttgaatt gacgaatcat ctttttagta ggacgggtgt ataatcctac acaggtggcc  28020
ataaactggt cagttggact tcctttgata agaagtttcc agaccttacc gccatttaat  28080
ttttcggtat agactaatac agttttcatg cgacctcaaa ttcattatca tcgttagtcc  28140
aaaaacacca gaatgaagct ttagtatctt caaacatttc tttagtgtat tcgtatacct  28200
taccattgaa ttcgatagca gttacgccga tgatttcagg gtcgccccat ggagaaatct  28260
ccaccttcaa gattttaact tcagcgcctt cacaaagctc acctgactca aaaccacgat  28320
taccatttaa ttcaggccag tcaacataat ggtcgacatc ttcttcagta atacgaacag  28380
ttttaccttc aaattcaaat aaattcatca gaaggcctca tcggaaaagc gaagttgagc  28440
ttcaagccaa tgaatataat cggctgcagc tttaatcaaa tcggattcta agtcaggtaa  28500
agaacccaaa tccgacaatt cgtaaagcga atgttcaatc agacggcctt tatgacggcc  28560
aacttcaatt ttggtactca tatccaaact ccatatcgat gaaatcattg tttgaaggtt  28620
cattatactc tatttcggaa tcgttgtaaa ccggttcctc tggctcggta gttttccacc  28680
gagcgacata ccatggctta acggtcacac caccaactac ttacttcaaa atcaggttca  28740
ccgtgttccc agtaccaagg gccgactgga tgccaatcgc catgttcatc ttcttcaaat  28800
tcttcagatt caagcccaac gtattgccat tggacttcat aagcggtgcc acctattaca  28860
acggtgttct cgccatatgg gtgagctaca gcaaagtcta taccttctgc tttagccaac  28920
caaaccatat attcgtatag tttatattcc aggtcatctt cggtgccatc acctagaaaa  28980
atggtttgtt cgtttaattc aatcataatt ccaccataaa ttcaaatagc tggtcacgta  29040
cacaagtatc agtccagccc cattcgttgg cttcttcttt taaccaatcc gggagatttg  29100
ccaatacggt ttctttacta ggcgcaggag tatcaaactc gcttgtaaac tctcttgcgc  29160
```

```
aggttccata agctatatca aattcaatca tttgaagttc cagaatgaag caccaaccag  29220
aaataaaggc caacaaatca tagacgtcag ccaccaacaa aagtcacctg caccgaaatc  29280
atctaattta gctagggtct tagcataacc aataccgatg ataagataca aaatacccaa  29340
caataattca atcatttgaa atatgctcgc aattggtcaa agccaccaat agaagttccg  29400
tccggagcaa atacctgagg catagtcaaa cccacctgag attcgcgacc aagcgcagtc  29460
aagagttcag caatcttctc atcatcaaat acgccttttt ccggcatcac gttaatgaat  29520
tcgtaaggtt gtttcttaac atcaagcaga cgtttggcat tatcacagaa aacacaacgg  29580
tgaatatttg aatcgtaacc ataaacttta aacattttaa attcctaata tttgtttgaa  29640
tgcttcagaa cggtcgagtt ctgttccata tttttccatg tgctcatatt ttaaattata  29700
cacatcagat agtatattat tatacgagcg agttaaagca gattttaaaa ctgaataact  29760
gtctgggaat ttaccatgct ctttataata agctagggta agttcgcgga ctgccttatc  29820
ggcagcctct acatattctt tacgctttgc cattttcgtc tcgctcaaat ttgtgtttac  29880
aatggcggca tttgtaacga agattactag tctgccaatg gaccaattgg acctgttctg  29940
taccgcactc aggacagtta ggaacatcct tagaagcttg ttctcgtcgt gcgaccatag  30000
ccattacagc atcccaatta acggcatcac cataatcatc acaaccatga attttaccaa  30060
ccaattcaac ttcaacatcc gcggctttaa taaatttcaa taaaccggta ttagatgctg  30120
aagcaatatc ttcagctaaa cgttgtttca tttcagcagc tccagagctt gttcaagacg  30180
gtctaaacga ttggtagact cttcccaaag tttcttggcg gcggtatatt ggccggtcag  30240
tttttgtta atagcaaggg catctttata cgctttttct aaggccacga tttccggtaa  30300
cttggattta gtaattggtg taggggccat gatagggctg ttcaagtcgt taatcaaatc  30360
ttctaatgta gcgggctctt tatcagtgtt cacaatttcc tcacattttt cttggtaaat  30420
ttcagcgtca gtttttggaa cggtacattt gatttcacgg actgttacta agacttcata  30480
tcctttccat cctaagtggt gtttaacttc ttgggtctca tatttctcta cggtatccat  30540
cagagctaaa gcctgttcga tagtattcaa ggtatcgtaa gcaatatctt gatactttac  30600
aacttccaca tcatctttag gtttcctatt aggtgaccaa ataacagaaa taatagcttt  30660
tcctttataa ctatttgttt taatcatgca attagccatc gggtgaatag tacgacaatc  30720
accggaaact atagttttag aggccgcttt gagaattaat gcagagttag ctttgaattc  30780
ggtaacccaa cgttgtggaa ataaactact agggtccata cctttaattt tgatataact  30840
ttttatggta tcaccaaacc atttgtagct aacagcatgg ctagaacccg gatgtttctc  30900
tttgccaaac tctgaaagga tgtccttatt gaccagtcgc gaaagcagtc gagaaccttt  30960
aaatgtttta atgatatcat gaatgcacaa acggcctgca atcttttcga tttcagcttt  31020
gaaacagcgc gataatgcat catcaatttg gtcgacccat ttattgatat tagaaactat  31080
taccacatat ggggttaatg gaggggtgtt ggcagtgata tacgtagtaa aggcattgat  31140
gtattcagta cgagtcatga tattctcctc aagttgatag aaagattata ctccatccat  31200
ccttggatgt aaacattatt ttagagctaa tactgcggcg cggagcttgt cacgctggag  31260
ttccatgttc ttgatgcgaa tcaatacgtc ttgaatactc tttttctcat cttcgatctg  31320
accatttaaa cggtggattg attcctggag gtggtcctca tgatacttct cgataggttt  31380
catcgtaggg ttagtaacca ccatagaatt ctcaggcttg attttccact gatactgttt  31440
ggaattgaat ggactaggca cagccgtggt tttgaatttg tcataggctg catactggcc  31500
```

```
tacgctgtca catgatactg cagagatacg tcgttccatt tccggttcct tttgttggga  31560
ttgataaggg gcataagaca aaagatattc acgagttagt ttaacattaa aatacactgc  31620
atctgctcgc ccggaacaat cagcatattc atctgttgta accttatatg attctacggc  31680
cttaatacga gtcattgctt ctctgaataa ggtttcaaat gctccacgaa gggccttatt  31740
accttttgag gtaggacgga aacgaacttg aataccgtca gccaaaatat taatgactag  31800
gttacgagcc gtaaaattaa tattcttgat attgatatga accgtagaaa tacgtcctgc  31860
ggtagccaag aggtctttga tattagctcg taatgttgca ccaaacaggt gggccgggca  31920
acggcaataa tcgttcaaag aactaatata agtcccttta cgtcctacac cataagtata  31980
attaccatta caaatatggc cgaagtcggc cagccgatcg atagcgatac gacgtgtggt  32040
atcaaaatca tatcgggaat attctttacg tgttttaatg ttcatatcaa agtccaaata  32100
atttttcata gaatttagcc ataggccagg ttataataaa aactatccca aacatagcaa  32160
gaactggcca gataaaggtg gcaaacgctg cttcaccgcc tgagttaatt tccatatgat  32220
tacgaccaat aaggacagta atgaatccta tcacaaggta tccaaaaata aaactgataa  32280
ttatagccat attaatcctt aagaagattt aggatatcga tatatttttg acgttcagcc  32340
ttagctttag cattcagacc agagagtcgg aaaatctcat catcttgttg ttggattgta  32400
acattcaagc aagtaagcaa attgctaaaa tactcgattt gagattgatg cttctcattg  32460
ctgcgcactg gcacaggttc cggtttagga gctcgttccg aatgactctt aacttcatta  32520
cccggcttaa caagtttaat acgccggcct gtactggtat taacattatc gaaggtaaga  32580
ataccgctac gttcgagttc ggacaaagcc agtcgaagat ggaatttcca attgtcatat  32640
tgacaaccac taaaagttga agtaagatac tcgttttcgt tacccggttg gttgacaata  32700
ttaaagataa tccaatcgcc tgaaccatta gtcttaaatg gcatttgctt atctttacct  32760
aaagctagac gagcacccag tgctagtaaa cgacgttggt tagtacgaag gtctttaaca  32820
acttcatcaa atgacatcgc cgggattaaa cgaccataga ggtcatagcc tttgttataa  32880
tttctaagaa taattctggc gttagcacga gtcaacatac cggccctgtg aagagatttc  32940
atgactcggt cttctaacgt aaacaaacct ttagtcttgt caaagatttt agtgaattca  33000
tctacagaaa tacaaacttc aaacttttcc cacatcatgg ccaaaacctt ttcaaccact  33060
tctttattca gtggaatacg accaaattta ataacttttt taacttcaga acgaatttga  33120
ttaattgcct gtgacataat aatttcctca gtaagtaatt aagaacctag aaccattata  33180
ccatccttgg tataaagcgt ttatgcgaga accgtcttta aacgctcttc aaatttctga  33240
agcagagctt ggcgttcagc tcgttgtgat ttgtactgct cgatacgacc tgaagtgagg  33300
gcgtactgtt cgtttactga ttcccgcatg aattcaggaa tctctttaca agctttgatt  33360
tcgtcaaact tatcaataac agcttgttgt tcagcaatca gattatcgaa ataagcgata  33420
tcagatttaa cgtttgccag gtcagattcg gtaggcatta aacgtttgtt acgttcagct  33480
tgataagctt gattgttttc acgactccag tgaagagtac gttttttgtt agtgttttta  33540
tagagctcta caataccaac tgaatcgatg actgcaatcc aattccaacg gcttttgtaa  33600
atctctcctc cagatacggt aatctcatta ccacaagcaa cgtcgttaaa gaacttgctt  33660
tgtttttcag atttgaaatt accgttgttg aaattaataa gtgaaaaaat atctttagcg  33720
ttcatgataa cctccagtag ttgataggtc tatagtatca tttctactgg agatgtaaac  33780
aactaataga aacttttttc acctgcttgt ccactaaacc acgctgattg ggtgttctct  33840
ttccgttgat gttcaatacg aatgcgatat tcattcctga tggcgcagag ttcacctcgg  33900
```

```
aagtcgcctg tcaactttac ctgcttgtgg tctagattta ttaaggcctg ggtcttcgcg  33960
gccaggagca gtctcttgta gtctccttct tcacaatcag ttttataaac tctattagta  34020
tatccatcga taagttcttt atcatagtcc tcgacagact gtttcatggc tttggaaaaa  34080
gtctgacctg cgttataaag attgtaaata aattgttcga acataatttc acctttattt  34140
cagaagtgta acttcagcga tttcgctcca gtcattttta tcggtggcaa tgaagtccgc  34200
cagataaaga gctgtacgta atgatacgtt acgaagacga gatacattag ccttcatcca  34260
ggacagtgct tgataagtct cggcatcagt cagaccacgg ttttgcatca tatcagtgga  34320
caggataacg tcttcaacac ggaccataat ctcttcgttc gagtgaactc cgaggtctaa  34380
gtaaactgaa cgcgatacta aagcctggag gtgtggagca agtttagttc cacgctctaa  34440
ttcacggtcg atatcaacgt tggtgatgaa cacgatggtg ccttcgtatt cgaattcttt  34500
atcgatgttt ttatcatcga ggtaagaact tgaagtgctc cagcacacct tacgtttttc  34560
acctgtatcc aatgctgctt ttaacaggtt caggatatcc atatcagaga atacatcaac  34620
atcatcaata agaagaacac tattagggcc gcggttattc caaagctgct cgtaaagacc  34680
gattccacta atctttccgt tgattgattt atattcgata gtttcatttt cgtgggcatt  34740
ttgtaatgct ttatccaaag aatacgtttt accaatacct gcggcaccag agatgataag  34800
ggaacgaatt ttaccatcga tgattccgtt ggtcatcatg ttcattactt taaaacgttt  34860
gttaatgcga tgtttcattt cttcagcgga ttcagtaaca actgcaggag cttcagcacc  34920
ttccatttca acgtcacatt tgaacaccca tacaccacgt tcaacaccat caatctgtac  34980
gaataccttg ccgtcaccga ggtgagcttc tgattcatga attttattag ggaaccaggt  35040
tttacctgaa ctcatgaacg taccagagat tacattaccg cgatagatac ctttgttgat  35100
tttgatagtt aacattatat tctccatttc actcagtaga tttgataggt ccataataac  35160
atgctctacg agagtgtaaa ctctttttg cactaaaccc aaaaaaggcc cgaaggcctt  35220
tatcatttat aatacgagtt atggttttct aggtaaacct gctcaacgaa cttgtcccag  35280
aacttcatgt ctaccttctc aggcataccg ttcttagcgg cccagatagc attagtttcg  35340
acttcatcaa cgatagcttc aagttcggcc tgtacatctt taaaagcatg aagcccttgt  35400
ttgatttcaa ggataaacgg cgctgtacgt aaaggatatt gaaggtcacc agtttgatag  35460
atttccttca actgataacc agcacgataa gcatggctca gagctttcca gtcaatacct  35520
tcgttagctt cagccttacg agcacgttca ccatattcgg catcaagctt attcagagat  35580
tgcttgagct ctattaatga caaggtggtt tggtacttac gtcccaacac agtatagaac  35640
gtttgcgggc ctgttttctc atggttatga aatacccatt cacagaattc gttttcaggg  35700
agtcgatgtt tgatatcttc taccttagta cgacgttgtt tagtagaacc atcttcttgg  35760
taatcaatcc actgttcagg aatctggtta acgatagcca gtacaccacg caaagcagcc  35820
agacgagaac ccttaacacc atatttagaa gcttgcttac ggacgtaccc caaataggct  35880
ttcatgttag tcgtatagaa gcgtgaacga ttgtcttgaa taaatttcca tacatcaggt  35940
aaatcagatt taaccaccag ttcaggtgga gtgtggagca tatccagagc aacggtttcg  36000
ccatcagcag ccagtttaaa gaaatatttc aggctataaa gctcatggtc aacatcatct  36060
ttagtgtttt tggaagcagt gttattcgtg ttcaggttgg tatggttcat agccgtacct  36120
aacagaatat cacgcggatg tggaacaaag atttctttaa aatcgacatc agattccgga  36180
gtacttgttc cgtaaaggtg gctaccgaag tagcctttca taacagttct cattctttgc  36240
```

```
cctcgaagtg gattacagga cacatcttag atttacgagc tttaatgtat tgaataacga 36300
tgttttcttt aatttccttt ccttcgcgtt gggctttaat acgttcccat tccttttctt 36360
ctctacgcat atcataccat gagtgtaaat tcatcgcacc gaacgccaaa ccaatggata 36420
gtgcaataat gagagctatt gcaatcaacc ctaaaacaaa ccctagactc aacagaacag 36480
gggtacttaa tacaaagaaa tgctctaata caccagcgcc tgcaacagtt aatccaaaaa 36540
gcgtactacc agcaacaaca gcacaagcaa aacaagccca aaccattttc cagaaataag 36600
cacacaaaga gtgtggtcga gaatgacggt cataaaaacg atcgtgaagt ttagcgtgcc 36660
aagagtttgt attgataatc ataatatttt ccttaagagt tcatagttgg gataacagag 36720
ttcagataag agactaaaac ttttagttcg tctttagtaa ataccacttc actttcacca 36780
tcgtgtcttt gggtcaagga tagcaaatca cgaccctgat attgatacac ggttaattca 36840
gtatcgtaat ccagttcttc ttcgtcgcct tcaaaggttt cactagagcg aattacagca 36900
tcttgaccag ggactttcca ttcaacttcc ggcttgcatt cttcctggaa cagtttaaaa 36960
atacatttaa agaagttatc agaatcactg atgcttagac attccccgtc tgtttccaaa 37020
ttaaacccgt tgtcatggtt ataaatctgg gcccacatat catcgttaat atcaaataca 37080
cctctaaaac taccattaag atattggtgt ttgtccaaaa cctttaaatt ataaagcggc 37140
ttgatatctt ggatagtcag tacgatttta tcgtcttctt gtgaaagcac aattgcatta 37200
tcaactactt cagcagtcag gtcaccaaac agcccggatg tttcaataat cattttccgt 37260
tcctcatttc acattttgtt taataaaatt taacaactct ttaagagctt catcttcttc 37320
tttagaaagc ctgctgcatt cactagctgg gtaatcattg caaaacgcag tttcaaatct 37380
agcaactgta cctgcatagg cctcgataag ctcttcaagc tttaaatgct tttcttcggt 37440
tttcataaat caccggttat gttttaaaat actataaagc tcttcaactt ggcttgcatc 37500
cagataaatg acctcgtcat cttgttccag aacaatccca cctttaatga gattccattc 37560
caccacttca acagtcatat catcaccgga accggctaat gtttctggtt ctaaaacgat 37620
aataccgtct tcagaattac cactcgggtc atataacatt acagtttcct cgctaactgt 37680
gaaaagaata aaccaattaa aacaggccct acagccattg ttaaccaagc ccagggttct 37740
aagtaataaa tcatctcatg ctcctgtgcc aatagccatt atgctttcaa ctcattcaga 37800
taagcgacta atttttcttt agaaccattt aaatcacgct tacactgctc tattccagaa 37860
tatgaatagc cttcacaata ttcaacagcc aggtcattgg atgcgttttc aatgtgccgg 37920
gcgagtttaa ggatttgttc aatctgttca gtagttaaca tattatcacc agtatttgtt 37980
gatggtagaa attaattctt gggcttgggt agttttcagt ttacatccac aaccctttaa 38040
tgtgtcttta aggagccacg gttccttgag ctcgtccttt tctaggcgaa ttctgtatcc 38100
tcgataatcg gcaaagatac ttcggtcgtc gaatatctta atctcaagga tacggtcatt 38160
gatttcgtat tctaatgaaa ccgtagtact tgtaagtttc atactgttct cctcattagt 38220
tgataggtct atagtatcat gttcctagag gatgtaaaca cctaaacgaa aaaaggtccc 38280
accgaagtga gacctttgat tattctagcg tcagcaaata cttagtctgg taaaagacac 38340
cagtgatatc gtccaaagtc gactggaggg ccttaggaag ggtgtcatag attttatcag 38400
atgctttaag aagctcgtca agaaaatcta ccgggtcctt aggcaagtct gaagcagacg 38460
gtaatgatgc tttatattct ttgccactga atccaagata ttgctcacta aattggtcca 38520
gaggtccttg aacttctaca taatagaagt catacgcttt gtgtcttgca tagcttttgg 38580
tttctaaatg ggctgactta aaataggcta aagaaaccag tagccaacca atataagaat 38640
```

```
ccacttcaga ccctcgaccg ggtacgaaat cattgaactt catcttccac cttcattagt  38700
tttacataac gctctccgat ggcacgacct tcaattgagc acgcttctat agtccgacaa  38760
cttgaaatct tccaggaagc cgtaacatag gcccaatagt cttcggaggc ctttacgctg  38820
ggtctactca tttgcgcata aacaggcatc gcactactag caaatgcatc catcaattta  38880
tcattggtat catttgctag tgaaactgta gggcttaaac atcccgccat aaggatacaa  38940
gccgctgtac ggaaaatatc catacaaaag tcctttgttg ttttatacta tttgcctttc  39000
ggccttaacc gatagcgatt accaaaagct aaagctctac ggttagtatt attatttata  39060
gctttttaag cttacgacaa taagaataga acacgtcgtt aaaattatat tcaacccaat  39120
tcctctgtat aggcgaggta atggaaagca tataatgcgc tttaattaaa tccatcccat  39180
ttttattagg acattcttta ttattagcat tatacgtcgc tgctacaacc tctatctctc  39240
ttttgtaagc cacatcatcc atgataggcg aaagaacaat ataagaaata gccacagcga  39300
acgctagaat taaaatcttt gaatttaggt ccatagtacc ctcaactcgt tatttctatc  39360
cagtgcttcc tgcacaatga cacgtaagaa tcgttgccac ctatagaaac ttgggctccg  39420
tccttaattg cgataccatc ttggatacga gccgtcatag tagctttacg gccgcaatgg  39480
cacacacctt tgtactcaac gagtttatct gctgtagcga gtaattcagc agagccagga  39540
aacagtttac cctgaaaatc agttcttagt ccatagcaca taaccggaac attataattg  39600
tctactatct ttgccagttg ttttatctgt atcggttcta agaactgtgc ttcatccaca  39660
aatacacagt ggatatcttt ttgagattca gcccaacgat agaactcgta taggtccata  39720
tccggagtca ctgcattagc ctcttggcta atccctatac gagacgaaat gctatggctt  39780
gattctctat tgtctatcgc aggctttaaa aggagtacgc ccataccgcg ttctttgtag  39840
ttatgagcgg ctgttagcaa tgaagcagtc ttcccggaat tcattgccgc atagtgaaaa  39900
taaagttgag ccatattacc ttcttaaaga ctatttacat aagcaattaa ttcattttct  39960
ttctcatcaa accgactggc gaattcttcc tggtgttcgg catctatagg gccatattca  40020
tcataaaaag aatttgcttc tgcatgctca tctagaagtt catggataag ctcaaacaat  40080
ttatctttct gttctttact cagactcata accattgtac ctttaagcaa tattcttcta  40140
cgtgctgttt acgtttattt ttatctataa aagtatattc aacatattcg ccaatatacc  40200
atttatcagt gttgtgttga ctttttatag ggcatttagt tactcgggtt tcggtccagt  40260
gtcgaataat ttccgctttg tttttagggt caaacggatg cgggtaatgg gctttcataa  40320
tctaccacca ctaaattaat atcaggagta aacaaattaa tcaattggta aaccttgtcc  40380
caatcaccac cagcaatacc acaaccaatg cgaggaatat aaattcttgg tttaaacaaa  40440
agaccttttg cttgttgatt taattctatc atacagttta ctaaagcacc ataatcaaga  40500
ttagggcctg gttcgtattg ggtatataaa ttatagcaaa tttggccatt attacctgta  40560
gcttgagtaa acgtgccaag ttttgccaaa ttgcctaaat aagtagtttt atcgatagcg  40620
agaataggtg gataagcctt agccaattgt ccggctacac ctgaacccat tgtatggaaa  40680
cagttgcacc cgtgagcaac attattacct tgaagaaaca gggcgacgat atcgccctta  40740
atataatcaa taatcattta gagtttaatc ctcggttgta agagtcaacg agtctgtcta  40800
ccatagacgc gcacatttct ttgtactttt tatcagatgg aatacattca gtaacgttta  40860
gacgttgctc gtatctttta gaaagagttt tctctttcat tcggcgatgc tctacgtcat  40920
tctggccatc tttaaaagca gctgtgattt ttgaactgaa ttcgataatg cattcagtat  40980
```

-continued

```
tactcggatg acaataatct tttgctgtac gggtagcata ctcgacaatt gaattattac  41040
tatcatcaac ttgtgacgct aatactcccg gagcaatcaa cataagcgct atagtcatct  41100
gcttaatcat ttaatacacc gcctcaaaca tctttttaga ttttaggtaa ttggcctttt  41160
ctagaacttc agaagcatat ttactgcctg ctttgacgtt ccagcccgca ttataagaag  41220
caatcgcttt tctcaggtca cctttgtgaa catcaatcca ataagacagt tcaatgtagg  41280
cccaagaggc actgttctgt cgtttttgga ccatacggat tatttcttta tcagacatct  41340
tccaacctac ctgttgaaca cgacttctta acgtaggcaa gtaattttgg aacatgccat  41400
aagcatggtg cttatcttta tttaaacctt gattaattcc ggcggatgat tcctgccata  41460
gtaatccggc cataatatat cctaatcctt tttgattagg gttttctttg aactttcccg  41520
acttttggta ttgttcaccg aaagcatacg cataatgtaa attatcgagt tgttcattac  41580
tgaaagtagg ctctacgcta tgggcagaca tactaactgt caatagtaaa gtggctaata  41640
ctttttttcat gagacctcat tattaaagat agattacttt cgtgctggtt ttaccttcta  41700
aacgtttaga gttaacaaat gccatacgac atttaaggga atatccttta tcaggatgtt  41760
tacggtctac agtcatacct agccataagg ttttatcggt aatttcgaga cgcaatgggc  41820
gatacacttt accagggaca atttcggatt ctacatcagg cagaggttcc tggattaaga  41880
attcatggat ttctttaaca tggttatgga gttgcttgaa taaagcaaaa acgtattttt  41940
cgtcgatttc acgttggata gcacggtcca acaaatgatt agagtactta ataaagaagg  42000
ctgggactcc gctcttaatg gcggcttttt tgatggacgc attcagttca cggaattcgg  42060
tttcgaactg acgacgtaat ttgttgcggc ggatgaatac ttctgaatta atttctgaca  42120
ttttgtaatc tcctgtagtt gataggttta tagtatcacg tctacaggag atgtaaacag  42180
ctttattctt ggaatggggt aagttttcca acagctgaac aaatttctac cagtacaggg  42240
taaaactctt tcacttgttc aaggcgttgg gctgcatact gtacttcacc ttcttcgaga  42300
caagccattt ggtcgtcaag caagtatttg tggtagccag tacaggcttc accaatgata  42360
cgctggaaat cttgtaaact ttcaatttc atcagtattt ttcctcgggt tggaaaacgg  42420
aacgacacgc ccacatgctt gcttctttca gacggtcaat tgcattacga atctgggtga  42480
tgcgttcatg agcctggtcc agttcttgtt cagaaacctc ttcggtatct aagttcatat  42540
aatgagtaac atgttcttct tccagagctt taaacattaa cccaagacga acttctgcat  42600
ctttaatcgc gttcacttta ccgattttat cgtcggtatg cggtttataa ccctttatat  42660
cttcaatcat ttcacttcct cgccagttgc gatatcatat tctactaaac gaaggccatc  42720
atatccacca cgaacagaga tatatgtgct cggataaaca atttctttac cgttccattg  42780
cccaccatcc caacattcca taaagccttg ttcgccctgt tcgtggaacc agtcaacaaa  42840
catcttcaga gcttcatcag agccttcaat tgtcaattta gacatatttc ttccagtcag  42900
aaatcatatg aatctcttgg tcataagtca agagactacg agttataata cccttacaag  42960
gccctgagat gaactcgaga gtgaagtaag gaacctgttt cattaatcgg atgcttgggg  43020
catgacatct aaaacgagag cccttaaagg gccctgtcat gaatacatat tccaatgggt  43080
agaaataagc atattcgaaa tttgcagtaa ggtcctctct tcgaacctta cgtgagaaat  43140
aacagaactc aaaaagttct tcatcagtca tcattgcatt cctatcacaa agaacagagg  43200
acgcgcagtt tgattggttt cgacacatga tgcatgacag caatgttgca ccacctttat  43260
atgggcatca taaatcttat ccatattagg tgttttaaca ggctcatcaa ttatatacag  43320
aacccgtgaa agtgataatc cacggaattt gcatgcagtg ttaccaataa aactacgaac  43380
```

```
agaatcagtg tacaaacggt acttaatact ttctgtatgg ctattaaaat attcctttct  43440
gattgcagca gccgaaacat tagcatatgc cgtgttatta gacaaaataa caatagagcc  43500
gccattagct aaccattctg tggcaaaaat ggatactgct ttagttttac cggattggcg  43560
cccgccatca agttttaagg tgcagcattc tttaaacagg gtttgtgaat caggtacata  43620
aaacccacta ttacaaatgt gttctactct agcatcagaa tggtttgcaa aagcattcat  43680
cagggataga taactaccgg ttaaaaacgt tttcataatt gtctcttttt aagttgtggg  43740
gccattcctt ggcacattaa gtcgtccatg tatccgtatg taaacccttt accgcacttg  43800
ggctcgacct tattacaggt agggaaaggt ccatcactca gaggacgcga cgttcatgag  43860
gagagggccg gcttgccttt attagaaaga accagagcct ttaattgtgt tctggcgacc  43920
tttattttcc aattcagagt ggtcgatttc atatgcttgt gctacaccaa aggccttttt  43980
aactttagct aaagaacctt tagatgtaac aatattaaaa gtattacctt tggtaaaatc  44040
aaccaaatcc acttgtacac cctgcttgcc gaggcttgct acaatagcat caacatattg  44100
ttggtctaaa ttgccttgaa caccaatttg aaatgcctta ggagctttgg cttctgtgat  44160
aaattcttga taagttttca tattattcct taagttgata gaagtattct atcacggatt  44220
taattaagcg taaatagcct tgccataatg tttgtaccag gtaggacgct gtgcaatttt  44280
ttcgtccaaa cgagcctgag atatagcaat agaagcttcg tgtggagtat agtcaccacg  44340
gaattcctga ggaatatcac taatgtcctg gaccgtagtg tccttgatat taaaaccacg  44400
ttttaaacat tcggctataa gctcgatctg acgtttacgt aaaaattcaa gcttatcgta  44460
aaagaatgta acatgacctg taccaaggat aaaagtagga ctgattttga aatcacggac  44520
acgtttacca ttagcaacat gcttacgaac tgcaccgaaa acacgtggta attcacggta  44580
ctcagccatt aagtgttggt cagccaattc agatactaag gtaaggttga tacgagtcat  44640
tttagtgttc tccatgtttg tatgagaaca ctatatcaca gctatcgtaa aagtaaattg  44700
ttatttacct ttaattgctt tagctgcttc gatagccgct tgctgaaggt catccataga  44760
cataccgaac ttagaagcaa agttatcaat tttcttttcg acagaattca aaggcttggc  44820
ctgtttacct tcattagcgc cagggagagc gagaatacgc tctttgtcaa tataaaggct  44880
tacaagtttc ttacggtctt tatctggcaa atcatgaaat gaatgggcct ttttatttac  44940
ggcggcttct aatttacccg cacttactcg cgcttcggtg ataaattctt gataggtttt  45000
catatgtttc ctttaaatgt aaataggtcc gagtattcgc tttattaatt accacgggca  45060
gcattagcaa cggcgtaagc gtactgaata ttagcgtctt taaacgtacc tttagaggtg  45120
tctatttctg ccttaaagcc gcctttagcc ataacatcgg caaattcttt acggaaggcc  45180
attgcatcaa gacccttcca tgttgatttg tgcttggcaa attcaagacc ggcgaagttg  45240
accgccttag ccaatttatt atcaatagtc catttacctg ctttaggtac aaatacagga  45300
cctttctgtt tagagaacag ttttaaattc cagcgacgaa ggtcaccgtc agctttaaca  45360
aaagctgcgt ccaagttact agcaacaaca tcttggatat gggcaaattt aagtccatca  45420
gcttcaatat ttaggtcgtt acgccagcga agtccttccc aggcgaaagc tttaaagtcg  45480
gaagcttttg tagccaagta ccgttcaata ggagctgttt tagcgtcaaa accgtttcct  45540
gggttgtcaa cgccgtttcc tttgtaagtc cactcatctt tattaatgcc ttggaccttt  45600
cctacagaag cttcggcgat aaattcttta tacgttttca tacgggttcc ttaaaggtaa  45660
atattttaat tggtctgttc aagtaactgt agatatacta tcacaattct aggagatgta  45720
```

```
aacttattta taggtcttca tccaattctt gaacaaagcc gcgacgtctt tctctttaac  45780
gttcagttta atgtccaaca ttttaccacc cgctgctctg gtttggcgaa tcttagcagt  45840
accggtttcg ccattccact caacataata ctgtccagtg ttcattgcaa taccatcacc  45900
gtagtcttca tttttagaag tggtgaatgc tagcttcata gtcttagata cacgagcctg  45960
catgcctgtc tgcagagcgt tacgaacgcg aataacctga ggagtggcct gggtcaagtt  46020
ctcattcagt tcttcagtga actcttcaga ttcaaacatc gccaaaagtt ctttagatgc  46080
aggaattaca ttctctgcga taaattcatt ataagttttc atatgctttc caagtacctg  46140
ttttaaatgt tgaaatcacg cgcttagcac gattaggggt ttgtttatac caacgggatt  46200
gagccaggtt aactgccgca tcgttccaac gtttctgttg gagcatacgt aaagagttag  46260
tgaaccctgc tacacctgct tcacccattt ggaagaccat gttaattaaa gcacaacgac  46320
gaacttcgtc caatacattg taaacaggtt tcaatttagg attacgcaga atagctctac  46380
gagcattttc aaccgatcgg ttaaagagtt gttcggcttc agccatagta atacgaccat  46440
tacaaactcg gcccataagc ttatcaagtt cagcacgagc aacatcttta gatgggttct  46500
tggtaactaa ctggccaata ccaatagtcc aataaccttc agtgtcttta taaagattta  46560
aatcaagacc ttcgtcttga cgtaacatat caaaaaatatc cataatacct cctgagtata  46620
ggaggtattt atatcaaaag agcgaatcta aaaccttaaa catcgactta cccatgacat  46680
attcccattg cggacgttta atcaaggcga acgcatcgaa ttcaggaata gtacgaccat  46740
cagggaatgt atggtaagcc gtacatttgc aatccttgaa ctgctcgtgt tccacaggca  46800
ccgtatataa gaacagatgt agattcttat tgcttgaata tttgaactcg cctaggtctt  46860
tcaggaatgc aggatcgtat gctgtgaatc caatctcttc ttcggtttcg cgcattgccg  46920
cttgaatagg ctcttcgcct ggttcgacat gacctttagg aatgtcccat ttatgacgca  46980
tgttctctgg attacgagag cctgttacac gacccataac caattcttta tcggcagtca  47040
tgaacaaaat accggcagat agttctttca ctttcttact catcgtctcg ttcccatgat  47100
tgtttaaaga tatctcgtat aataatttca acacacgttt ctgttgacgg actttcacta  47160
tcagatattt ggaccatata atcagaaata ggtcggaaca tatccaagtc gctttctaaa  47220
tcttctttga ttttctcttc tgacgttccg gtatcatagg aatacagata agaatcacat  47280
gactcagatt taatataaat tgcaatactc atttacggca ttccttaata aaagagttta  47340
atgtattttt cttagtgata tcgtcatata ccttttttaac tttagaaata cgaaaaggta  47400
cttcgataac cgaggtccat aaaaatgatg cgataagacc taagatagca gcagacatcg  47460
ctgaagcgaa tacacaaata ggcaggtcat tatctgttgt caggaaaaac cctaggagtg  47520
ggaaaaataa tatacccatc caaacataga atctagaact caccaatttg tcgtattcat  47580
cactccaggc acggaagccg tattttttgc tataacaaat caatgggtct ggagtttgtt  47640
ctttatgtgg ttccgcttgc cagccgttta cgatatagcc cattttatat tcctcaatta  47700
aaagctgttt catttcggca gtacaacccg accaatctat cgtactagct ggaattcctt  47760
catcaccatc atcaatattt cgccaggact ttttaataac catattctca ccactcggga  47820
taataattcc ggcattttcc gaccgacgga tgaagtttgc atcaatgccc atacaccctg  47880
gttcataaag ggccattacc agccctccat agggaattcc agatatactt gagcattaac  47940
acggatttca ttagtaatct ttttaacacg gtcggtatta cgagacacac gaccaaacca  48000
gcgccaaccg ttacttactg cacgagaacc cgtatgccat gtctgccaat caaactggag  48060
caacgtgcgg tcaggagcat cccacttggt taattcattg gactcaattt tttccagaac  48120
```

```
ttctttatgc cactggcgat agataagttc gccttcagga atctggctaa attgcgcagt  48180
tccggttgca aaatgggtag gacacacatc agcgttaaca agaccaagaa tatgttcaga  48240
atggtaacga ggattatcat aatcaggttg ccctgcggta ataaagtgtt ggccaaccgg  48300
aatatccgga cgtggtacat catcatggtg gaagcctgga attgcagggt accagccggg  48360
cattaacatg tgtacacggg aatcaaatac aatatcaggc ccacattgcc aatcttcagg  48420
caggttttca ataaagctac gagtaatagg accaccgtgt ttatgagcaa aataagcatc  48480
acaattaaag aacataggct catttttaat catatcatta ctgatatctt gagcaaaatt  48540
acctactata gaagctttgg aattaaaagt ttttggacca ttcataatat tttcctcact  48600
tactttttgt tgaaaaagta cattttacct ttaggggata aggatacacg aagtgcgtta  48660
ccaataccaa ctgaacattt aaccaggtca gcagatttta attcaccgaa tgcttgacga  48720
aggtcaccgt cacgagtgtt aaccatcagg catttagcac cagctgcacg aacttcgttt  48780
aacatgttga ttgcttggtt agaaagtttc attttattct ccatttcact ctgttgtttt  48840
gataggtcta tagtatcaca cctatagacc ttgtaaacaa ttttatgcaa ttatttttcg  48900
aaaggacgaa ttaaatgttg gttacgctta aaccgttcaa tgtagtcgtt ttcacctaaa  48960
gtcttgtaca tattaaccac agcttggtag ttttcccagg cgtactcacg gaaccaacct  49020
gaagtgattg aggtgcacac tttctcaaga gccatataga aacttaatga tggtgaaata  49080
ttgaagtcat taggaacctg tgaacgttct agtgccagga cacaagtttc ttcatacaca  49140
ccagctaatt taatagcttc aggcaaagct tcaaacttct cacgagaagt catgacttca  49200
gaaccttcct tcatataaaa ggtatatgca gggcgtcctg ccaatgctac tgcttcgtgg  49260
atggagtcat ggtccagcgt ataaatggta tcattaaaga atgatgattt gttaacgtct  49320
aatttagggt gagaatagct caacgtttct ttttgacgtt gcagcataat ttcctggagt  49380
tcttcgttca gggtcacgcc tttattacga aggtatttga tgtgggacat agttttcaag  49440
aagaacggat tattcttcag gaaacgatga gaggttttga tagccagaca gatatcaggg  49500
gttgcccaat agaaaccagt aagacggtcc tttttaatat gattttcagc atatttcagg  49560
agacgatagc ttgaggtgta gtcttcatct tggagctcac cagtgatttc tcgtacgtta  49620
gtcagggcac ggacgatata agcttcgaaa taggtttctt tgccgttgta catgcattta  49680
aaagcctgga catcagggtt atccacagga acatgagcac cgaacatacg tgctttaaag  49740
tggttccatg agccttggtc ggcaatgaaa tcccaatcag aatttttgat atacttattt  49800
tcaatcagac cagcgtggtg cagtgcacga gaaccaataa ctaacatcat aatattttcc  49860
tcagtaaact taaatttcag caacgtaagt gttatgcaat tcccacatat catcggaatt  49920
actctcaacg ataggaatta tctcattaga aatttcttct gcataagggt cgttgataca  49980
gtgggcatct tcaaaacgaa caccgtaatc agacttctta taagcaaagc cataaatctt  50040
tttaaacctg gcacgagtaa tgcgtaccgg ttcattagac ttatcggaca tcggagcata  50100
ataccacata tgttctcctc atgtttgtgt agggtaatag taacacgtat ttttagagtt  50160
gtacatcact tctgcaatat tctaaaaata atttatcgtt gtctactgta tcccaacgac  50220
gccaagatgg gttccagacc aaagcgttgt caccacaatc attgagctta aaatggtcgt  50280
agtacatagc tatacgtcta gtttcgtcac cagagaaccc cagtataggc tcgccatggg  50340
tgtgatacat atgatggtgc attgagaggt cgcatttgta aaacatctca cgtttaccac  50400
gaacgaacaa gaaggcttgc ccattcatat agaattcttt atctgttttc aaaagatatt  50460
```

```
tgaatactga atctttatgc ataagtcctc ctaccacatc catgtggtta aattattttc  50520
ctaacgaaac acgagtaggt tttttaccaa aatagtcttc gtaagaacca tctaaacggc  50580
ccgctttaga ccgacaatat gaatcgtact ttttgtaata agtcatctca gtattataac  50640
gtgggtgtct atcggccata ataatactta gtggccaacc tttggcataa tcgcgaagac  50700
tgtttatttt acgaatgtat cgttttttca attttagcat gagcttgggt accagatttt  50760
accatcggca cgagcaacga aggtacgacc agcttcttcg ccataacaag agctattcag  50820
ccaatcttcg agacgaactt caccgtcata atcgtcgagc tcaacaccaa aatcctgagc  50880
agaagccata tcttttactt tcttatacag tgcagccagt tcaagtgccg ctttttctaa  50940
ttcattaata tcagacattt ttatttcctt agcaagacat agaagaagta aaccagaaac  51000
catcaccatc aggaatgccg taatcatcac ggacccattc gtaatcatca tattccgggt  51060
tctttggaga aatgtattgt ccacgaccag aaacatggaa ctcttcacct gtttcgtcag  51120
ccacggactg gcctttacgt actaattcac ggatttgttt ttcaatttca tcaatagtca  51180
ttttatttcc ttagcattcg taagaggagg acacccaaga ggtaccacta atagtaatac  51240
aaccgttata aagcgtgata tgacgttcca ggtcacgagc gccatcgata tagatatcag  51300
cttcttcgcg ttcttcttta caaatctgga taacgttttc aatagctgcg gctgcagtac  51360
ggattgcaca atctagttca cgagacataa taattcctta acattcagaa gaagaggata  51420
cccatccacc attttctagg ctggtagtgt aatcatgttg gtttacaata gcgtactgag  51480
cttcaccgta ttcttcccag tgggcaaggt cggctttcag ggcgccagga gaataatagt  51540
caccgcccat accgcgagca gggtatatat taaaatgagt ctcatatttg ttagcaattt  51600
cctcagcacg acgaatagct ttatgaatat catttactgc ttcagccagt tctttatttt  51660
tatggtaatc attcatcata gcgtttcctt agcacattgc cgaagaggag acccaagcac  51720
caactgtaac gacaccgttt tcaacttcac cgccattgtt ttcaatttca tctttaaacc  51780
actgggagca ttcataaccg acaggataat atgtacggcc tgaaccataa tcaccggtgc  51840
cgaattggat accatactta tcggcaatag cttcgcattc atgttcgatg gcatctactt  51900
tattcagaag agcatagata gccttttctg cagacagcgc gctgttgtat tcagggattt  51960
caatttcaat tttattcatg atttacattc cttaataaag gtttcaaggt cattacgttt  52020
agtttgtttt acatactcat tataattagc catctctaaa gcatatctct tacggatggg  52080
agcattcaaa gcgtttgtat ggcaaatatc atacacaaca gggataaaat aagccacgac  52140
agcaggagcg attatcatat agaaacccat ctcaataggc atgattcctt cgattgccgc  52200
cataaccgtg gtcattacca gaccaaccag accaccgagc ataccggtcg caattcccat  52260
aaataaggaa atagcaatat catattcagc caattgataa acatgtgatg aaagactagg  52320
ccgttccatt ttgaacctct ttagcgtatt cacggcattc agcaataaaa cgattaagct  52380
tccgttgttg tttacgactt tctaatgtgt actcagtagt taagatacca agctcggctt  52440
tatcataatt tttaatatca gagtaagatg ggcgacggtc aaccattcca aatacatcac  52500
cattttctaa agctacatag catactaaat ggtaatcatc gtctgccata ttaagaagca  52560
cacaatcagc gctctcgttt aaagaatata ctgaataacg tagtccagcg aattccactc  52620
gttgaatagc cagatttacg tcaataattt ccaaagcatc ttcaaaagaa aggtcttcag  52680
ctaaagcaaa aataaaaggt aatttggtag tatcgccacg gctagatgtt ctgcttaaga  52740
aatcgtttga atagcctagg tcttggcgaa ttctataaag aactgaattg gtttcatggg  52800
aaagaccact atttttaaac caatcaatat ttgatataag gttatcatat aaactcataa  52860
```

```
tattctcctc tcctccaaat agggagaccg aagtctcccg gtaacattac ttaagtgaat  52920
taatgtagtc ttcgatatca gcagaagtcg tatccattcc aacttgcggg cctttaaacg  52980
tttctacacg catcagggtg tcttcaatat caatcttagt cagtgcagcg atttcaacaa  53040
catcatcggc agtagcaata cccagggcag ccatattacg agtttcacga atgtactcaa  53100
gcttaaccgc tagttcctgg cgagagtcat caagttcctt gaccttaagc ttaatttcat  53160
tacgcatttc aacataatca tcggctttct tacgaagttg agtagctgta cgacgataaa  53220
ggagacccag tttagcatgt acctggacat cagcgccttc ggcaatcagt ttacgaattt  53280
cacgttcttt agaagcagcg agctggtctt tttcattagc caatgcacga atacgttttt  53340
cttcattcac agacttaaca tgagcagtct ggagttcagt gattttatca atcagagtag  53400
aagcagcttt ggtgtattgg tcttcgattg acaggttctg agccattgcg gtgcccagtt  53460
tagaacgaat gaattcaacg attttcttta aagtgttcat agtatttcct tcagttggtt  53520
aacgttttgt aatccatgag gacattatac cctgtcctct gaggtttgta aacattttat  53580
ttcatttttg cgaggcaaat ttcattggct tcccattgag cttgcttaat aatagctttg  53640
gatacaggag ccctttggcc ataagttttt gacgttgaga gaacaatatg tttgtttgct  53700
tcattatgcc agccccatga tttttcgccg tgagtacctt taactacagc tgacacctca  53760
acagagcaac caccatcaga aatcttggtt tcgacaaccc attcatttct ctcagcagct  53820
tcaatttcta atctagtttt ttcttcatac atcgcggccc aatcagtttt tgccaagttg  53880
aaagtaagag ctttctctag ttctttggca tatttttgtt gttcaggtgt taatgaatta  53940
tacaactctt gcatttcttt atcttcgata ttcattatgt tctcctcaaa ttatgggctc  54000
ataatatctt aatcatgagc ccgtgtaaac gttttatttc atattattga aataattttc  54060
tgcatcaaaa tcattaccat ggtaaacttt ggtagacgat ttggcgtaac cttcagctga  54120
gaacatatta atcacaactt taattgtata ccactgtcca tcttcattac ccattactgc  54180
ataggtttca tacaccgggt gttcaggacc gataacttta atatcgttaa cagtagcacc  54240
aaattcttca ggaacgcatt tcataaagaa attaaacact tcaccataat tatccatttt  54300
actctccttc acactgttgt tttgataggt ctatagtatc atgttctacg aaagagtaaa  54360
catctttttt aaacttttta gaaacaaaaa aaggcccaac ctttcggaag ggcctagaat  54420
cagttcttgt agaaccggaa tgggtttatg tggaaggcta acatagcctt agggatttta  54480
cgagacaaaa gactcttaag tttccaacca cagtatacac gaaggtaaaa ggtaatccca  54540
cctactttaa gatacggaac tgaagcaaag actccccatg cttcgtcatt ccacatccat  54600
aaccatccat gatgagcttt atcaggagaa ccggatttaa cgtcaggatt accacgataa  54660
tggaattctg agctacaatc gcgtccaagt ttatggtaag caaagttata agctttattt  54720
cgccatagcc aagctaccct ctggagataa acaccgcccg gcattttcct gattttagcc  54780
caacgtttaa tatgaccttt gtcaccgtca attggattat cgtatgtcat catccaatca  54840
aagccataag gcaatttacc ggtctttttta ttatggaaag gaactacaaa aggcgcaagg  54900
ataacggcca gaaccataga gatgaaatcc agtggaacca acagaaccca actcaaatat  54960
tttaaaagtt tcatatattt ctctaagtta accaaaaaag ccccagacgg ggctttcgtt  55020
atttgatttg tttagcagac cagatacggt ctttgatgat tttctgaata tcttcaacat  55080
actctaagtc gtgagcatgt ggattatctt tgaagctatg tgctcgtgcc agtttctggc  55140
cttctgtttt gattactaaa agctctttaa gaattgcttc atacttagaa ataattcctt  55200
```

tggcgatatt tttttcttga gcggctttag ggtccgcttt tgacgcaggt gctttacctg 55260
tagctttctg gaacaattca cctgatgcag ctaggctttt aaaaactcgg ctaacagtat 55320
tggcattagt aaaaccttcg gctttaaaat ctttaataaa acggaaacgt tcttcatcag 55380
aggcgtcttt gtaagaatat ttacctgctt gaattgctgc aatcgcagcg gcttttacat 55440
ctgaactaga ttgttcagtc aaaaattcat tgtaagtttt cattattatt tcctaagtta 55500
attaacttat ctatttatta tgccaaaaag ccccaacctt tcggaagggg ctatgccttg 55560
cggcaacctt gtcggggttc cacctgctag gcaagtgttt gtacgaaacg ccaggattcg 55620
aacccggtta ttaagtagtt gacgctactc aatattttta aaaggccata tctcgaccat 55680
atccgaacgt tccgtcaaaa acgctactcg gcttacggca aagatatttc ctcgaatcga 55740
taattctgtg cgccgtttct gctgtgatgt aaggggacat caacaaatca taaagattta 55800
ttaatgtcag tccttaaaca gggaacatca gtccgacgac ttaccggtag cgacccggtt 55860
tcttgtttgt tgcgccggtg aatgctggta atcagtcttc atacgacggc ttgactatat 55920
aatagtcttc atttggtatc ccgccctggg atcgaaccag gaccgcaaac ttagaaggat 55980
cgtatgctat ccattacacc agcgggacgt agttggtgac ccagaccaga tttgaactgg 56040
taacctttcc cttatgaggg gactgctgct aaccattgag ctacagggcc ttaaatcaaa 56100
ctacaaatcc agcaggagca ttatcatctt taatcatatg ctgaattgta tgataagtca 56160
tttcttctgg agcaaccaaa taggctgcga cgttaaccag tggaattctt ttgggcttag 56220
tgaatgtgga atccgctatt gacataaagg ctttgccgtc tcgttcaact tcaccaaatt 56280
gacattcata tgaaatagaa caacgtttgg tagtggttgt cttggttgcc gggtcataaa 56340
aagctaattt taatactaac ataaacacct caaataaaat taagtaaagt aagtttgatt 56400
aatagacctt gtctattatg aaaggctctt tgagggaaga acctttggta atagagggtt 56460
acttaataat gttagagtaa taatatcaca ttactcttaa agcatattac tatttttagg 56520
aatagtctgg tcaaatttga ttcattgtgg ccacatatta atgtaatcaa gtttaataga 56580
agcaatcttc aaaggatttt taaagatgtc gtattcgatc aatccgtttt cagttgcggt 56640
gtagaaagta aagttaacag aattataacg gcgaccatta acttttagtt taacgtcgct 56700
tgaactacgg ccaatattaa cctgttggac atcaagcaca gcacctttgc caaagttgcg 56760
aatcagtagc tctgctgcaa cctggtctga attatatcca ttctctggat tagtaacctt 56820
aacgtataac atttaaccct cgtctacaat agtatgggta ttggcattaa caatctgcca 56880
ccagtcaaaa cgatcggagc cgtaacgagg ctttttctca ttttcgttaa taatatcacg 56940
tagttcgtct tcagaaaatg ctttagcgat taaatcggta tagccaccac gtgggtaata 57000
gttgtcacct gcgaacagaa ggaaatttac tttaccagaa ggaacatatg cttccttagg 57060
atacttgttt cctgcttggt ctaccacttc aatataacgg taaggaatat cggtactttc 57120
aacccattgc caagctgcag caggggattc aaaagcatct acacctaaac ggttatcttc 57180
atctttagac ggattatttt cataatccgc atatacataa tattcaatgt tcattattca 57240
cctttagaga ttttatccat aacgaaagaa attgaaccaa ttaagaatgc cactactaaa 57300
gagattatat tctcggaagt tgaaagcata tcgagcatga atcctgcaaa catactaaag 57360
ccaaaagcag taacagcggc cagtgcagta acatttctaa ttaattcaca acgtttcatt 57420
ttattctcca atcactcatt tgttttgata gggctatagt accatcacta aagcccgttg 57480
taaacaatta ttttaaataa attgcatact ttttataacc ggctgtttcg tgacgtagcc 57540
ctttttcatt agcaaaacgt tcaatattgt taatttgatt ctggtcaagt tctgaagtat 57600

```
caaatacaaa aaagtttcgc ttattgccta aagttacgtg attagtcaaa tcgatgttat  57660
agagatgatt tatattatca atcatggtct taacagattt gttaattttt acttcttcat  57720
taagaataga ttcagcgata aattcttggt atgatttcat tttattcagc accagcggct  57780
ttcaaaagtt ttttaagatt ggcagtgcct tgagcagaaa atgtgacttt gccgtctttt  57840
tcgccgatgc tcccggtcaa tttagcgagc ttatcactag ggactttttt aaaatcagcc  57900
aatgtaccgt caaaggtttt tgtaacaacc ggcagttggt cttcttgttt tttagcttcg  57960
gtaataaatt cttgataagt tttcattttt atttccatgt ggttagtttg ttttgatagg  58020
tctatagtat catgcctata gaccttgtaa acaacttttt taaattattt tagccatgaa  58080
gaattttcag agacccagct atctatatct gattgtgggc caaagaagta ggcaacccca  58140
ttagataact ctcctgaaag ccaatttata cctttcaggc tttctttaaa ttcttcagga  58200
gtacaagaaa cctctattgc caccgaagag gctggttcca ttgcttccgt taagaattcg  58260
ttgtaggttt tcattttaaa tcctcggccc agtcgagctt caagggttct ttatattctc  58320
tgtctaaaac aacaggaatc tggacatctc cactaaaggt aagaggtcct acattataag  58380
acaatgtgat atgaggggta taatcatcaa aatcgtgcgt agcacctaag gtacgagcat  58440
actgatggcg gcatttaaga tactctgaat tgagaaccaa taccaggaca ggagaatcac  58500
cgtgtttcca cacttcaaga tgtcctgacg aagcaacttc aaaacttccg gatgcaacgg  58560
tgtatggaac gttgactctt gaatagcaga ttgtagaatg gaatttttca cgaggaactg  58620
gattaggaac ctttaaagtg cgctgaaggt tttccagcgc atctaaagtt aattcagaga  58680
attttgcagc aacgtataga ccttgagcaa aatcttcggt tttcattatt cttcgtcaga  58740
agcttctgga accagggcat taacggcatc gatgatatca tcaattttaa tctgctcgcc  58800
ttcaatacca actgcgtggc agattttacc aagggcttcc tgaaggatac gagattcctg  58860
ctgcgcctga gcaacagcat cctgggtatc aagaatacgg gatttcagaa gaacgatttc  58920
ggactgcagt ttctgttcgg tagtttgttc agacattttt atttcctaat aatttatcaa  58980
tagtagtgta tagttcagaa agagtgccgt tattttcaac aacaacgtca ccaggtaaaa  59040
ttggcagacc cgcttcagtg atgtgcgagt cttgtacttg accggtttca gagcgaacta  59100
catgaataat cgtagcaccc atcgctctga gcgaatcaat ttcatgtgtt tgacgaacat  59160
caggtacgac atagtatttc gcatcagagt atattttatc aaaatagtct aaagcgaaca  59220
acttaaccca atacatctta tcaaattggt taacaataat atcagtccca agggtctgca  59280
tgagacgacg tactgaccaa ttgttatttt tatttattac ttcaaacagt tggtcttttg  59340
tttcttcaga cagatactgg actggggtaa gaccataatg atatgcggta cgaacatcca  59400
ttcctggaat aggaaggata ttattcagtt tgacaatagc attttcaaag atatcaatca  59460
catcatatgg ttttaaagga aggatttctt cacggtcgta accgatacct tcaaaacagt  59520
tgaaatccag tttaggcata taactacggt cgaatacagg gtcatcagag atgtattcat  59580
aggcttcagc cagatacttt ttaataggac ctgcgagctg aaattttacc gaatccatat  59640
tttcgattac atagttagca acggtatcct taccgctacg tttgattcct acaattgata  59700
ttagtttcat tattttctca tagatggatg catagacata cgagccacac gttgttcggc  59760
atacgaatca atttgtggac gacctgtaac tattgtacca tctatttcta cagcaaacga  59820
tttgaagttg aatgttgctg tggcgattat tgctgggtca gaatcctctt tataagagta  59880
ctggatttcc gagaggtcag atggccaacc gccatagtaa tgaatgctca ttacgatttt  59940
```

-continued

```
ctgtttgtta ttatcaagga tatggagcgt aattgcttca ggtaagcctt taggatgcca  60000
agcttcggat tcatgggtta cgtagttgtt taatgacaac atccacttat aaacgtcaag  60060
ccatgatttc aattcacggt ctacaagaaa gttcacgatc aatgggtcga attctacagt  60120
agaacctggc agcttagcac gatgtatgcc ctgggtcgat cctgggacgt ctgagatcgg  60180
aatatggata ccgggtagtg ttacatcttg tacgttcaat ttgaatgact gtgtcattcc  60240
tgagtcacta acctctaaga taaagttggt ggtgttagtt tggttaaata aaccgttcat  60300
aaggttccta tattgcttaa gtcccagaca gtgtataatg gtcctaggtc tgttccattc  60360
aataactggc tgggataata gattatgaat tcttccatac tttctgagcc gagtaacgct  60420
tgcctttaga catgaattgc tgaagtggaa gcatgaccac attggcccaa tcagatggtt  60480
ttatctctac taaaggtccc ttaatatttc cagggatata agccttaatc atcacgtctg  60540
caccagcgaa tccttttacc ttactccaat cgatttttaa tttagtcgag ttagtaatgg  60600
taggcgtact cgcgtattgc ttcagcaatt cttccagaaa ttgttggcgt gctttaggcg  60660
ggatatagtg taagttcagc ccgtacatta aattatgctt acctaaccca agataaatga  60720
ttaaaggata tttgtcccag tacggtaggg tatccttgtg tttagcgtca tagatataag  60780
cataaagctt accaggagat ggtttagata cctggtgtcc acgaattcct ttctttaatg  60840
tttctgtaaa ccatttagct gatttattat ttacagcagc gccttcgtta gcaatcttat  60900
cacgaatact ctttctaaaa ctattcacca aaattaattg acgttcggct ttggttaatt  60960
tattgccagg tttattctga agtttttcaa cctgtacagc agttttaatt cggctcgagt  61020
atcgagacat cgcagatgta aagctagaat acttgatgcc tttatcttca gcgaatttct  61080
tagccgagac acctttagcc ttagcgttgg catattcaac gcctaaagtt atccattgtt  61140
gttctgaacg agtgggcttg gaaccttttg tggtttcagt agcctcattg atgtaggaaa  61200
atatactcat cctttccatc ctaatttttt cagtgaatgt tcggtaatca atctaaaggt  61260
gatacccatt ttatctgctg tagatttagc tgctttccac ttatcggtat taacggacca  61320
agtataatgt tcgttgatat atctcttttt agcagccgta gtcattttaa caggcaccgc  61380
aggagcatgg gtttctttaa aaggtttgac ttcaaaaaag aattgttgac ctgtatcaaa  61440
tttaacccag aagtccataa aatatcgtct tttctttcct tcagcattgc aaaagtaagg  61500
aatgactacc tcttccgaat tccactggac tacattaggg tggttgtcaa gccaacgcat  61560
aaaccatgct tcccaagagg aacgatattg gattttcttc cagtcacctt tatatttttg  61620
taagtttgta ggtttaaatt tccctgagta agccatagtc gcctccttat aaatattaat  61680
attatttata ctcggaggcc ctatgctctt ctcatttttc gatcctatcg attacgaatc  61740
aaaaacagtc aagccagatt ccggctcatt aacaaatgcc gatgtactga gcgtgccgat  61800
gactgatata tttagaaatt ataaagaata tttcgataaa gtggctaaaa attatacact  61860
aaagacttat tatatcaatg gggcccctcg tccagaagaa ttggctaatc aactttatgg  61920
caacgtccaa ttatattggg ttttattgat gtgcaataat acatatgacc cctattacgg  61980
gtggattaca ggtcaagaag ttgcatatca agcggcaatc caaagatatt ctactgcagg  62040
cggtaatcaa gttctttatc atgttaatga aaagggtgag aaattctgga atcttgttaa  62100
cactccagaa aacccgtata cttggtatga taaaggcgat acagaaaaac gctatcctca  62160
atatgagggc cctttggctg cagtagatat ttacgaggat gctattcgta aaaatgaata  62220
taagcgcgaa ataaagattg tagaccctaa tgatattgag tcctttattt ctgcccttat  62280
tcgcgaaatg gagaaagccc tctaatgatt aacatgtctg ataatgtaag ttggttcgtc  62340
```

```
ggtgtagttg aagaccgaat ggacccgctc aaacaaggcc gagtacgcgt gcgcgtatgg  62400
ggtatgcatc cctatgaaaa ggtacaaggc cctgtaaaag gtcttcgtac agaagattta  62460
ccatggatgt cggtattaat gcctacatct tctgcctctg tttctggtat acaaaccgct  62520
atgactggta tggtccctgg tacacaagtt tatggccact ttcttgataa gtggaaatta  62580
aacggactcg tccttggtac atacggttcc gcttcaaaac aaaaagcaaa ccctaatgaa  62640
ggctttagtg acccgacagg tcaatatcca ctttatttag gtaatgatgc cgctgcacta  62700
aaccgaggtg gtgaagttgg atatgatgcc acttctaacg taatacaaga tgcaaacact  62760
gatgtaggta ttaatcctga tggtttagat ttaagtcaag tcaaacctga tgataatcct  62820
aatttcacaa tagaaaacat gcttcatcgt gatgaagggc ttagactgaa ggtatattgg  62880
gacaccgaag gatatcctac tataggtata ggccacctta ttacgccaca acctattaga  62940
gatatgggtc ggataaacaa aatattatct aatcaggtag gacgagaagt taaaggtaac  63000
cctggtgcaa tatcaatgga tgaggcttct aaattattcc aagaagacct taaaaaagtc  63060
caaaacgata taggtaggca tagtgttgtg ggtcctgttt acaataaaga aaaccgttca  63120
agacaaatgg ctcttgaaaa catggctttc caaatggggt taggcgggct tgctaaattc  63180
cgtggaatgc ttagtgcaat gttaataggc gattataaaa aggcatttga agaagcccgt  63240
aattcagtgt ggtttaacca aactaaagga cgtgcatcaa gggtatcaat gattatcctt  63300
acaggtaata tggaatcata cggtattatg gccccaaaag aaaggtcatt taaagggcgt  63360
tcgtatagaa tgattcaaac ctttgctgct cctgcaaatt cagacccttc cgacccatgg  63420
actccagaag acacaaggat tctttttaaa gaacctgatt ctagttataa aggtgaatac  63480
ccgtatgtcc aaaccatgca gactgaaggt ggacacgtcc aagaatttga taacacccca  63540
gggcaagaac gttatcgttt aatccatcct acaggtagtt atgaagaagt tgctcctgac  63600
ggacgtaaaa cttctaagac ggtagccgat ggatattata tgacccaagg cgattctaat  63660
acttatgttg gtggtaataa taaagtcaat ataggtggtg atgaaacata ttataatatg  63720
gcaaacgtac gccgtcaaac tgacgggtcc gaaagcatcc atattcgcgg taatgaaact  63780
aaaactgtag aaggtgatgg gacccttatt gttaaaggga acgttacagt tattgtcgag  63840
ggtaatgctg atataactgt taaaggtgat gcaaaaacat tagttgaagg caaccatgac  63900
tatacagtaa atggaaacgt taaatggtct gtaaatggaa acgttgatat gactgttgca  63960
ggcaattggt ccgagactat ggcttcaatg agttctattg catctggaca atatactatt  64020
gatggtagcc gtgtggatgt ggggttataa tgaatttagt ttataaaatg acctttgaat  64080
ctcgtcttaa aaataaaact cctccctatt attatgtagg gagtaaaact aattgttttt  64140
tcgatggtaa gaatataata gatgaagatg gaaaaattta taaaacttct agtaaagtta  64200
aggaacttaa ggattcgttt ttattagaat ctcctaaaat agaaatactt tatttccaat  64260
tagtaggatt tgaaagtatt accgagatag aagagaaatt tcaaagagct atagatttag  64320
aaagttggca caacgaatat tttaacttgt catatgctaa tggcgaattt acaacatatg  64380
gtaagatttg gactgttaaa gaaaaatccg aaatgtcttc tataatgaaa gatagcgaag  64440
cccataaaaa aggccgtgtc gttataagtt ttaaaaatac aggtcgcaaa ttatccaagg  64500
aagattctat acgaaaatcc gatttgatga aagctctatg gtctgatatt gaatataaag  64560
aacgcctttc aaaagcccac tcaaagcctt tatcaacatc acataaggaa agtatacaat  64620
ttgcatggaa aaacgaatct ttaagggcgg aaaagggtaa agtaacaaag aaaaattcta  64680
```

ggtctaaagg cgtttggata tatgctaatg aaatttacaa agtttttaaa gaaaaccctt 64740
ctataggaga acccacattt agaaagacct gtgtaagctt gggattacct gatagtagtt 64800
atgtcgccat taggcgagct ttttctaata acgattttga atttcttgat gtggagattt 64860
acaatggcta atatcctacc tatgagcact gatttaggag actccataga aggagctagt 64920
atagatatat tttttacagc tcaattagaa acaaacgaaa cattagtcga aataaatata 64980
actgaatatg aggccacccc tggcattatt gtcgatggcg cccatttata tggaacctac 65040
gaatcggtat ttggattctc tgaggatgca ttaaaatacc gattaaacga cgaatttaaa 65100
actgccggtt catggaaaga tttgccagag gacgagagca ctcaattgta cctctggaaa 65160
gcccctagca atctccagaa gaccttttct tatactgtca cattaatcta tgactttcag 65220
gaagagacgt caggaggtga tacagggaac tcaggcggta gtaactctag agctggcgca 65280
gaaaccgacc cacctcccgc tcctgtaaga aaaaccctta ctaaggttta taccaaggtt 65340
atagtgggta attggagcaa atgggctaat caattaagag aatatgtata tgcgaggcca 65400
taatgtcagg cttaagttac aaccaatgcg taacggcagg tcatgaagca tggcctccta 65460
cagtaataaa tgccacccaa ggtaaagtat ttacaggtgg tattcctgta ttagttgcag 65520
gagaccctat tacagaacat acagaaatta aaaaaccata tgaaacccac ggtggggtaa 65580
cccaacctag aacatcaaag gtatatgtta caggcaaaaa ggctgtccag atggcagacc 65640
ctatttcatg cggagataca gtcgcacaag cctcatccaa agtattcata aaataggaat 65700
taaaatggct actcctacga attaccaatt aacaagaacc gttaacgcta tcccaaaagt 65760
atttgtggga gctacgtttg aagaaattaa aaagaatatt atagactggc tttctagcca 65820
ggacgaattt aaggattatg atttcgttgg ttctcgaatg aatatcctta ttgatatgct 65880
tgcttataat accctttata tgcaacagtt tgctaacacc gctttatacg aatcttttat 65940
aggaacagca aaccttcgtt cttcggttgt ccaggctgca caggataacg gatatcttcc 66000
tagttctaaa tcagcggcaa aaactaccgt aatgcttacg tgtactcaag cccttaatga 66060
aaaaaatatt cgtattccaa gaggtactaa attcctggct tatgcccgtg atacgtccgc 66120
cgacccatat tcttttgtga caactgataa cgttattgca gtgcgagacg ttaataatca 66180
gtattggcct attgtttctc tggctcaagg acgtattatt cgtaccgaac ttaaatacga 66240
ccctaaaact cctattctta ttcgtgaccc ggatattgat agacaagaag ttaaacttta 66300
tgttgatggc gcagaatgga ttaactggac caataaatca atggttcacg ctggtagcac 66360
ctctaccatt tactatatgc gcgaaaccgt agatggtaat actgaattct tctttggtga 66420
gggtgaagcc gagaaatctg ttgcaggcgg agtattagaa gctaattata tcggcggtct 66480
aaaacctgtt aaagattcta ccattgttat agaatacctt cgtacagatg gcgaagttgc 66540
aaacggtgct gtcgacttca gttatgccga ctccttggct tatattactg tagaaaaaat 66600
tactgaaaac tataacgatg accctgatta tgttggtgcc gatggtgggg gtgaccctga 66660
agatattgaa cgtattcgcg aattggctgt agttaagcgt gaagcccaga tgcgtgctgt 66720
aacaggaacc gactacgata cattcgtgtc cgagcgtttt ggttctattg tacaagcagt 66780
acaaaccttt acagacccaa ataaacccgg ttatgctttt gtcaccatta aacctaaatc 66840
agggttatat ttgacggcag tacaacgtga agacgttcag aactatctaa aagaatttaa 66900
cttagcccct attaccgctt ctgttatttc tcctgattat ttgttcttaa agcataaaat 66960
taaggtatcg tatgccttga ataaattaca ggaatctgaa cagtggctat cggctcaaat 67020
tctttctcag atagaccgtt attatattaa cgaagtagaa atttttaacc atggattcgc 67080
taagtcaaaa atgctgactt atattgataa tgccgaccat agtattttag gctcctctgc 67140
taccataaca atggttcgtg aggtattgaa ctttttcaaa acccctgaat caggtattaa 67200
atactataat caatacacta accgttctgt ggtttctagt gaatttgagt ttgtccctac 67260
tatcgtttct gaagacagtc cggcgtataa tgtcagaatt gccgctacag ataaagacga 67320
acgtggtgat ggtaaaatgg ttattggtcc tttccgtcca ggagatgtaa ttgaaaacca 67380
atatattaaa ccatatacag gaaatgactt tgataaaatg cctgctcctg cggaccaatc 67440
cgtttattac gttataggtg aaattgatta ttattcagat ttcattttct gggacattgc 67500
ggctattggc ttgacctccg atcgttttga agtccaatct attgaacttt atgcaggtcc 67560
tggccaagat aacgtctttg ctaaagacgg tactttaatc gtatttgaag atgacctacg 67620
ccctcaatac actaccattg aattagaacc tattacaata taagcctctt cggaggcttt 67680
gaggagattt aatgtctgta caagcgcctt cagttactag tctgagaatc gataaactct 67740
cggctaacca cgttagcatt ctctgggatg acgtaggcgc caatttctat tatttcgtag 67800
aactggccca aaccaaagat gcaggtgaaa ctatacctga tgataagtta ttttggagaa 67860
acttaggtta taccccggac aataactggt tcgaggaaag atttatatct cctaattcgt 67920
tttataaaat gcgtgtagca gttgcggccc aaggctttga acagtctgaa tgggaataca 67980
ccgaagaatt tgaaacattt tctactaacg catatacctt cgagcatatg cgtgaattta 68040
ctttatccaa taaattcatt gaagaaaaat ttactaaaaa taaccagagt tacgtggatt 68100
ttaatagtga tgccattatg gcttctatga tgaccgaaga ttttacttgg actccggcat 68160
attcacacct ttcttcaatt tccaattatg tattaaaggc cgaccgcttc cacgagattc 68220
aaggaagtat ccaagccgtt tgtaaagacc ctaatcgttc tattttaatg gaacttggtg 68280
gggtgcttta ccttttagaa cgattccaga acacggccaa ggtatctaat gacaaggccc 68340
agaactggca ttatatccgt ttgtttaatg atagagtagg taatccggtt tcacgtacgg 68400
ctcattatca aacagacaca acaacttatg ttctaggtta cgaccgtata ttttacggac 68460
gtaaatcaag tgatattcgt tggtctgctg atgatgtacg ttttagctca caagacgtga 68520
catttgccaa aattggtagt gatatcgacc tggacttcga aatcgaaata tttggttctt 68580
atgcccgttt accattagct atttctacta tcgcagaagc tatgtgtgct tcggatgatt 68640
ttatttacgt tgcggctcgt gacagagttt ataaagcaaa aactactgat gcccctattg 68700
acaccgaccc gggctctcct acttacggtg agaaaatatt tgaaagtggc tattcgacca 68760
taaccggtaa ccctaaagca gtttgttata aattggattc tatccaagga aatacctttg 68820
ccttaattac gggtgaagtt aaagaagaaa gaatggaccc tactaaagaa gaaaacgtgg 68880
ttgattctga atctaaaggt gtttattggt tggatgtcga aactgataca tggacccgag 68940
tatttggtaa tactgaagaa gagagacgtc gtattgagca tgggtatact agcatgtcta 69000
ccgacggcga agaaatattc tttagttcca gtaacttcaa atatgaagta gaagttgata 69060
acgaattacc tttagaatac cctattgtgg cctcagcggt aaaatatgtt aaggatgaac 69120
agtggattca tgataaacac tatctgatga tgagctttag agctaacagt aaatcagatt 69180
ttaaagaatt caaacccggt cgaatggcct attatgctga accgttcttt agttggtcta 69240
gacgcgatgg gacccgttct tggattacca caagtaatca tgcaatggtt gtttataatg 69300
acgcattata tcagaaaatt attgatttaa acagcggttc ttctcctgaa cgtattatcc 69360
gtgaaatttg ggataaaggc ttttgtaccg taacatgccc taatatcgaa ttcaatggat 69420

```
ttaaaaaata ctcttcaggt ataatgattc acaaatcatc aggtgaattg gttggatatt  69480
tcgagttcga ctaccgagtt cgagatgaag tccgtgttat ttggaagcct aaagaaataa  69540
tgtttacggc tgaacttcaa aaccaagagc atgaaattcc atggacccct aaagaggaaa  69600
ccggtgaaca agaccctgat ttgcgtcctt tattagttaa aatggttcct gatagttatt  69660
tgcttcaaga ttctaacttt gaaaaattct gcgaatatta cctccagttt attagtgatg  69720
gctccggcac ccattataat aatctattaa atcttattcg taaccaatac cctagagaag  69780
aagatgcgtg ggaatactta tggtctgaaa tctataaacg caatatctat ttgtctaaag  69840
aaaaacgcga cgaagtagtt cgtttcttcc aagcaagaca atcggatttc tggtctacaa  69900
aaggtaccga agcttcatat aaattcctgt ttaaattgct ttataacgaa gatgttgaaa  69960
ttgacatcga gtccaagaac tcgattgaat atgatatcat cgtagaatcc gacaatatca  70020
gtgaagatat cgtaggccaa acgatttata cccctacagg aagaagtaat gttacttata  70080
tagaacgaaa ttacaaagat ggtaaattgc aatggcgttt aaccattcac aatcttttag  70140
gccggtttat agttggacaa gagattaaat ctgaacgcac ctcatttaaa ggtatgatag  70200
tgcagggtgt acgcggtaaa gaattgttaa gtaacaatat cgattatatt aaccgtaacc  70260
gttcttatta tgttatgact attaaatcca acctccctac ttctcgatat cgtaatgacg  70320
tgttgagatt tgttcatcct gtaggatttg gttttatagg gattacgttg ctttctatgt  70380
ttgttaatgt tggtttgaca ttaaagcaca cggaaaccat tattaatata cttaagaact  70440
ataagtggga ctcaggtctt ccgtccgagt ggtacgatag agttgctgta atcggatttg  70500
atggtaatat agaaagagac cctagaacag gacttccggt ttataacgtt ggacctaaag  70560
caggcgaacc gttccctatt cctgatgatt atgatgcaga aaatgatttc tctgtattcc  70620
aaggtcaatt acctcatgaa cgtattaaaa agcatagtcc tttatttgac caaagtgcag  70680
taacattttc aaaatggcgt gctttagttg atgaccgact taaagctgat attggaaacc  70740
ctagagaccc gcaagaccca actcaggtaa aaattgatga ttaattcaac agtaatatac  70800
cgttctattg ttacttctaa atttagaacg gaaaagatgt ataactttta cagaacaatc  70860
ggtgatggtg aagaccagaa cacgatgtat gtatctttcg ggagagccca accatgggct  70920
cctaacgaaa acgacccagg ctttgctcca ccttatcctg tagatgattc tgagggcgta  70980
gaagacgtct ggacaaacat gatgggttgt gttaaggttt ataagagtat gttggattgt  71040
gttgttcctc gcaaagactg ggcgataccc tcttatccta accctttcac tttccaaatt  71100
ggtgaaattg tagtggcgaa tagccaacct caaaaccgta ctgatgttgg tgcaggttgg  71160
atggtttatc gttgtgtgga cgtgcctgaa tcaggagcat gttctatttt gtcccttgat  71220
aataaaaccg agtgtattaa acttggtggt aaatggaccg ctaacgttcc ttcagttaaa  71280
gccccggcag gacaaggcga tacggaaggt atggtagaca ctggtgatgg ttacctttgg  71340
gaatacottt atgagattcc acctgatgta agtatcaacc gctgcactaa cgaatatatt  71400
gtggttccat ggccagaaga aattgccgaa gaccctgaac gttggggata cgagaataac  71460
cttacttggc agcaagatga ttatggttta atttatcgta ttaaagccaa tactattcgt  71520
tttaaagcat tcttagattc agtttacttc cctgaattta gtctgcctgg taacaaaggg  71580
tttagacagc tttcgataat ttctaacccg ttagaagcta aagctcatcc atccgatccg  71640
atcattaaag ctgaaaaaga gtactatgat gttatagacc tctcccgcca ttcaggtgaa  71700
atgatttata tggaaaaccg tcctccggtt attcgttcca tggaccaaac agaagaaatt  71760
aacattatct tcgaattcta ataagggccg caaggccctt tcgggggtat aaatacatta  71820
```

```
tatcaataat gaggcatacc tatgattaag caaactggta agttactaat tgacgtcggt  71880
gagattggta atgccagcac cggcgacatc ttatatgacg gtggtgttaa actgaacacc  71940
gacttaaaca acatctataa tacttttggc gaccaacgta aaacagccct tacaggcgaa  72000
actactggtc aaaaattaca tgccactgga tactatcaaa aattcggtga taccgaccaa  72060
gcaggttctg ttgatttagg ctctttggtg gatgtcgatg cttctaccgg ttctatagtt  72120
ttaacaactg taaaaggagc tgtgggcgaa ggtattgaaa taattaactc taatggaagt  72180
atttcagcta ccaactatct tgaaatccgt atattggatt cgtttttgaa ccatcctaca  72240
tcaagcttaa gaatagtaac tccttataca cgggttcttt tatggtgtgt aagtgatata  72300
aacggtatag ctgtatggga ttattctatt gagagtatgt ttggtgacaa acgagtgcca  72360
ttaaatagaa catacaacat ttccaacgta cctagagatg tccaggtggt ttattcaggt  72420
caatattctt tagttaagct tttagttacg gcagtaaatg ccaatgaaac cgtttataaa  72480
gcttctgaat atcttttgtt tatggataac caagctaaaa aaatatattc tacggaatac  72540
gctgttatcc gtcgtggaca agccaccgat gaagacgaaa tttacaatct cgattttaaa  72600
tttgatacat ccaactatat agtggctacg gcatcatctg aaacccctat gagattagca  72660
attaaagtcg tagataccca aactattgga gtcccagtat aatgaaacaa gaattaaaaa  72720
taggccaggc cgttgacgat ggctccggag attacctgcg cgcaggtggt ctaaaaatca  72780
ataataactt taatgagtta tattatcaat taggtgatgg agataatcca cacgctgctg  72840
gtgcctggaa acaatattct actgcagacg gtcctttact taatgctgtt atgggtcata  72900
gctatacatt gaatacccaa ggtggaagga ttaacgttca acttcctaaa ggcaccccat  72960
cagaatataa ctttgtaatt cgtttacgtg acgtttattc ttcttggcaa gctaaccctg  73020
tgactattat accggcccca ggtgatacaa ttaaaggttc cgctgtacag gttgaaatag  73080
ctcgtaattt tgctgacctt gaacttgttt actgtgcccc cggacgttgg gaatatgttg  73140
agaacaaaca agttaaccgt atcccaaata acgacctcgc tactgtagca actaaacagt  73200
ttattgccac tgaaggtcaa actgatttct tggatatttt cccaggtcta acctataata  73260
tttcaagtct tagcgttatc caacgtggta acaacttgtt ctacggtgtg gatgatatat  73320
ttgatgaagc tacttctgag tttggtagcc caggcgcaaa cccaggcgaa ttggttgaat  73380
tgaacggtaa agatatccgt ttgaaatatc cttgtgaagc tggcgatacg gtaattatta  73440
aatcgtataa cgatggattg gcccaatggc gtagttctta taatcgtcgc gatattacta  73500
ttttagatac gacccttacc catgaaacca cagttaatgg ttctaaagta gtattagacc  73560
tttctaccgt acagactatt acatcagcag aattaaacgt ttctcctaca agccctatta  73620
accctaatgc ttgtcaggta atgcttaata gtactttatt gcatcaagcc ggtactgcag  73680
gattccctgc tttttattgt gaaggtgttg atacggatga tgcaggcctt tgtgcagatt  73740
caggcggggt atggacccaa tctaaatctg attatatttt gaatatagca gatgatgaca  73800
aaatcgagtc atttgaattt ggacgtaaac tggaacatgg cgatatcctt actgtaattt  73860
ggtataataa cgatatcggt accactatga ctattgacga gattttagat acaacaaacg  73920
atatctatat ttctcaaggt ccttcggtat ctttgactgg ccaggttcgt attactgatg  73980
tagataatcc attttctcct aactttgaac ctgtagcgga atccgaagtt tccattaata  74040
ctgccgcagt gatgtttgat ttgttccacc ctattggaac gatttatgag aacaccgtga  74100
accctaataa ccctgcaact tatatgggta tgggtagttg gaaaagactg tctgatagtt  74160
```

-continued

```
tccttgtagg ttggtctccg gatgctgact cgttgttcaa tgcaaacaat aatgatttag  74220
actctggtgg tgttcctaaa tctactgccg gcgggacggg cggttctcat aatatttcca  74280
ttaaatatga aaacgttcct gaacttaata cagacgacaa ggtattagtt gccgatgata  74340
acggccctat tgttattggc ggatgtttgg tagacccgga tgcccaaggc ccggcttata  74400
caaaatatcg tgaagataaa gctacgataa acaaacagca atctacaacg cctattccta  74460
ttggcacttt gcctccatat acaaccgttt atcgctgggt gaggattgcg taatgacttt  74520
aacagaaatg aaaagcgggt taaaatcccg ccttgccgac tttttagaat tttcttttac  74580
aactaatcaa cctgccgcag tggcaggtca acgccctatt ggtggtccat cggcaaacca  74640
aacccaaaaa ggtgtttatt accctacggt ccaaagtgct attgatgata ttgctttccg  74700
tgcagaactt cctgtcaatg cagttgtaac tactactgaa aacagggccc ctggctttat  74760
tcagcaatct gataaattaa ctttctccgg ctccatttct tccggtggcg aattaggcga  74820
tacggttatt attaaggtat tcggtttgcc tgttgaagtt attgtgggtg attcttcggt  74880
cctggttgct tctaaagtta acgatgcttt tataagcgct attgctgata gttatatttt  74940
ggcagaaacg tctatcgacc ctctagacca gtctacttta aacattaaat ataacgacta  75000
ccaaaaccat atttttgagc catttaaaca agcaggatgc accatttctc agactatagt  75060
tcaagagcct cgtgcgggtt atggatactg ggaatattta ggttctacta cagaatctat  75120
gacaggtgga accgtaaatg gaacaacaac cttatatcac tataagcgag taagttaatg  75180
tctacaaata cactaaaaca cataagtgat aaatcagaat ttaaaacatt cgaccctacc  75240
gggtcgaatt ttgacccctc tattactaat gtccaggatg cattggcgtc tatttccgct  75300
ataggtgtta caggtaatat accttcggct tctgaaacag aacaaggtat tattagatta  75360
gcgacccaac aagaagttat tgatggtact gatactttct ctgcggtaac tccggccact  75420
ttaaagggtc gtttagatat tcctactcaa gcaacagaaa cttatgtagg tatcacccgt  75480
tatgctacta acgctgaagc cattgccgga acagaaaccc aggctgcaat cgtagcatca  75540
tctttgaaag ctactataga ttatacattc accaatcgtt tagccacaga gaacactaca  75600
ggcgtactca agatttcaac cctgccggct gctctagcgg gtacagacga tacgacggca  75660
atgacaccgc ttaaaaccgc tcaggcaatt ggtgccgcta catccgcgtt gccgacttat  75720
gccagtgcta ctcaaactgt tgaaggtatt gttagaatcg caacaaatgc tgaagtggca  75780
aatggtacat tgaccaacgg tgtagcgatt tctccttccg gattaaaatc tttaacttct  75840
acccaaggac gagctggtat tattagatta gccactccac aagaagcttc ggctggcagc  75900
gattctaata tagctttatc tccttcaact cttctttctc gtactggtac taccggaagg  75960
ttgggtgttg ttaaattatc gaccacggtc ggttctggtg atgggaatac ggcattggca  76020
tataatgcta acgttatttc taccacaggc ggcaccatta atggtacttt aaacgttaac  76080
ggtactttac gtcgcaatgg gcgtgatgtt gttactatcg accaattaaa agattctgtc  76140
cctatcggta ctattgttat gtggggaggc cagattaata atatccctgc aggttgggct  76200
gtttgtgatg gtggtaactc tggtgaacaa gggttccgaa atgtagttgg tagtaaatgg  76260
ggttcaaccg gagcacgtcc tgacttccgt ggattatatc ctagaggtgc aaaccagact  76320
aatgacggcg gattaaaaga atgggacgct aacgtcagaa ttagagatgc taaaggtaat  76380
gatgccaaag gtaaacctaa attaggcgta ggttgtggtt catatggcca tggtactgta  76440
caagcccagc agcttcgttt ccataaacat gcaggtggct ttggtgaaca ggataactcc  76500
ggtgcatttg gtaataccgt tcgttctaac tttgccggca ctcgtaaagg gctggactgg  76560
```

```
gataaccgtt cctactttac aaacgaaggg tatgaaattg acggttacgg ttcacgagat  76620
tcaagaacta ctctaaacag tgaagggttg gttggtaacg aaaaccgtcc ttggactatg  76680
tccatcctat tcattattaa agttgcttaa ggaaataaaa tgattgacaa actgagtatt  76740
aaagaacttc cgtttgtcga tggtgtacct gatgcatccc aagagcgtat ccgttggata  76800
cgcaatggcg aatgtattga aggagccacg actaaatacg gtcacgacgg taatttgaat  76860
gcccctgctt taggagtaca aaccaacgta gttagattag aagaaaacag tatagcttct  76920
aaagacaaaa ttaacgagct tgtggataac gttaatttga ttaatgaagc cctagatatt  76980
tctactgata cgggtgttat tcaacaaatt gaaaagaacc gagttgatat actggctgtg  77040
gatgtaaagg cttccgaaac taaacaagaa ttaggtgact taaccgttaa ttttaatttt  77100
ttagaagaag atgtaggtta ttacgacccg tctttagatg gcccatatct caccgtcaga  77160
gaaaatataa atcttcttaa atctgaaatt ggacattatg cgaaccagga tataaacagc  77220
caaccgcttc ctccaggtga aacttctgaa gccaccggca tgaaacgtcg cattatggat  77280
aataccagtg ctattgtcga ccattcacaa cgtatagata cccttgaaaa gaattacgaa  77340
gattctgatg tagggcaact tggtcttaag cttaacgaaa ttcgtgaaga actgggtcct  77400
catattgata ccgtaggtaa acaaccagcg tataccagga tttctgctct tgaaactgct  77460
gctgaaagct ttaacgaatc aatagattct atcaaaacca gtataggttt taataaaggc  77520
cctattgata caagagtaac cacgctggaa actaaaactt ccactttaga aaacactgtt  77580
aataccggtt tggttcctag agttactgca gtggaaaccg ctatcggtac tgctgatgcc  77640
cctacttcta ttaacggtag attaggcggc ttacgcaccg atgttaatga actaaaaact  77700
atagtaggtg ctagttcatc agaagggctt cgtttccagg tttctgatat tgaccgtaaa  77760
atcggtgctg atgtaagtcc ggcggcagga acaattaata agcgtttgaa cgaccttaca  77820
actcaaggta atacctcagc ctctactatt caggacttgc aggccgaaat tggtaataac  77880
caaacgggta ttaaaggttc tattcttaaa attaccaacc aaattgaagg aacaaaccct  77940
aacggtagta ctgtagaaga acgagggtta ataaactctg ttaaaggcct tgaagctcaa  78000
atgcctacta aattgagtga cgcccctgct gatggtaaat tgtacggacg taaagatgcg  78060
gcatgggctg aagttgttga tgcaggtacg gaaatagctg cagtaaaagc ttctttagta  78120
gttactgatg gtgaggttga tgatttagga actcgtttaa ctgcggctga aggtaaaatc  78180
actgcactag aaactgagtt ggctaaacgc cctcctgttg ctcctgtggc tgacggactt  78240
ccgtatgttc tggttgataa cgcatgggta ctattgtcag attttgtgac tttaaaccca  78300
gcaccataat aaaagggctt cggccctttt ttgctataaa tacggttatt agaggaataa  78360
aacatggcaa gcgaatcatt taaccctaag caactcaagg acgctattct gcgccgcctg  78420
ggtgcgccga ttacaaatat tgaagtaact acagaccaag tatacgattg catccagcga  78480
gccctagagc tctacggtga gtaccattat aacgggtata acaaaggcta tcaggctttt  78540
tatatcggtc atgacgatga agaaaaattc cgtaatgggg tatttgacct taaaggccgt  78600
aatatatttg cagtgacaca aattttgaga accaatgtag gttctttaac atctatggac  78660
gggcaagcaa cttatccgtg gtttactgat tttgtattag gcttagcagg tattaatggc  78720
gggttagggt cttcgtgtaa cagtttcgga cctaatgcct tcggtgctga ccttggttat  78780
tttacacaat taatgcaata tcgttctatg atgcaggacc ttttggttcc actacctgat  78840
tattggtata acgatgccac cgaacagttg aaggtaatgg gtaactttgt taaaggtgat  78900
```

```
tttattgtaa ttgaagttta tactcgctct tttaatggag tggattctat ggtaggaaat  78960
actgtaggat atggttatgc ttcagcttgt ggtgaagatg catggagccc aggtgctatt  79020
tgggataatc cggcgcgtcg tatttctggt atgcgtgtag gtgaggacct tggtcttcaa  79080
gatggtgcat ataataaccg ttgggttaaa gattatgcta ctgcattggt taaagaagtc  79140
aatggtaata ttttagccaa acaccaaggc atgcaacttg caggtggaac cactgtagat  79200
ggtattcgat tgattgaaga ggctcgttta gaaaaagaac gtcttcgtga agaattagat  79260
ttactcgacc caccaacacc tattttaatt ggataattat ggctactttc gattcgagtt  79320
tattcgctaa gctagaagat aatactggct atgctaacac gaacgaaact gaaataatga  79380
accctttcgt caacttttat aagcatgaga atacccaaac attggctgat gctttagttg  79440
ctgagtctat tcaaatgcgt ggtattgagc tttattatat accacgtgaa tacgttaaac  79500
cagaccagct atttggcgaa gaccttcaga acaaatttac taaagcctgg aagtttgcag  79560
gatatttgga ttcctttgaa ggttattccg gtgacaatac ttatttcagt aagttcggta  79620
tgatggttaa tgatgaagta acaatcacaa ttaaccctaa cctttttaaa catcaatgca  79680
atggcactga acctgtttca ggcgacctga tttattttcc aatggacaat agcctattcg  79740
aaattaactg ggtacaacct tacgacccgt tctatcaagt gggtgctaac gtccaacgtc  79800
gaatcactgc taccaagttc atttacaacg gtgaagaact tcgtcctgaa ttacagagaa  79860
atgaaggtat taatattcct gaattcagtg agcttgattt aatgcctgtt aagaatatcg  79920
acgggttggc tgatatctct gacattcaat acgaagaggt caatgagatt aatgctgaag  79980
cggctgaatt cgtacatcct tatgttgtaa ttaatggacg aggagaggat gttcctccta  80040
cagcatttga tgatgctttt ttagatgatt aaataataca tggcgcatgg tgcgccattt  80100
taggaggttt gatgtttgga cattggtata atagttcgct acgtcgctat attgttttga  80160
tgggtgattt attttcccat gttcaagtgg cgcgtcaaag agaagataca gggcttaaat  80220
ttattaaagt tcctattacg tatgcttcta aagaaagatt tatggcaaat ttgggtaaat  80280
ggactgctgt tcaaaatatt ccaaacccta atatgtctcc taaagaacga gctgaacaaa  80340
aggctaaagt ggaaacagtt ctcccacgta tgaaccttca aatggttgat atgctttata  80400
actcacaata taaaacggct cttcagaata gaacacaaat tcaatttgag aatggagacc  80460
ctcgtaaacg ggttagccaa tattctccta ctccggttaa aatgattttc gaactgggta  80520
tttacactag aacccaagat gatatgttcc aaattgtgga acagattatg ccttatttcc  80580
aacctcactt taatacaaca atcactgaac tctatacaaa cgagattaaa tttgaccgtg  80640
atattcgtat tgtgttccag tctattgcta tggatgaaca acttgaaggt gataccgctt  80700
cacgtcgtcg tttagaatgg tctatgatgt ttgaggttaa cgggtggtta tatcctccgg  80760
ttaaagaaat ggaaggcgaa attaaaacca tttatcttga tttctttgct aactcaaagg  80820
aactcgctcc tgaaggtaat ttcgaatcag ttgatagtga agtggttccg agaggtgtag  80880
aacaaacaga atgggatgga agttccgttc aaacatattc acaagatatt ccagtgcctg  80940
tcgagccagc gcctccagca ccaaggagaa acccatgagc gatttagata tcaataaatt  81000
aatggatatt accgacctcc ctggcctgac cggggaggaa gttacagcct atgaaccaat  81060
agtattaaaa gaagtggaaa gtaatccaca gaaccgtact cctgatttag aagacgacta  81120
ttctgtggtt cgtagaaacc tccattttca acagcaaatg ttaatggatg ccggtaaaat  81180
atttttagaa gttgctaaga acgctgaatc accacgtcat atggaagtat ttgccacatt  81240
aatgggccag atgactacca ctaacaaaga gcttttaaaa cttcataaag aaatgaaaga  81300
```

tattaccgct gaacaaatcg gtactaaagg tggagagcct aatcaaacta atatccaaaa 81360
tgccactatt tttatgggtt caccaaccga tttaatggat gaagtgggag acgcttatga 81420
ggcccaggaa gaacgtgaga aggtaattaa tggaacaacc agttaacgta ttaagcgatg 81480
accatccact aaacgaaggc aagactacag tcattaagcc gccgggttcg cttgaacgta 81540
aaacagaaga aggtatcaat tggattaaat cccaatggga tgacaaatgg taccctgaaa 81600
agtttagtga ttatttacgt atccataaaa tagttaaaat tcctaataac ggggaccgtc 81660
caaacgaatt ccaaacgttt aaagataaaa tgaataaacg tacccgttat atggggcttc 81720
ctaaccttaa acgagctaat ataaaaactc aatggtctcg tgaaatggtt agtgaatgga 81780
agaaatgtcg tgatgacatt gtctattttg ctgaaactta ttgtgcaatt acacacattg 81840
actatggtac aattaaggtc caacttcgtg attaccagcg tgatatgctt aaaatcatga 81900
gcaagaaccg tatgacgact tgtaacctgt ctcgccagtt aggtaaaaca accgtcgttg 81960
ctatattcct tgcccacttt gtttgcttta acaaagataa ggccgttggt attctggcgc 82020
ataaaggctc gatgtctgcc gaagtacttg accgtaccaa acaagctatt gaattgcttc 82080
cggatttctt acagcctggt atcgtagaat ggaacaaagg ctcaattgag ttggataatg 82140
gtagttctat tggtgcttat gcttcatctc ctgacgccgt gcgtggtaac tccttcgcaa 82200
tgatttatat tgacgaatgt gcgtttatcc ctaactttct agattcatgg ctggctattc 82260
aaccggttat ttcatctggt cgtcgttcca agattattat tacaaccact ccaaatgggt 82320
taaaccactt ctatgatatt tggactgctg cagtagaagg taaatcaggc tttgcaccat 82380
atacggccat ctggaactca gttaaggaac gtctttataa cgatgcagat atatttgacg 82440
atggttggga atggtcctct cagacaatct ctgcgtcctc tttagcgcaa tttagacagg 82500
agcactgtgc agagttccaa ggcacaagtg gtacattgat tagtggtatg aaattggcta 82560
ttatggattg ggtggaagtt actcctgaaa acggatactt ttatcgtttc catgaaccgg 82620
accctacaca caaatatatt gcttcattag actgctcaga gggtcgtgga caggactatc 82680
acgctttaca tattattgac gttacaacgg atgaatggga gcaggttgct gttttgcatt 82740
ctaatgaaat atcccatatg attctccctg acatagtgta taaatatcta atggagtata 82800
atgaggctcc tgtatacatt gaacttaaca gcacaggtgt ctcggttgcc aaatctcttt 82860
atatggacct tgaatacgaa aacgttattt gtgattcgat gcaagattta ggtatgaaac 82920
aaaccagacg aactaaacct gttggctgtt ctacattaaa agaccttatt gaaaaggaca 82980
aattaaaact taatcataag caaacaataa tggaattccg taccttagt cagaacaagt 83040
tatcttgggc tgcagaagat ggtttccatg atgaccttgt gatgagttta gtgatttttg 83100
cctggttaac gacccagcaa aaatttgccg acttcattga ccgagacgaa atgcgattag 83160
catctgaagt ctttagtcgt gagttggaag atatgaacga agaatataat ccagtcgttt 83220
tcgtggatgc tggcgataat tcatatgaat attcaccgtt gaatcatggt atttcgttta 83280
tataaataac aataaagcat aaccaagagg attcaaaatg tctttattat caccgggcat 83340
tgagctcaaa gaaacgtccg tacagagtac tgtcgttcgt aacgcaacgg gtcgtgcagc 83400
gctggttggt aaattccagt ggggccctgc tttccaggta actcaaatta ctaacgaagt 83460
tgaactggtg gatttgtttg gaggtcctaa caacgaagtg gcagattatt ttatgtctgg 83520
tatgaacttc ctccagtatg gtaatgacct tcgtacagtt cgtgttgtta accgtgaatt 83580
cgctaaaaac gcatctccta ttgcaggcaa tatagaaacc actattacta cggctggttc 83640

```
taactatgcg gtaggcgata aaattaatat caagcacaac caaaccgttg ttgaatctga  83700
aggtcgtgtg acttctgtag atacggatgg taaaattctt tccgtgttta tcccatcagc  83760
aaaaattatt gcttatgcac gttctcttaa ccaatatcca gaccttgggc ctgcatggac  83820
ggctgaagtt acttccgctt cttctggtgt ttctggtact attaccgtag gtaaaattgt  83880
aaccgattcc ggtattctgt tgactgaagc agagaacagt gaagaagcta ttacttccct  83940
ggaattccaa gcatctctta agaaatttgc tatgccaggc gtagtggccc tttatccagg  84000
cgaaattggt agtactctgg aagttgaaat tgtttctaaa gcggcttatg atgccggttc  84060
tactaaaatg ctggatattt atccaggtgg tggctcccgt gcttctattg ctaaggcggt  84120
atttaattac ggtcctcaaa cagatgacca atatgctatt attgttcgtc gtgatggggc  84180
tatcgtagaa tctgtcgtac tttctaccaa agaaggcgaa aaagacgttt acggtaataa  84240
catttatctt gatgactatt tcgctaaagg tacttccaat tacatctatg caacttctct  84300
gaactggcca aaaggcttca gtggtatcat taatctgatg ggtggtgttt ctgccaacga  84360
taaagttacc gcaggcgatt tgatgcaggg ttgggatttg tttgccgacc gtgaagcact  84420
ccatattaac cttttgattg ctggtgctgt tgctggtgaa ggtgatgaag ttgcttctac  84480
cgtccagaaa cacgttgtta gtattgctga tgaacgtcag gattgcttag cctttatttc  84540
tcctcctaag ggtcttttgg ttaacgttcc attgactcgc gcagtagata accttattga  84600
ctggcgtacc ggtgcaggta ctttcgatgc caacaatatg aacattagca ccacttatgc  84660
tgctattgac ggtaactata aataccagta tgacaaatat aatgacgtaa accgttgggt  84720
gcctctggca gctgatatgg ccggtttgtg tgcacgtact gatgatgttt ctcagccttg  84780
gatgtctcca gctggttata accgtggcca gattcttaac gttctgaaat tggcaattga  84840
acctcgtcaa gctcaacgtg accgcatgta ccaagaagct attaacccag ttgttggttt  84900
tgctggtggt gatggtttcg tattgtttgg tgataagact gcaactaaag ttccatctcc  84960
gatggaccat attaacgttc gccgtctgtt caacatgctt aagaaaaata tcggtgatgc  85020
ctctaaatat aaactgtttg aattgaacga caacttcact cgttcaagct tccgtatgga  85080
agtttctcag tacttagatg gtattaaggc acttggtggg atttatgaag gacgtgtggt  85140
ttgtgatact acagtgaaca cccctgcggt tatcgaccgt aatgagttta ttgctaatat  85200
ctacgttaaa ccttctcgtt ctattaacta catcacgttg aacttcgttg caacgagcac  85260
tggtgctgat tttgatgaat tgattggacc tttagtataa tctattatcc caggctgtaa  85320
tataaagaac ctaaaaccat tataccatga gtttggttac agcgtacatc acgtagaaat  85380
gcgcctggga ttgattattc tctcagaata tgatttatca actgtataac taaaaacgtc  85440
gcaggcgcaa tcctgcgact ttctggtata taaatataag tatgattact aatactctat  85500
ttgaaatacc tataacaaat cgtaacgttt ctgcttttaa aaatcttggc tatcaagtta  85560
aaagtgggag ctcctattta ataaaattag aagactgtcc tggaaaaatt gctgttacgt  85620
gtaaatgtga taaatgtgga atttattata ctgtaacaaa agggcgactt aatgaaacca  85680
attctaagtt ctgtaaagag catcgttggg aagtctattc agaaacaaga aaagaatatt  85740
ggaattctga tgaaggcata aaaatccgta aaactaaagg gcctaaaatt tctaagtcta  85800
aaaaaggtat aaagattgaa gcttgttcag gacctaaaaa cggaagatgg aatcctaaca  85860
aatctgaacg taataaatat tattattcag tgaggtcttt tactaataag acttttaaag  85920
aagaagttga taaactacca aataggcacc taagcgggat atgcggtgtt gaaggggctt  85980
atcaattaga ccatagggta tctatcaaat atggatttga aaatggtgtc tctcccgaaa  86040
```

```
taataggaca catttgcaat ctagaaatga ttccttggga aaagaatcgt agtaaagatt  86100
ctaaaaatag tatagattta gatatgctat tccatttaat tgaagaatat gataggaaac  86160
actaacttat ggaacttacg gatatcacta gggccttcga gtcaggtgac tttgcacgtc  86220
ctaacctttt cgaagtggaa attccatttc tcggtaaaaa ctttagcttt aaatgtaaag  86280
cagcacctat gccggcaggc attgtagaaa aagtaccggt tggctacatg aaccgtaaaa  86340
ttaacgtagc tggtgaccgt acgtttgatg attggaccat taccatttat aacgatgatg  86400
cacatgacac tcgtcaagca attgttgatt ggcagaatct ctgtcatggt atgaccaatg  86460
aaattacggg tgcagcacct gcagaatata agaaacaagc agtagttcgc cagttccatc  86520
gtgacggcaa gactgtgacc aaagaagtta caatttacgg cttatggcct actaacgttg  86580
gtgaagtcca gatggattgg gacagtaata acgaggtaga gacatttgaa agcacatttg  86640
ctattgattg gtgggaataa tttttacttt tatagcaaat tatgatagta taaatacatt  86700
caaacaatga agtcaaggag tttagaatgt attgtactta tttaactata tacacggggt  86760
ctaaaatgcc ccgtcgttat atcggctcaa catacgttga aaggattctt gaagaagggt  86820
ataacggttc agtattatcc caagcatata aaaagatttg gaaatcagaa cgtaaagaaa  86880
atccacacct ttttaaaacc cgaattttgt ctttatttga aaccgataaa gaagctcgta  86940
tagctgagaa ggaacttcaa ataaagtata acgtagtcaa atccaaaaac tatataaata  87000
tgtcattagc tcagcctgat gggttctttg gaatgtctcg taaaggatat aaatggtcta  87060
aagaatcttt agataaaagg tctgctacca atacaggtaa aaagaggccg gagcattcca  87120
aagctctaaa aggacgaaaa cgacctggac aagccaaagc tatgtcaggt gaaggtaatc  87180
cgatgtttgg taaagaacat ccggctaaag gcaaaaagat taatcagcca aggatgattt  87240
gccctatctg tggtgttgaa tcaactcgtt cggctataac ccgttatcac aaacacgaaa  87300
atgaatgagt ataaatagaa ttatcaagga gcttcggctc cttatcccat tcatcggaga  87360
ctctaatggc aaactttaat acaatattaa gttttcttaa gccatgggct aatgaagacg  87420
aaaaagaata taaacaacaa attaataaca atttagagtc tgtcaccgca cctaagcttg  87480
atgatggcgc tcgagaaatt gagacacaag agcaaaatat tccttataat gctcttatgc  87540
aacagatgtt tggtagtaat gagcctgaag ttaaaaatac cagggaactt attgatacct  87600
accgtaattt aatgaacaac tatgaagtcg acaacgccgt acaggaaatt gtgtctgacg  87660
ctattgtcta tgaggatgat aaagaagtag ttgcattgaa tttagacggg acagaattta  87720
gtcaagcaat taaagataaa atcttggccg aattcagtga agttttaaac cttttaaatt  87780
tccaacgtaa aggcaccgac catttccaac gctggtatgt agactcaaga attttctttc  87840
ataaaattat aaaccctaaa aaaatgaaag atggcgtaca agagcttcgt cgcttagacc  87900
cacgccaagt ccaatatatt cgtgaaatcg ttacacgtat ggaagacggt gttaaaattg  87960
tagacgggta tcgtgagttt ttcgtttacg acacaggtca tgaaagctat tgcgcagatg  88020
gacgcattta ttcagccggg actaaagtta aaattcctcg tgctgctgtg gtttatgccc  88080
attcaggatt attagattgt tgtggtaaaa acatcattgg ctatttgcaa cgtgctatta  88140
agcctgcaaa ccagcttaaa ttgatggaag atgcaatggt catctaccgt attacccgtg  88200
ctcctgaccg tcgtgtgttt tatatcgata caggtaatat gccttcacgt aaggctgcag  88260
cacaaatgca acatatcatg aacacgatga aaaaccgtgt ggtgtatgat gcttcgacag  88320
gtaaaattaa aaaccaacaa cacaatatgt ccatgactga agactattgg ttgcaacgtc  88380
```

-continued

```
gtgacggtaa agcggtaaca gaagttgata caatgccagg tgctactggt atgagtgata  88440
tggatgacgt tctttatttc cgcacagcac tttatcgtgc gctgcgtgtt cctgaatcac  88500
gtatccctag cgagtctaat tctggtgtta tgtttgatgc cggtacagca atcactcgtg  88560
acgaattaaa attctctaaa tggattcgtc aactacaaaa caaatttgaa gaaattttcc  88620
tagacccgtt aaaaacaaac ctcattctta aaaagattat tacagaagat gagtgggaaa  88680
aggaaataaa taatattaaa gttacgttta accgtgatag ctatttcagt gaaatgaaag  88740
atgctgaaat catggaacgc agaatcaata tgctaacgat ggctgaacca tttattggta  88800
agtacatttc acatcaaacg gctatgaaag atttcctcca aatgactgac gaagaaatta  88860
atcaagaagc taagcaaatt gaagaagagt ctaaagaggc tcgtttccaa aacccagatg  88920
aagaagaaga ggatttctaa tggaagattt aatcgaagct attaaatcaa acgacctcgt  88980
agcagttcgt aaagcagcag ccccgcttat cgaatctcga gtagccgctt tgattgaagc  89040
ccgtaaagca gaaattgctc gctccgttat gattgaaggc gaagaagctg acgaagatga  89100
cgaagacgaa gataaagacg ataaagcaga taagaaagac aaaaaagaat ctgacgacgc  89160
ggatgatgac gacgaggacg acgaataatg ttccttatcc ctgatgatta cgaattaact  89220
ctagaaagcg tagaggccaa aattccagaa gcacagggac gttttgctgc tctttctgaa  89280
gcgctagaga aaagcgatat aaataatctt gtagagaaca tgattgctga aggcgatatc  89340
gaatatgcta tcgctcttgg ttctttaaat gaatcaatgg ctcttaacga atttatcgtt  89400
aaacacgttt cctctaaagg tgtgcttact cgtactaaag atattaaaac ccgtcaacgt  89460
aacgcattcc aaacgaccgg gttatctaaa gcaaagcgcc gtcagattgc tcgcaaagca  89520
tctaaaacca aacgtgctaa tccatctact caagtgcgtg ctgaacgtaa gcgtaagaaa  89580
gcccgttcta aacgtaaagc ttttggactt aactaatgaa acctgaattg ctcatcgaac  89640
attggggaca accaggtgaa attatcgatg ggttcctat gttggaatct catgatggaa  89700
aaaattctgg gcttgctccc ggcctttata tagaaggcat tttcatgcaa gcagaggtag  89760
ttaaccgtaa taaacgcctt tacccaaaac ctattttgga aaaagccgtt gccgattata  89820
tggcagaaca ggttgctact aaacaagctt taggagaatt aaaccaccca cctcgtgcta  89880
acgttgaccc tatgcaagct gctatcatta ttgaagatat gtggtggaaa ggtaatgatg  89940
tttatggacg tgcacgtatc atcgaaggtg accatggccc aggtgataaa ctagctgcaa  90000
atatccgtgc cggttgggtt cctggtgtta gttctcgtgg tcttggttct ttaaccgaaa  90060
ccaacaaagg atataagcgt gtaaacgaag gttataaatt aaccgtcggt gttgatgcag  90120
tatggggacc atctgctcct gatgcttatg taactccaaa gcaaattaca gaatcacaaa  90180
cggtagaaac cgataccagt gccgatgacg cctttatggc tctcgcagag gccatgaaaa  90240
aagcgttata aatattatta tctaaacaac aggactacaa aatgcttaaa gaacaactga  90300
tcgccgaagc acagaatatt gatgcttccg ttgctcttga cagtattttc gaatcagtta  90360
atatttctcc ggaagcaaaa gaaactttcg gcactgtatt cgaagctacc gtcaagcaac  90420
acgccgtgaa actggctgaa tctcacatcg ctaaaatcgc tgaaaaagcg gaagaagaag  90480
ttgagaagaa taaagaagaa gctgaagaaa aagccgataa gaaaatccaa gaagctgccg  90540
gtcgtttcct tgaccacgtt gctaaagaat ggatggctga aaccagctg gctgttgata  90600
aaggtattaa agccgaactg ttcgaatcca tgttgatggg tatgaaagaa ctgtttgttg  90660
aacacaatgt ggttgttcca gaagaagcag tagatgttgt tgctgaaatg gaagaagaac  90720
tccaagagca gaaagatgaa accgctcgtc tgttcgaaga agttggtaag cgcgacgcgt  90780
```

atattaatta cgtacagcgt gaagttgctg ttacggaagc aactaaagac ctgactgaat 90840
ctcaaaaaga aaaagttagt tctctggtag aaggcatgga ttattccgat gcattcggta 90900
aaaaaattgg cgctattgtt gaaatggtta aaggtcagtc tgacgttgaa aacccaatca 90960
ccgaagccgc tataaataaa aatgtagacg atgctgcggc actgaattac atttcagaag 91020
cagttgaaga aaaaggcgct aagcctaccc tgtccttcgc ggacctgtct gcaatcgcag 91080
catcacgaat ttcttaatta ataaggttat acaacacatg aaaaagaatg cattagttca 91140
aaaatggtcc gctctgctgg aaaacgaagc ccttcctgaa atcgtgggtg cttctaaaca 91200
agctatcatc gctaaaattt tcgaaaatca ggaacaagat atcctgactg ccccggaata 91260
ccgtgatgaa aaaatctccg aagcatttgg ttctttcctg accgaagctg aaattggtgg 91320
tgaccacggt tatgatgcta ccaatatcgc agctggccag acttctggtg ctgtaactca 91380
gattgggccg gcagtaatgg gtatggttcg tcgtgctatt cctcatctga ttgcttttga 91440
tatttgtggt gttcagcctc tgaataaccc taccggccag gtatttgccc ttcgtgcagt 91500
ttatggtaaa gaccctatcg ctgctggcgc taaagaagct ttccatccga tgtattctcc 91560
agatgctatg ttctctggtc agggtgctgc tgaatctttc gaagcactgg ctgcaagcaa 91620
agttctggaa gttggtaaaa tttattctca cttcttcgaa gctaccggtg ctgcacactt 91680
ccaggctgtt gaagccgtaa ccgttgatgc tgctgctact gatgccgcta aactggatgc 91740
tgctgttacc gctttgattg aagctggtaa gttggctgaa ttggctgaag gtatggctac 91800
ttctatcgct gaacttcagg aaggctttaa cggttctacc gataacccgt ggaacgaaat 91860
gggcttccgc atcgacaaac aagttatcga agctaaatcc cgtcagctga aagcaagcta 91920
ttctatcgaa ctggcacagg accttcgtgc agtacacggt atggatgcgg atgctgaact 91980
gtccggtatc cttgctaccg aaattatgct cgaaatcaac cgtgaagtta tcgattggat 92040
taactactct gcacaggttg gtaaatctgg tatgaccaac accgttggcg ctaaagctgg 92100
tgtgtttgac ttccaggacc cgattgatat ccgtggtgct cgttgggccg gtgagagctt 92160
taaagccctt ctgttccaga ttgataaaga agcagccgaa atcgctcgtc agaccggtcg 92220
tggtgctggt aacttcatca tcgcttcccg taacgtagtt aacgtactgg ctgcagttga 92280
tacttctgta agttatgcag ctcaaggtct gggtcaaggt ttcaacgttg acacaaccaa 92340
agcagtattt gccggtgttc ttggtggtaa atatcgcgtt tacatcgacc agtatgcacg 92400
ttccgattac ttcaccatcg gttataaagg cgctaacgaa atggacgcag gtatctacta 92460
cgctccgtac gttgcactga ccccgctgcg tggttccgat ccgaagaact tccaaccggt 92520
aatgggcttc aaaactcgtt acggtatcgg tatcaacccg ttcgctgacc cgtctgcaca 92580
ggctcctacc aaacgtattc agagtggtat gcctgacatc gttaacagcc ttggtctgaa 92640
tggttacttt agacgcgtct acgttaaagg aatttaatgc tttaacgtta aaatacataa 92700
ccttatggga gactccggtc tcccattctt gtttctatac tatgcaatct taactcgacg 92760
attgatgata tcacggaagt caatacgatt ttcttggatt ttcagccagt taccagattt 92820
gtctttggta tgggtagagt attcaccgtt ccaccagaag tcagtttcat aggccagggc 92880
ttcgtatttc ttaaccaatg cattaactgc attaccgtta ggattggtac caaatttttc 92940
taccagagct ttgatgtctt tgtcaaggtt agaaagtgta gtacggataa agtttaattt 93000
gttcattttt aatctcctca tgttttgata ggtctatagt aacacgacgc tttttgtgtg 93060
taaaccactt ttataaataa aattatattc tcaataagga aaatagcaat ggctaaaatt 93120

-continued

```
aacgaccttt taaaagagtc gaccactact tcgagttctt cgattggtcg tccaaattta  93180
gtagctttaa ccagagctac gaccaaactg atttataccg accttgtagc tcagcagcgt  93240
actaaccaac ctttggctgc tctatatggt atcaaatatc ttacagaaaa aaacgaatta  93300
tctttccaga caggtgctac ttattctggt gcagtatccg ctaaagaccg tgccactatt  93360
ccagttttca ctgcaggcgc tgtttacgct aaagatgatt tgttccaatt tgaaaacgta  93420
gtttataaag ctttggtagc atcaccattt gcgggtgcta ctggtgatga atacgaacaa  93480
cttcaagaag ctattgttaa attgaccatt cgtattatgt ctgaagccgc actgactgag  93540
cgttttgaag gtcctcaaga agtagatatc tctgaagcca gattcatcgt taataaatgg  93600
aacgctccag ttaaatcccg taagttgaag agtactgtta ctgtagaact ggctcaagac  93660
ctcgaagcaa atggtttcga tgcccctaat ttcttggaag acctcctggc tactgaaatg  93720
gctgatgaaa tcaacaaaga tattcttcag tccctagtta cggtttccaa gcgttataaa  93780
gttgaaggtt tgtgtgatga cggcttaatt gacctgagtt atgctaactc accggaagct  93840
tctcgcaagc tttatgaaat agtttgtgaa atggtttctc atatccagcg cgcaacctct  93900
tatacggcaa cttatgtagt agcgagtact cgtgtagctg ctgttctggc tggttccgga  93960
tggttaagac acaccccaca gaacgacaaa tatctttctg caaatgcata cggattcctg  94020
gaaaatggtt tgcctgtgta ttgtgatacc aacacgccga ttgattatgt tactgtaggt  94080
gttaaagagg aattcggtgg gaaagaagcg gtaggttctt tgttctatgc gccgtataca  94140
gaaggccttg atttggctga ccctgaacat gtaggtacat ttaaagtggt cgttgaccct  94200
gaaagcctgc aaccatctat tgcattaatg gttcgttatg cactggctgc taacccttat  94260
acggttactt ctgatgataa acaagcccgt attattgatg cgactaatat ggatttgatg  94320
gcgggacgtt ctgatatgtc cgtattgctt ggtgtgaaac ttcctaaagt tttgactgaa  94380
ttaaactaac aaaaaaggga ccgtgaggtc cctttgtcgt cttacgacac taattcaatc  94440
catactgctc gtagggtatc ttttacgcac tcaacaagtt gctttttaac ttcaacagga  94500
ttttctgcat cagttaattc taattcttca cgggcagctt cttctaagat atcttggact  94560
gtcaagccca ttacctttcc aaaatccttt ttagatactt cgccaatctt actgatgacg  94620
ttgttaatgc ggttaacagt cacataatcg gtgaattgcc acatcaaatc catatcgtct  94680
tgggataaaa ctacagccgc cttaataggc ttatcagact ttttcttctc gctgaattta  94740
gagttcttgc atttaatcgc tacgcgattt ccgtttggaa gccaggtagg aacatcaggt  94800
ttcaatacaa agccttcagc cgtgaatacc ttaccttcta ccttaggaat aaagtctgtc  94860
gagtttgcaa tagttaggcc agcgttatcc actgcaaaat tataatcagg aataactgaa  94920
tcaaagtcat taggtaattt aataaggtct tcaaagctac cagtagccag acatggagct  94980
accttaaact tatggataat acagaaggct tccatcaatg tatcggttag aacagattct  95040
gaaccatctt ccttagtaac tcggatatcg aacacataaa agtctttatc accgtagtcc  95100
acattcttct ggatacctgt cccagcgaat tcgccataaa tctggtacga ctgataatta  95160
atcgattcaa ttagatgttg aactgattta atagaatcag catagttctt aagtacaatt  95220
tcatagccgt agaaatcttc agcagggagg atagcgccag tgcgcttggc gcatgtgact  95280
gcgtcacgtt ctatgattag actaaagtta gttccatgaa tcttctcacg tgctacccat  95340
tcaccaccag tcaaaccgtt agtacggagt tttcgataa acttattgtt gtagtggttt  95400
tcgagactgc tatatttctt gaacataaat caccataata aatataatta aatagaagag  95460
ctagtagtct tctgtcacca agccaaatgg tttaacggaa ggacctagac ccattataac  95520
```

acatctaaat ttaaagcata ttactttgaa ccagaacgcg ctttgcgccg aaccttgttg 95580
ttcaatcttt tacgataaac aaccttttct ttcgctttaa atttgacctt ggcttgttct 95640
acatcaaccc atgctttggc catgtcctta gcagtcccgc ccattttttt agcaatttct 95700
ataaaattca acccagattc gtgtaaaaaa tgtactttaa ccttatccat aacaattctc 95760
tcgttgagtt ggtaaaaccc atcttaacat agaattttta acttgtaaac aggaattttg 95820
tactttaatg caaaatgggc cttgcggccc ttaattaata aacgtaatcg tatataatac 95880
cagcttctaa agcggtgcga tgaataattc gaccattacg agattcttgt acatcaacct 95940
ctggatagtc ggtaatcatt ttttgaagcg tatatcggtg caaataatac gggctatccg 96000
ggttatcagt tttccagtct tgcccagcaa gagtcatttt ctgaatttca tccataaccc 96060
accaaccaca ccagatataa gctgaattgc gtactggcaa tggatgcaca taaggtaatt 96120
cgccatccgg aactggtgcg actttagccg tgactgttac attaccggtt tttgtgacag 96180
tcgccgggtc ataatcagtc gccgaaacca caacagaaac ttcaataacc tgtgaacctt 96240
cagcacttgt atcgattgct agagtatccg tggtgccaac tacaggagaa ccatctttct 96300
tccaagaata ggcaaaagta gcaccagcag gcgcgccgac tacatccgct ttaaaagaag 96360
ctggagtgcc ttccggaaca ttaattgatt ctggggttaa tgtaacagaa acatctgaca 96420
tagttttgtt ctggatagtt aaagtcgtct cagcttcagc agtttccggt tcgccgtccg 96480
ctggtgtggt tgttgcaaca actttaatag tcttgctgcc tgctggacca acagcaacat 96540
aatccattgc agcggtcaca gaagattgag gaacgccatc aacggtccag acaaatgatt 96600
cggtaccttc agctgcagcg ccagcgccgg ttgcagtgaa attggttgtt gctccaataa 96660
cggccgtagc cgccaaagga gcaatagtta cggtataagc cataataaac ccttatttta 96720
aagtgacaaa agatgagtta cgagtttctc gtattagaac agacccatta cgattgatgt 96780
aataaatcaa actgaatagt gtttggtgtg cagtaggatg ttggaaagca gttggacgtt 96840
ctttccaatc cggggtctca gaaatccatt ggtaaatcca ccaaggaacg gtgcaataac 96900
ccgggttctt accgataagc aaaagattag gactgaagtc ttcaggtaaa gagaatacag 96960
gtttttccga ttcaacaacc ttggctacag cctctttgaa tttctcttca acaaatggaa 97020
catcttcttc aataatctct actttaggaa gttcggctac ctcaacgact tcaacaactg 97080
cctcaggagc atcgaacaac agggttgctt cttctttagc aggttcagca ccatcaataa 97140
attcattaga acctgtaagt tcgtcggcgg catcaatcaa atcagaaatg gacaaccctt 97200
cggtttccgg aagtggttcg tcggccaagg ctttaagacc ttcagtgata tcgataatca 97260
aattatcaaa cgaacgggtt ttcttaagtt ttaaaccgaa ctgttcgccg tattcgatta 97320
acttagcttt agcttctttt ttatcttcga gtgcacgaag ctcttcaata tattgagtat 97380
ccataattag tctcttgttg gtgtataaat ataactatat ttataactga gaattactta 97440
tgcaaattca agtacatttt gataatttta gtcatgtccg tattgaatgc gatgaatcta 97500
cattctacga actcagagac tattttagct ttgaagctga tggatataaa ttcaacccta 97560
aatttcgtta tgggcaatgg gatggacgta ttcgtcttct ggattataac cgtaaacttc 97620
cttatggatt ggttcctcaa attaaaaagt tcgccgaaca atttgaatac tctctgtgga 97680
ttgacccacg tattcttgat caggaagata tttctcgtga agattttgat tcatgggtgg 97740
cttctcaaga aatttattca gggtctacca agattgagcc tcattggtat cagaatgaag 97800
ccgtatacaa cggcctgaca aaacgtcgcg caattctgaa tttacctaca tccgcaggta 97860

```
aatcattaat ccaggcactc ctgagtcgat attacgttga gaactatgaa ggtaaaatcc  97920

ttattttagt tcctactact gcacttgttg accagatgat taacgacttc atcgattatc  97980

gtttgttccc taaagccgca atgcttggaa ttcgttcagg tactgctcgt gattctgatg  98040

caatgattta tgtttcaact tatcagactg ctattaaaca acctaaagaa tggtttgctc  98100

agtttggtat gtttatgaac gatgaatgcc atttggctac aggtaaatct atttctacta  98160

tcatcgaagg cctaaccaac tgtatgttta aattcggttt gtctggttct ttaaaagatg  98220

gtaaagctaa tttaatgcaa tatatgggtt tgtttggtga tgtgtttaag ccagtatcca  98280

cctcccagtt aatggaagaa ggacaggtta ctgaccttaa aatcaacagt atcttccttc  98340

gatatccaga cgaattcact gttaagatga aaggtaaaga ttaccaatca gaaattaagg  98400

tcattactaa ggctactcgt cgtaataaat gggttgctaa tttagctgtt aaactcgcta  98460

agaaagaaga gaacgtattc ctgatgttta aaaacatcga acacggtaaa actctttttg  98520

aaatggttaa agagcaacat aaagaagttt attacgtatc aggtgaagtt aataccgaaa  98580

cgcgtaatgc tctgaaagta atggcggaaa atggtaaggg tattattgta gtggcaagtt  98640

atggtgtgtt ctctactggt atttccgtta agaaccttca ccacgttgta tttgctcacg  98700

gcgtaaaatc taaaatcatt gttctgcaaa caattgggcg tgttctacgt aagcatgaca  98760

gcaaacaagt ggcccaagtc tgggacctcg tggatgatat gggagtccgc cctaaatcta  98820

aagattctaa aaagaaatat gttcatttaa attattgtct gaaacacgga ttggaacgta  98880

tacaacgata cgccgacgag aaatttaatt atgttatgaa agaggtacag ctttgaatta  98940

tcagaaaatt tacgatgatt taatagagaa tgctaggtcc agaggatgga ccaaagccac  99000

tgcgccctgt aaaatcgaaa ttcatcatat tattcctaag tcgataggtg gttccgatga  99060

ccctaacaat ttagttgcat tgactattag ggaacatatt ttaggccata taatcttggc  99120

taaagctcaa ggtggaaaat tatggcgggc cgcatttggt atgacatgcg gtaaaagatt  99180

aaatgagata agctctaggt ctatttccat tttaaaagaa aatgcttcta gattaataag  99240

cgaagccatg attggtaata caaacggttc ttatgaatgg actgatgaac gaagagaaat  99300

acaccgaaaa gctatggcta aagttggatt aacagaagcc aaattaaaag ctttagaaaa  99360

ggcttggacc aaaaataaag gctccaagca atccaaagag actatagcca aaaggtctaa  99420

agcaatgaaa ggatttacac ctattaaagc cggagattat gaaacgtgtt caaaagccgg  99480

caaagccaat aaaggtgtaa agaaatcatt taggtctgag gaccattcta aaaattggca  99540

agctactttg gctaagaaat atccacactg gttaatgtat gatgagctta aagagctttg  99600

gataaataca ggaaagctta aagttggtaa atttacaaaa gaagccatta aagctggtta  99660

tcctaatgtg cattacggta aaatggttac caaatttttc gaggaaacaa aatgaaaacc  99720

tttaaagaag ttattcaaga agcatctatt gaaagcttca tggctaaaat tggttcttgt  99780

cagactatgg acggtctgaa ggaattagag aagtattaca aaactcgtag taaggaagct  99840

gaacttcgtg attcggacga tattagcgtg cgtgatgcat tggctggtaa gagagctgaa  99900

ttagagtcga tggacgacga ggaagaggaa gatttctaaa caaaaaaggc ccaacctttc  99960

ggaagggcca ataaccataa atggctatac acactagact aaagtagtaa ttgggtttcg 100020

ttcagctgct cttcagtgtt ttccgtaacc ggcaagcttt gaacgtaatt ataacatgaa 100080

cccggatgaa ccggaccttt ttctgtttca acaaccaatg cagcatcgat tggagtttta 100140

cagacaacgc aaatcttatc tgacatgatt gtctccttag tttaacttac atatctattt 100200

attacttgct aaagcggcat taatgaattc ttggagaagt ttcattttat cagcatctac 100260
```

tttaataggt ttaatatttt tggtgcgcct catttttcac ctgcttcaaa tttcctgagc 100320
tccaacatat tctttaatga gaaacctctg gctttgactg cgtctaaagc tgaactacaa 100380
aagtcctgta ataaagccca atactggatt gacgtatcga ttttaattac actagaatct 100440
gcagccatta cagtctttaa ttcagacttc tcatactggt ccatacaaac ctcatcacca 100500
ggctctccac gtcccgtgta gaaatctaat cgcttcttaa gtgaggtctt tttctggatt 100560
tctaatctca ttatttcttt cttacaattc gtatacagtc ttagccattt gctgtgcagc 100620
aaaacgttgt tctgtacttc atactgtaaa cgagttccat caatctttaa atcttcatcc 100680
aaagcatctt gaaacgactc taacttgtac tcaatctctt tactcatcgc atgtttcctg 100740
tgtaataacc ataagaccat tatacactat tcaattgaac agcaattaac cactctgtga 100800
gagctgaatt ctaatttgct ctaatgtatc agggtcatca acgatactaa actgaacggt 100860
cacgataatc gagttatcat cgtacacagg ggtcacacct acggccaggg cagaaattct 100920
aggttcgaag ttccgcacag cggaaactat attacgctta atagtatccg tgattaatgg 100980
ggttatattc tcaaacaatt ggttactgat gtcgcaacca aattccggca taaaagggcg 101040
tgaacctttg cgagtagtaa taatgcctaa caaactattt tttactgcac gagcacctgt 101100
agctttagcg acgtctctat tccaagacgt cctcatttca gggtctaaat ccgaatacat 101160
tttattgata ttcattacat caccttaaag aactctttaa gtccctcaat aacgtggacg 101220
gtatgttcac cacattcaca agaaataggt atggccaaaa taggcttagg ggtaactagt 101280
gcatcataaa cttcttttat atctttttct gttatcacag aataaaggtc atcaagttcc 101340
gcatcgctta aatcggaaag aaaaagcttt tcgcctgcag aagttaaaat ataatcgata 101400
caccctgcga ccatcatagc cctattttta tcttcaaaga gtttagggta cctgaaaaca 101460
attttaaagt tgccaaagtc tttaataaca tcgggctctt tacctaatgt tgcgcgagtt 101520
agtgtcatag ggacaacctg tgagcgacca caactacaaa cccactcacg ttctatattc 101580
acttcagcta atgaatgggc ccacaggttt atcaccagga gctcagattc ttgcttgttt 101640
aaatcacgag catctgtgca attcgaaatg agttcattga taaaggactc tattctgcct 101700
tctaatttag cttggagcaa gtccttatac tctctgaggg taaatgctct gcattttatg 101760
gttttgtttt taatttttac gtcaaaagta taattcattg tcttctcctt taagcttatt 101820
tataaataca tcaataagag gacaccctat ggctaatata gtacgttgtg aaatgcctga 101880
tggagtccac cgatttaaac cttttacagt agctgattat cgtgatttta ttttgattcg 101940
aaatgacatg aataataaat cacctgaaga gcaaaaacaa attttagatg agttactgga 102000
agaatacttc ggtgaatatc ctatgtcatg gcgcccgtat atgttcattg aactttacac 102060
gtcatcgctc ggcaagacca aaattcctat ccgatacact tgcagtaagt gtgaaaagga 102120
tagacaagtt ttattcaatt tgaaacaggc caagttagat aatcccacaa ttgaagtggc 102180
aggcttgaag ctaacattca aatttccgga aatagaatat cccgacaaat ctgaattgat 102240
tttgaacacc ctccaaacag tagaagatga aaacggaaaa tataattgga ctgacctttc 102300
tgaagaagac caattagccg taatagatgc tatagactta tccactttag aggatatagt 102360
caaacaaacc agccctatta atttcgaact caaatatgga tgctgtaatc gtagaacaat 102420
tgcgtatacc gatattttag aggtgtttaa acttatagtc aatccggatg agatattttt 102480
attttaccaa ataaaccatt tattggtaaa gaacaattat tcattagaaa gcattatgca 102540
gatgattcca atcgaacgcg gtattgcttt gtctttggtt gaaaaggacc ttaagaaatg 102600
agttcaaaaa ctatgcaacg tgaaggcttt cctaatatta gtatacgcct ttacgaagat 102660
tatgacgcct ggttagagca tcgttttgtt gaactaggcg cgacatttac tactctaaca 102720
atgcgagatg gactttacgg tagtaatgaa ggattgcttc agttttatga tgcaaagaac 102780
cttcatacta aaatggatgg cgagcagatt atccaaattt ctgttaagaa tgctaactcc 102840
gagcgtaccc agtcaagaat ttatggaagc aaacactttg ccgtaggagt ggattcgaag 102900
ggtgacaata tcataacaat acaactcgcc ccaatccact ttttagagaa ccttaaattt 102960
agtcgtatgt tctttccaag cgtacaagaa acattgacag aaatgattgg cgtaatttat 103020
caagaccgtc ctttacttgc tccaccattg aacgggataa acgtttatgt tcctaatgta 103080
ccatggtgcg attcaatgga ccgttatatg gaatttgttc gtgaagtagg tatggctatc 103140
gaatcagata aattcgtatt tgtatgggaa gatatcgatg ggctttctat tatggactac 103200
gaatttatgg ttaatcaaga gccaattaat tttgtggtag gtgagcctcg tttaataggc 103260
caatacgtcc aagatatgga cactcctatc gcatttgatt ttgaatggtt aactaaagcc 103320
aaccagcatt ccagaaaacc atatgaaaac gctactgtat acgcccactc tttcttagac 103380
aaaaacgcca cacgaattac ttttggtgat gggcaaaaca gtatattggt ttctcgctct 103440
ggtggatatt ctgattatac ctaccgaaac ggatttgaag aagccgatag attagttact 103500
atggcccagt atgatggtta cgctcattgc aaagtatatg ggaactttga attaaccccg 103560
ggtgataaga ttaatttcta tgaccctaaa aaccagttcc aatacgattt ttatgtagac 103620
gaagttattc atgaagtgag taacaataca tcaattacaa acctttatat gtttactaat 103680
ggtaagccta ttaagattga agaaccaccg aaggttaaaa atgaacttaa aactgatact 103740
cccgatcaag aaaataacgc tgggtgataa agagatttct attcctaaat tgggccttaa 103800
acaccagaaa ctggttaaag atgaaaaaga cccttataag gctcttcaca tattaatgaa 103860
ttccatttat aaaggtttat ccgcggcaga gaccgatttt gccgctcttc accttttaga 103920
attcaatgga agattaaaaa gtaaagtaac caaagacggg tttacttata acctaaatga 103980
cctttatatc tgccagcgac ttgaattcca attccaaggt aaaacgttta aatttaaatc 104040
acacgagcca tttcaaacat ttggtcctgt tgatagtgta ttacaatctc tttaccttgg 104100
tgatgacgta ccagattttc tggatatgcc tgcctttgtt gctacatggg ccgacgatat 104160
aacttctact atagctatcc ctggtcctaa tggtcctatc aaaggattgc ttaaaatcat 104220
ggatatctta aatgaagaac gaatctaatc agaatagttt tcgtcgcaat aaactgattg 104280
aagaaatggc tcctcagcgt cgtgctgagg cgctagccca aactcagaac gacgaattag 104340
gaaatatatc agatgtttta tccgattccc aggcggcgtc tgaattgctc tctgaagtgg 104400
ttgagacaaa gtccaatcag attattagtt ctgtagaccg agtagataaa agcgtccaag 104460
atgttgtcgc tggaacagaa ttaacagccg aagccatatc agaacaaacc caacagtcta 104520
aagctctttc ggatgcatta aacgaaaaga ttagtaagct ttctaatatg ttggaggcta 104580
aattttctgg tatttctatt ccaccggaag ggagctcatt aaaggttatt gaagactcta 104640
ttcctgaaga acctaaggct gaaactccta aagttcctgc tgttgttgaa gatattcttc 104700
cgcccgaaga caataaacct gacgccgaat ttatgcctga gcctcctaaa aattcagatg 104760
aaggtaaaga aggtgataag acttctcttt ctgataaaat tgaagccctt actaaaataa 104820
ctgaaaaggg atttaaagct tctataggcg tcgctgatag aatttcaggc atgcttttta 104880
agtataccat tactgccgcc gctgaagctg ctaaactcgc tgcaggttta gttcttttaa 104940
tatttggtat agatgccatt cgtgtatact tccaatattt catggaccaa tttgaatcag 105000
ggtggaaaga atttaacgat aagtttaaag agtggggacc tgtacttgaa ggattaatga 105060
catgggccaa gaacgccgaa gccatgttta gtgaaggaaa ctggttaggt ctggccgaag 105120
ctattattcg cggtatggtt aatcttacta aaaatatggc ccagctttta atgctcggta 105180
tttctaagtt gatttctgct attttaagca aaatacctgg tatgggtgag ttggctgaaa 105240
acgtagaggc ttccgcttta atgtcgtacc aacaaaatac cggagccact ttagatgacg 105300
aagaccaaac taaagtggcc aagtaccatg atagacgttc tgctgaggct ttagaaacag 105360
ccgagaaaat gaataagaag tataaggata aacctgagct tataaaccaa gcagagaaat 105420
acggtaatct tactaaagaa caagctgacc aattacgtgc aggtggaatt gacacaagct 105480
tccgtgacct ccctgaagaa gaacgattag agtatttcaa gaagcgtgat aaagcccaag 105540
ccgatattat tcgtttgact caaactgctg ataatataat gaagcctgat tctaaagata 105600
tcgaaaatgc taaatcattt aaagctgata tcgagaaaca attggccgac cctattatgg 105660
ctaaaggtgg agcaccgaag gaccttaata tccagcaatt acttgataag atgaataaat 105720
ctttagagaa atttaatgaa gctgaaaagc ctaaacctgc ttctgtagcg gaatctcctg 105780
aaaatactca ggttaaaaag gtggatgagc aaatgagagc aaaggaaaat gctaaatata 105840
gtcagcaagc tccaactcaa ataaatcagc aaacgaatat caagaaaacg agtaagacta 105900
gttataattt acctccacag tcttctactc ctgctcctgg tatgcgtcaa gctactaaag 105960
ttaattagga ttaataatga aagcaaaaga acttgacttt gatgtagcct ccttgtttaa 106020
aggaggctca aagacctccg ccggccagtc taaagctaaa ccggcccaaa ctacagtaat 106080
ggcccaatac ccggcagaaa gggcctccgg caatgacacc tctacagata tggtgttaag 106140
cgatttatat aaaaatggct tactttttac ggcgtataat tttagctctc gtgtatcacc 106200
tgatttgcgt aatgaccgat caagtcaaat gactaaaaag ttttcaaaag cctctagtaa 106260
acttaccggt aataccggag gattcagtgc ggttaaaaac ttgttcagta ataactctaa 106320
aggagttaaa tttgacaacc aagctttggc aaatatttta ctcccacgtt ctaaatctga 106380
cgtagattcg gtgtcgcata aatttaatga tgtcggtgaa tcattaatta ctaaaggtgg 106440
cggtactgct acaggtattt taagtaacgt tgcaagtact gctgtatttg gtgcattgga 106500
atctgtaact aacggcgtaa tggctgattc aggtgaacag atatacacca ctgcccgtag 106560
tatgtacgct ggcccggata accgtactaa ggtattcact tgggaaatga ctccacgaaa 106620
cgcccaagac cttatccaga ttattaaaat atacgaaatc tttaattact attcttatgg 106680
tgaaaccggc aactcagcct tcgctggtga attaaaagag aagattgata cctggtatcg 106740
ttctacgttt aaaaaagaag ctattgacaa gtttgacggt aagctattag gggaaagtat 106800
tacaagcttc ctttctaatg ttattgtggt aagtaacccg accatttggt atatccgaaa 106860
ctttggtgat agcagttcat atgatggtcg tgaagatatt tttggcccat gccaaatcca 106920
gagtatccga tttgataaaa ctccggacgg ccattttaac ggattggcta ttgctcctaa 106980
cttaccatct acgtttagtt tagaagttac tttccgtgaa atcattaccc ttaaccgtgg 107040
ctcactttat acggaaggat tctaatgtat actttacaag aatttcagaa ccaggcaatt 107100
aatattgacc tgcagaggaa taacctgttt agtgtggtat ttgctacagt tccttcttct 107160
aaatctcaag cgctcctcga ccagttcggt ggagctttat ttaacaatat cccattgaat 107220
acggatttgt ttggtattac acaaggagag ttgacccaag gtgttacgac attagtgaca 107280
gcgggcactc agaagttgat tcgtaagtca ggcataagta aatatctgat tggagctatg 107340

```
tcatccaggg ttgtgcagag cttactagga gagtttgaag taggtacata tctgatggat 107400
tttttcaata tggcttatcc tacggcaggt cttttagtcc acgccgttaa aatcccggat 107460
aatactttga actacgaaat ggatttgaac cataactcac ctaacatcaa aattaccgga 107520
agggaatatt ctccattggt attaagcttc cgtatggatt ctgaagctgc taactaccgt 107580
gcttttaatg attgggtcaa tagtgtccaa gaccctatta cacaattaag agcattgcct 107640
gaggatgttg aagccgacat tcaagtcaac cttcattctc gtaatggatt acctcataca 107700
gtagtaatgc ttaatgggtg tgttcctgtt ggtgtttcgt caccggaatt atcctacgac 107760
ggtgataacc aaattgcttc gtttgatgtt acatttgctt atagaagtgt acagacgggt 107820
gcagttggca aacaagctgc ttatgaatgg ttggaagata aagtccttaa aggcgtggcg 107880
ggtataagtg agagcaattc actgagttct tcagtagcta aattaagccg actttcagga 107940
gcttctagtg gattaacagg attggttaat acatttggtg ggcgtgctat taataatgga 108000
atatcgaggt tgttataaca aaaaaggaga gcatacgctc tcctttaggg gtttatttac 108060
ggaacgaaat gaaacctgtt gcagtcatta atggctgctt tttaacaaat accgtaactg 108120
aaataggagc ttcggattcg agttgtcctg tcactacact gttaaaaatg ttttcggttt 108180
gttccggata agaaaaattc tcaacaggtc ggatatcaaa ttgcttatct tcaccgaaaa 108240
ctcggcgtaa ttcattacca atggcactgt caaactcttc agaagcaggg ataacgtttt 108300
caactaccag ttcttgacca ttaaaacgga atgcagattt catattgttc tcctcatgtt 108360
tgtgtaaggt aatagtacca catccatgtg gtgttgtaaa ctacattttg aatttatttg 108420
gtagagcaga gatatccaaa gatgcggcaa ggatttccat agcttcgttg ctttcagaaa 108480
cggattcatt aaccaagaat tgactgaacc catccatcag gcgaacttca ccagtttcca 108540
tcaaatggcc gccatcgtaa acagattcgc tgagctctga aggaggtgtt actgtagctt 108600
ccataaggta tttgtgagat actctatcat tcatggcaaa agccgctact ttatcaacct 108660
tcaacaataa cccgcgcgga aggataattt ctgcttcttc ggcatattct gtaaggtcac 108720
caggagcgat aactttaact gcttcagcac ctcgaataac cataccaatt tcagcaattc 108780
tatctgcagg accttcaggg gcaattggat taccaaactc atcttcttcc cattctacct 108840
cttcgtcatc gacttcaccc acatcagatg aactaccact agccaattta aacaactcat 108900
cagcggagga taaagaacct tcaccaccaa caaaaacggc ttggttgtcg agggccatat 108960
aatttttacc aaattcacca aagatgttag gctttaatga ggctgacaca aagttcttaa 109020
agtaaaatgt tttgttatcg atattatgac gcagaatttt gtatggtaaa tcctgaccac 109080
gatacaaaat agtaccctta ggaagtttaa tacccttagt aaatgctgag tctaaatcct 109140
taatcaattt aatagccgtt gtattgtttt cggattcagg tttacctaaa aggaataagt 109200
tcataggagc atattcagct gcgcaatatt caataatggc attgctttcg tctttggtta 109260
ggtccttagg tttaatgagc tcacctgaat aagcatatgc atcactaata gaatcgttaa 109320
ttagtttata aacggcttcc atagcgaaag caattcgaga ggccttttct gaaggggagc 109380
ctttaaaacg ggtactcagg ttattaacaa ttttcttaat aatatccaga ctattggttg 109440
tattgatttg cgaaaggccg cttaaaagtc tatcgacttc tgtattaaaa aatgccatat 109500
ttttagagta aatttcaaac ccttgtttat ctctattagc ataatttagt ttaaatttac 109560
tatcagtcat taaagcgtga gtgagagcaa tggtgtatct aaagttggca aggtcctcgc 109620
tcttagattt aaactgagaa gcctggcgca ttttggtaat agcacctttt ttaaagttct 109680
gactaatctg ttcaataccc tcgttctcag ggccttcggc agtgtgaacc ggtacagaag 109740
```

```
cttcaaactc attataaacc tgcaattctt taggggacaa agtttcaggc tcagcagtag 109800
aatactgtgc ggctgctgcc atacgacggg aaatcttagt acgagtaata acagccttat 109860
cagtacgttt ctcttcaacc ttagcaatac ttgccgagac ggcttcaacc ttacttacag 109920
actgacctgt tttcttagaa acataaactt caccgacttt agaatcgact ttggtataaa 109980
ggtcagcatc aatttcaggc ataccottga tatcttcaat attagcacca cgacgtacta 110040
aaagaacgta ggtatgttta ccactgaatt ggaacatgtc atcaacaact ttaaacttgc 110100
cgccggtacg agccatcgcc aaacgagcta atacgcgctg aacagtagga cccttacctt 110160
tcattttctt ggtagggaaa cggaataaaa ccgcatccat tttaagtttg tttacttgtt 110220
catatacggt atcgaaaatg gtattcagtg taccaagcgg gtcagaacca aggccgccct 110280
taagttcagc cggagcaccc ttgcttgaca aactcattag aataacgtgg acatatttgt 110340
cgcccggctt aaccatttta atagcgtctc cttgagacgc ataagatacc atacgagcaa 110400
ccaggttatc gttacctggc gcttggatag agaaaatctg tggaataccg gaacccggtt 110460
taagatttgt tactggatag ttttttagcg gaatcactat caaaaacttc gtttaaattt 110520
tccattattt acccttgggt gaatttttct gggacattgt aaaggtccat acaagatgct 110580
aaaagaggca acacatcaaa cttagttgat tttacaaatg agtcaaaaga tacaggattt 110640
tcaatagtat caaaatcatc ttgatatgca accaattcgc cggtttccat tagtatgttt 110700
ccatcatata ccactgactc ttgaagctca tctgatgtca taacttcggc ctgaactaat 110760
ttattattag ttttagcagt accgtcatta taagaagcat ctgttatttt attaattttg 110820
agcattaacc cacgtggaag aataatttcc atttcgttgg aaggagcaag acctgcacca 110880
gggaatacca cgtttatttt gtgagcacct gaaatagccc aaccaatacc aacttgatcg 110940
tcattagact taacaagtcc ttcatctgat ttgtctatgg aaacatctaa acggacatca 111000
tcaggcaggg taccgattgc cgcatcagtc atccaagtac cgaaaatatt tggatataaa 111060
gatgtagata caaagtttct gaaatagaat accttgtttt taaccattgc ttcgtaaata 111120
ggtggaatca ttttctgaga acgatacagc gtaattcctt ctggtaatct atcaccattt 111180
ttaaaagcat catctaggtt atcaatagct ttttcgattt ccggggcggt tagaatacta 111240
gaacgaactt ctggattgta tatacccaaa agagcattat tcatatcttc atagcccgag 111300
ccgacatatt cacggatacc acgtttttgt gccggagtat actgagtttc atctcggtta 111360
tcaacaatag agaacattgt ccaacctgcg gctaatgcaa aaccacgaat ttcttttta 111420
atgaccttag tcttagcggc attccaagag ctttcagaaa gttccattgc catagtataa 111480
tctaaattag aatgtttcgc aaagaatttt cctaaccaag cacctttgta ttcttcaaga 111540
acttcgttta atactgaagc aaagctgctt aacgcatcca tagatgttat aggcttacca 111600
tgaatttttt ggaatgcccg aactttaaca tcatggtcaa cttcttttat tttaccttta 111660
gttactattc cactatcagc aaaagcgtcg ccaacaccgt ttatatttgt gactgtatta 111720
agaacacttt ctaaggaaaa tgatgcagta gaaatagtag atagttcatt agattctgga 111780
ataagtggtg cggtagccgg tttacttaat tcagaggcag aagcttcaaa tttagtaaac 111840
ataggagttt caaaacgtgc agattctaag gattgcgaca tagcaatagc acgacgtgaa 111900
atcttagtct tagtaataac agttttatca gtacgacgtt cttcaacctt agcaatacta 111960
ccagcaatag cggtttcttt agtaacctgt acgccttctt ttttacttac ataaacttca 112020
ccgacatcag aatcaaccct agtataaagc tctgagttaa tttctgggat gcccttaatg 112080
```

tcctcgatat tggcttgttt acgaactaca agaatataag tgtgtttgcc agtgaattca 112140
tacatcgctg gaatgacttt aaaacgtccg ccggttttct gtgctaccaa acgttggata 112200
atacgttgaa cgataggacc ttgtcctttc attttcttag tagggaaacg gaacatcaca 112260
gcgtccatac gaagggcttt aacctgatcg tagacaacac taaagattgt attaattgca 112320
tcaataggag tgggcccaag gccgccttta agttcagccg gagaaccttt agccgataaa 112380
ctcattaaaa tagcatgggc atatttgtca cccattctaa cctgtttaat agcatcgcct 112440
tcagaggcat aggataccat acgcgctact aattgggact ccacgccgcc aatcttccaa 112500
atctggggta ctttaagttt agggttcaag tttactgtag gcagggtgcc ttcggactca 112560
aacacttcat ttaattgttc ggtcataata attcctcttt aataacctta tttatgccat 112620
aaaaggcccg aaggccttta ttaaagtact aacaacgtac ggtacacttc aaatttagga 112680
ccctttttcat agcggtcgaa attatcttta aaatcagcga acgcgatttc attttcaaat 112740
tcaaggacaa tttgggacac tgcggtggag acatcgccac cttctttata tccaataacc 112800
acggtttcta aataagcttt catattatag tccagtttga gaccaatcac cgaatacatc 112860
ctcaaatgta tcagcttctg ttttatcgaa acgccaacct ttaataattg gaaggaaaat 112920
acctacagta tcggtacgtc ctttagaatg aacccaacca ttacattcac agtcagcaat 112980
acggccaatc aacttgcctt cacgagcttg tttcataaga agttcacggt ctaaatcagg 113040
acggtcttcc aatggaatca atacctttt acctgattta tctttcttat gggtggtatc 113100
tttaaagcct gagccacagt cacttgtaat tcgacggcaa cgtgatacta attcaacacc 113160
gccaagtttg ttagggtcct tagagtgttc ataataacct accacttcta aagcgatatc 113220
gattacttct ttgaacttga taagattctt agaacggcgg ttttcccagt aggagtccat 113280
gttcttaagg ataatacctt ccagaccttg gtcgacatat ttcttataaa cgactttagc 113340
ttcttcaaga ttattaaccc actggttttc gatagcttca acacgcgttg tgccatgcaa 113400
tacgacatta tgagccacca taagttctaa ggccgcaaag cgtacatcat acttatcgcc 113460
tttaatttta ccttcggaat atacgacatc cagtggaaca taatcccacg cctgtaatac 113520
catacctgct gcttcggttg gagtaatagt tccttgaaga gccttgttag ccaagccgtt 113580
tgacgtggaa cgatcggcga cagtttggaa ttccttagcc ttacttaatt caggaagttc 113640
ctcatcaaac atactaaaca aatcattgga tgctttaggt tctaccttag gagtatggta 113700
aactaattcg ccgtcaatca taacaccatt aggatgacgt tgtcgggctt cttcggtcat 113760
gaccatcaat tcagcagcca aaagattaag cccttgatat tcgttaccac cacgagtaag 113820
gaatgtcaca ccatcgttac gaacttcggc aaaacaacga gccccatcag cttttaattg 113880
agcaaacgct ggccatttaa tatttttctt aatcaaatct tcatcataag aactagccaa 113940
catctgtggt tgttcaggga ttaaaccttt ccaaaccttg ttagcaatag aaattgatgc 114000
accacattca aggtcacgca tcattacacg acgtaatacc tcggcatccg gggccttagc 114060
atcagcaatg atttgagcca gttcttcaat agccgcatta cccgtaatct tacgtgtggc 114120
taatgtgaat tcagcgaaat caagaaggtc ttcaagagta atcataccaa aggattgaga 114180
tataaatcca ggttctggcc actttttaat accgtagttc agacgacggg tataagccat 114240
acgataaaca cgtttcagaa gctcattgtc cttttcacga gcaataatgg cttctttagc 114300
tttagtagaa tcgatagcag caatttcgtt caagatatct aaaatcataa tcacctcatt 114360
agtcatggat tctattataa gccacatcag ccaaaagcaa gtctaatcgc ttatgataag 114420
agaacacaaa tctcattcgc ccatcggatt tgaacttgga cataaagtgg acataaatga 114480
atccctgttc gacgcattcg cgccaaacag gatggtcttt agccggattt acatcaaatg 114540
agtaatcatg attcacatga cgaataaact ggtttacatg accataatcc attgtagtgg 114600
taggaccata gtctgaaatt gtatgaacta caaacatatt aacctcgcgc aatccattca 114660
actgcggcat tattacgaag ggattcgatt gctgctatat cgtcccatga attaaccttt 114720
acggccaaat taggtttaaa gtcacgttca ccacgagcta accaataaac ttggatatcc 114780
atgagaacat tagatgcggc atcacagtga tgagccaaat catcaacata aaacttaata 114840
cgtttgccgt acgtattttt agctctaatg aacaagtctt cttttgattc tgaatgtcca 114900
cacatcagaa tctccttgaa tgcgccaggg aacaatgcat tcaaattgaa ttgtctattc 114960
agcagggcat caattgagtc gcctagcgca gtcacggcta caaaatcgaa gtctttttg 115020 agcctgttga tgtgttttaa tgcgtccatg taaggagaca gataacgaat aaaatctgac 115080
tgattatatt tctcgattaa acgagcgcct aattcgttgt cacaattaaa cagctcacca 115140
ggagataaga aacgttcgtc ctgaatcata ttcaaaatat gttctaaagg caaattatat 115200
ttctgtgcga aataaggcaa gccagactgc caacttaaac atactccatc gatatctgtt 115260
aagataactg gtttcataat aaatctctca atttgtttag gatgtcgata aactcttttt 115320
cagttagtat tgtatcacat tctgtaaggt ggcttgccat agaatgcttt aaaaccctac 115380
cttttgtgga ttgtaacgca tcgcgaaatc ctttgttttg gagcgctgct tcaaaatacg 115440
cactttcgta aagctctttc catgcttcgg aatatcttga aaacggagtt ccaacccaga 115500
acaacgtgcc acggtcctga gctctagcat aagctcgtcc agctttttgc gcgtccaacc 115560
cggacatccc aaatatacgt ctttgttgtt catgattttt caccttacac ccttggagga 115620
acccttcgag accaccaaat tggataccat ccataacgaa aggccattta gcaaagttac 115680
ttaatgcgca tgatggccat gggaaattgc ttctgatttc taattcagac atctttgaca 115740
cttataattt caacatcagc ccaatgacca taaccaggta gacggtcttt aatagacaat 115800
ccaccgtcag atttcagcat tttaattgtt ttagtatatg gttcaatatt tcgggcccat 115860
ggactcacgt ctgttacacg ataagtaact tcaaccattt ctgttcccaa aattttctga 115920
atcagtttct taaacatatt atcctcgctt taaacatttg attacagaca gttcaccgcc 115980
catacgaaca tcttcagttc catcgaccca taggacggtg taggcttctt taatagtaac 116040
attacctaat ttaaaagcag gtagaacctt tgaaatcatg ccaggaatac ctataccttt 116100
taactggact gtttgtgata agaatagttg cattagaacc tcatctgaaa gccatgtgat 116160
ttaacattac caccatagat gtcggacgta ttgacttcac gtgcagagct tgggtcgata 116220
ttgatatcat ggttgagctt agtgattgct agggtatcac gaccattaac agtacggaat 116280
tctaccgggc atacaacatc ggcgtaagcc ttaatagatt cacgagtggg ttgtttgtcg 116340
gcaggaacgt ctttacctgc tttagagaaa acaacttcac agaaattttt acgagtatca 116400
aaataagtgg tcataaacat aatattttcc tcaaaggagg ccgaagcctc catttttaag 116460
attagatatc gaattcgttc agaactacat caaagattgc ttccaggtgt tcaggtttag 116520
ctcggttgct caggatgtga cgaatccagg ttttaaccag aagcttacga ttaacgccgt 116580
tccagcaagg atgggtacct aaatcacgtt gacggaaatc atcatctaaa gcgattttaa 116640
aagtagaacc ttccattgtg attgaaaccg taatgccgtt ttcaaagcgc atataaacgt 116700
agttaggagt catgcactgc tcgatttcgc acactgtacc gttgttgtgt ttccacaggc 116760
aaataacttc agaagaacca gcgataccgt tagaaacata tttacgttcg aagttgatgt 116820

-continued

```
agttcatttt attctccagt ttgttttcgt attatttggt acaggtctat aataacacaa 116880
cctgtaccaa agtaaaacat ttatttcaca acattccaat ttttcatatc aagtttacca 116940
acttttttca tctgagcaat cagacgttca gcacgtgtac gggcattaac gtaatagaat 117000
tcaccaattt tgttttcttc aatacgaccg gtaattacag ttttcagttc ataaatccaa 117060
cctgtaaaga agttgtgaag ctcgatggtg aatgtgaaat cagtacccat accttcagtg 117120
gtttcgactt cgatgatatc accttcaact gcagtcagga cccacatggt ttcttgatat 117180
tcaccgttga aacatttagc tttaacagat gcattaagat ttacagtttt cattttattc 117240
tccagtttgt tttcgtatta tttggtacat gtctatagta tcatgcctac tggagatgta 117300
catacttttt tgcaaataaa acgaaaaaag gaacccgaag gttccttact taatgatgat 117360
acgaggatta agctctgccg tgtagtaatt tacagcctta gtaactatag cttcaccttt 117420
aggatttgcc agaacccatt cacgggctcg tttgtgagct tctaattcag tcaataatcc 117480
ggacctttga caccctctgt cttgggtacc tgcttctgtt aaaaaagcaa ctaggtaaat 117540
cgcgttttca taaggcttgg cgggcggtac gtatactggc gggttatatg ccgcgggatg 117600
atgtgccgga attccatcat acggccctat acctggcacc gcgtaagagg caccgcgcgg 117660
agaagtaaat gtatgattat atctatcgtt cataatattt cctacaaaaa tgggactccg 117720
aagagtccca taacttatgc ctgaggctta ccaaagcaag cagcatctgc acgtagtaca 117780
gcacgagcac gagcttgaag tttttcaacc aactgattga tacgtgcgtt agactcacgc 117840
ttgtagccag cgcgtttaga ggtaccatca attactttaa cttctttctt agccattttt 117900
aaattctctt aaattagaat gaaggactta ttgacattgc cttcgcaagc cctctatggg 117960
gtacttaggt ttcggatatt taacgacagg ataaccataa acctcgtcaa cattcaagag 118020
gtacaccgta aaattgtcgg ggcggtactt ctaaaacata ccgattcgta aatcgataat 118080
cagacaattc gacggctcct cgattttact tcagggtaat aataaaatga cgtactgctt 118140
tacgagctgc tgaagccaaa ggcttagcaa atttcagttc atctttagct tccagttcag 118200
cagccagagt agcctgagcc ggattcagat gtttgaaata acgcaggatt tccagtgctt 118260
cggcttcaac atcaatagag gcgccgtagt tttcgtgacc gttgttccaa gcgttgcgtt 118320
gcagttcaag agcgtgattc agttgtttgt tcattttagt ttctcaattc gagataaaga 118380
ttggtggaca cgttcgtctc agtattccag ctgagttgta tctcgccgta tggaagaggc 118440
taaccccata caccaaccga agttctgtat gacatcaacc tcttcgtaat tttatttata 118500
caagcaagga attgctttat agtggcaggt aacgaatttt tgtttaattt ctttaggctg 118560
tttaataccc aatgcaacta aaggatgagg cacgttagca atcttaccaa caggaagtgg 118620
agtcaaatcg cctacttcac aaaaaccttc agggacatca ggtcctacag aataaatttc 118680
acaaagttca gggatttcac cttgatgaag tttgccaata acgataccag atgcagtagt 118740
ttcttcatca ccagcttgtt ttggttcgga aacgagaata acatattctc cgaccgcttt 118800
aataggaagt tccatattta atccatattg ttttgttgat agattaataa taacacgcta 118860
ttcttaaagc atattatagg acaagcagag tttcggtctg aaggccatta acagaaatca 118920
gcttatcgaa acggaatgaa cgccaatcat taaccttggt atcaaatact ctgatataat 118980
taacaggttc tttattggct tcaggtccag gggcctggac ttctttatat ggaagcaggt 119040
ctaagtcacg tgtacaagtc atacgacggg cactaccatc agctttttca aacaggactt 119100
cgtgagtacc tacagacaaa atagtcttga ctttttcacg gagacgaatt gtttcttgtt 119160
cagttaaaat cataattatt ccagaatagt tttgatagtg gttgcattac gctcttttag 119220
```

```
agctcttaat aggctatggc aattttcaag aataggtact gttttgtagt tcatgttggc 119280
ataaacccac tcagatttat agtacgattt ccatcgagag aaaaagtact ttttatattc 119340
tactgaatag gccaccaggt tttcaccttt tgagttcaga cctgaaaact taactagacg 119400
aaatttcatt attcaccaca atagttttga attgattccc agttcaaaga acggagacct 119460
gtacgattat actggataac ttcgatgcct gattcacgga ggatatcgtc ccacccttca 119520
ggatttcggt catagagctc agcataaacc aatgttttaa ttccagactg cgcaatagac 119580
ttagcacaat cagcgcacgg agataatgtc acgtacatcg tagcgccatc aatagaactt 119640
ccggtacgag cagcaaacaa aatggcattc agttcagcat ggatttcatt tttagatgac 119700
catgcagcgt gagccatacg gtgttcttta agaagaacag atttatgcga cattcgagcc 119760
gggtcataca caacacgagt ccagttctgt tccacagcat ggtcacaaca gttaacacca 119820
ccagaaggcg aaccgttata ccctgtagaa ataatgcggc cattcttttc aataaccgcg 119880
cccactttcc atgaacaaca ttttgattct tgagaaatca gatatgcaat ctgaagatat 119940
gtgcttgctt tcattctacg tacactcgct gtgcttcgac caaaccatct gaaccgagtt 120000
tcaactgggt aatttggtcg ccatttttag gattaacgat aaccaatacc gcgcgtggag 120060
attcctgaat tactcgcaga gttgcatcag gaaaacgtac agaaacctta ttaatcaggg 120120
cctgagcaaa ttctttaact ttaacgtgaa actgctctac agtaataggt tgttcgctca 120180
gcattagatt gtctccaact taagttgttt ggtagtggta gcttgggtaa cgtcgccttt 120240
aacaatataa cacacttgtt ggaacgaact ggtcaaaagc tcttcagcct gacgatcggc 120300
ttgttccttt gtgttatggc gagaatgaac ttcaatctta ccatttttaa caataagcac 120360
tttccaatcg gccggagttt taataggttt gatttcaggg ttctggaaaa ctaactgcag 120420
ttctttaggg tctaccactt cgataaagta ttcgaattca tggctaaaaa agcccgctga 120480
attaaaaaga acactatttg catcgtcagg attacccgtg attttgctca ggtcgacaaa 120540
catcatctcg tcatatacac gaattcggct tacacgttca tgaccattat gataatcaat 120600
ttcaacttca aacggattca tacccacata cttagcaaaa gctgtattga ggccataagc 120660
accgttatta gtgaatttgt ttttggtgta ttcaccaacg aacttgtaaa acttacgctc 120720
ttcaaagaac ttacccattt cgatttcctc atttgtttcg gtaaggtcat catatcaccg 120780
tccttggtga aagtaaacac cttttttttaa atagcttcga caactaccgt ttgtttctgg 120840
aagtccattt tgcatgaaat agccaaaatg tggttatcaa ttttaaatgg aacgattgca 120900
aatgctgcac cgggcgtgag ttgaacagtg attgcatcaa ctgcatccgg gaacatgatt 120960
tccagaatag cagacaaacg accatgtacc tttagttcag tcgacgtgtc gacgctttcg 121020
tatagataat cagatacaat ctgactaaaa actactttaa caatttcaga ataagtaggg 121080
aacataatta cctcagtgta cagtatggac tttaacgtta acaataaacc ggtcaacgac 121140
ttcagtcaga ggaacaaact caacatagta ctcgcctttg taacgttcat tgaggtcatt 121200
acgaagggcc gcaagtgagt taatgagggc aggagacata ttcagaccta ccagtttctg 121260
aagctcttta taagcttctt cttcaacttc atggtgtttg ttatacataa tgttcttcca 121320
agaaggcaag gagttcagga gcggatttaa aaataccacc atcgaccttg tcttcatctt 121380
tatagtccat aacatccagg ccaatacgtc catcagttaa aggccatacg ccgaagaaaa 121440
agcatttacg tttttcaatt tcttcgattg tacgaaaaat cttttcgata ttattcatta 121500
aaagtcaccc gctgcgactt gccaacattc aacaccaatg cgccgccaca tttccactac 121560
```

ttgggtacgg tcatcaatag ctaatttaac atcaaagtgt ggagcaattt tttcccagaa 121620
gatttcttct ttaacgatgt catctttacg gtcgtcacct tgttcgcgtt gacattgcat 121680
gaccaatggt acaccagcaa agtcctcaac ccatttgcga gtcatacgat aatatttcat 121740
tgggtcttct tcagtgccac attcgcgacc gcttactacg ataatctgat aacccatatg 121800
ggcatacatc ttagacagtt caactaccat tgggttgatg acgtcagtat cacacttctc 121860
aaggtcgtat ggactacggt ccgccatttt ggctagtgta ccatcaacgt caaaaataac 121920
ggctttaggt ttgccaggag tccctgtata aaccggaagt ccaagataag cccgcatatg 121980
actatacatg gaacgcagaa cgtcaatagg tactgctttt gaaccacggc gactgttacg 122040
tttaaccagt tcagtccaag gaacatcgaa tactttatat tcaacttccc agccatattc 122100
tttagcaaag gttttccaca tcaaacgacg ttcaggattc aagttggtgt ctgaaataat 122160
tacgccctta acagaatcac caccatacaa aatactctta gcagcatcga actgcatgca 122220
agtcacgatg ccttctttct tcttggagta tttgtattca tcacgggctt catgacccat 122280
gattgattgg cgatagtcat cacggttgat gttaaaataa ccagggttct tagcaatgaa 122340
ttcacgagtc catgtgctct taccagaacc agggcaacct acagtcagaa taattttctt 122400
catcatttaa ttcccaacag agttttgagg agctgaatgc gtaattcaac acgcccttta 122460
tttaattcag ctactgcctt gttgcttgac ttgcgacggg tattggcaga gatgaacata 122520
attaaatggt tctttagctc acccatatcc acaccttggg ccttagcagc cttccgcaga 122580
gccttgcctg catcatctaa ggcttttgca gggtcttcgt cattcaagac caatccgcgg 122640
tctaaatcca tatatacagc gccatggcat gaatcaatat aattgtcgga gcacttgata 122700
taattctcta ataactcttt catacaccga gttccttata aagttcttca cggcaagttt 122760
taagagtttt acctgattcg taagcaacac tttcaggaac atcgccaagg gttactgcgg 122820
attgcatttg accatggcgt ttagccgcat attcaaaact tttcactagc tcacgaatac 122880
gttctttttc attgtattct tcaatgaatt cagggtattc ccaaaccgga cgcatcatac 122940
gataccattg ttggatggtg atataattac ttccatccag attaataatt tgcgaaggct 123000
taatagaccc tggagcataa aaagttacct gtcttactac atcaataccg tccaccatag 123060
cccaagcaaa atcgaaagtt gccttctttt caagtggtgt acttgcacag gaccctagct 123120
taaggagttt ttgtaatgca ggagatttaa cgcctgaaat gtactcagga ttagccacaa 123180
aactgttatc gcgtaaagtc ataataattt cctcaaattt tataatccgt aggagcatta 123240
tactctgctc ccaagagttt gtaaactact ttccaaaaag accatcaata cacatactga 123300
acgcaatccc gaagcaaaag aatgcgatag ctaatctaac ggcatcccaa ccaagactac 123360
actcaatcat ttgcacttct cctcttttag tccggaacgg taataacata acatagattt 123420
ctggtcttgt acatatcttt ttacgtcatt caaccaaata cgatgttctt gggaatcttc 123480
aaatggcatt ccaacccaag ctttaccatc gattacctta acctgccatt taacattatg 123540
ttcggcaata ggttgtggcc atgaaggatg cagttgttgc ttaggcacta caggaagctc 123600
ctgagcacat ccggctaata agccaataga taatactact acagataatt taatcattct 123660
gtaatgctcc tgaagtcttc tgtaaaggaa tcgaaggact tgttgatttg tttttcgacc 123720
agtcctggct tacttgccac cacgtgcgcc ttcttcgaat ctttacggag cttttcattt 123780
tctaccttaa ttttatccat tcgggcattc atttcagtag tacggaattc aatatcagag 123840
tattgaccac gaaggtcatc tacggcttcg gcattctgtt tagccgtttg ctgggtagtt 123900
ttcagttctt cagtaagggt atcaatacgg cttgattgat acgaaataaa accgtaagca 123960

```
cctactgcaa tggctccagc taaaaggtaa atacttaatt tagacatttg gtaataatct 124020

cgatgatgtc atcacgtgac agggaattaa taagaaccgt tttaggattt tcgcactgaa 124080

ttttgtacgt ttcgaacata aaacacaatt cttcagcggt atggtaagga cttgaaatgc 124140

caaggcgatt aaacttgtcg cttaatgggt cgcaaatcaa atagaaagtg atgcctgaga 124200

ttttgacatt aggttggcta atattaatga atacctcggc atcgtacttg gaaaggttgt 124260

tttggagaaa ctcaaccata gagttgacag cttcaggcat ggcttcacgc ttttcttctg 124320

cataacgggt agagtattct ttttgcttga ttttcttttt agcattttta gctaaagtac 124380

cacgaagatc ggtcaggtaa cctacggcac gagaaccttt aaaaacttgg ataccgtcag 124440

tagagtcacc aaaagcctta acaaccattt cgttagtaat catttgcata ttcattttgt 124500

tttctcctca ttagttggta agtctatact aacacaacat gaggagatgt aaactactct 124560

accacaattt ctttcaaata tttttcaggg atttgggctt tatggttttt caagaacaca 124620

gagttaatct ggtctacaac cgtatcataa ttaataccgc ctacgtacgc ctgcataaga 124680

atagagaaca accctgggaa gtccttaagg attagctgtc cagtaacggc gtagtcttta 124740

cggtcgcgtc ccttgagttg ggaatacgct gcttccaaca aagccagtga ttgttctaga 124800

taatctaaat gaatacgttc aaaggcatcg attttctcta tagcaaacga atccgtactg 124860

aacaggccac gaaggtcgtc agttccacca gccactacaa cttcaaacaa acgttcgtta 124920

ttgttaatgg aatctttggt atgatgcagc gcactgtacc aagcggtttt gagtttaaag 124980

aacgtaccat ctttcagtac aaagatgaaa ccttcaatac cctcttgttt acggatgttt 125040

tctacgaaat caccttcaga gagttcatag cttttaacca aatgcttacg cagtgcgccg 125100

tccttaaaca gttcggcgta tggaatatat tcacctgttt cattattacg aacgttcaac 125160

aggatgaggt ttgtttcttg gtaagccaga acgatacggt tagtaggagc gacgtactca 125220

aggttgcatg tatatcctgc tttagtaatt tcttctaaac gggcagcgaa ggcctcgttt 125280

tcagggagac gaaggaaacg taaagaatca tgtaccattg atgaatggat agagccttta 125340

gatttaacag aaagatattg tctgtccatg aaggtagaaa tcaaggaacc atcttcctta 125400

gccattacga ggtcaatatt ttccggcgac aaatccagac cgatagtcat agggttttcg 125460

tcaaggttaa agaacttttg cataggacga gcagcaatac gtactggacc gttctcgtcc 125520

atttcaaaca taatgcctcg acactctagt gcgccgtcct ccaaccaatc actgtatgat 125580

gcatagttat aactaaagat gcgatagttg actcctagcg cactctgaaa gtctttaaag 125640

aagaacttag atttagtcga gtttttaacc agggccatca agttatcata taattcaatc 125700

attgcttatc cttttaatcg gtgttgggta ttccaaggtg gattaaattt ctttatgaac 125760

attggctctt caagagacat ggtctcaact gacatagttc caagttcgtt agtcattgac 125820

agattaaagc actgccgtgc atagaactct acctttttac ctgccattaa tgcttcatga 125880

atcagaatgg acttagtcga atctgacgtt tggtccttac gattaatagc ggttcggtag 125940

tagttgatgc gcttacgaag atttttagtc ttcccgacgt agactagtat atcatcaacc 126000

gctatagcat atatgacatt ttgtttattt ggtactgtga gtggagctat ggtggcgtca 126060

tcttggagtt ctagggtgac gtacttgata aagctaaatt cgtctgcgat ttctttcata 126120

gcaataaggg gccgaagccc cattccttaa aaatatctct tgtacgatgc cattactttt 126180

tcatcgacat cgttatcaat ttgtgctaca aggtaagaac tgatttccac ttcctgagga 126240

gcagcctgta cagcatcaga attcaggtat tcgcgaatcc aaggatacgg atggcgagta 126300
```

ggagcatcag taataggaca tggtaagccg cattgtttca tacgagaaac cgtcaggtaa 126360
tcgacaaaag cacccatgtt ctgagtattt aatccagggc aagtaccatc tttgaacagg 126420
tgagcggccc attctttttc ttgacggtta acttccatga aaatatcaac tgcttcttgt 126480
tcgcactctt gggcaatttt aacccattca tcgccatcag taccaagttg aagttgacga 126540
ataatgtact gagtaccttt aaggtggagc tgctcatcgc gtgcaatgaa cttcataatc 126600
ttggcattac cttccatgat ttccatgttc ttatggaagt taaaggtgca tgcgaaagat 126660
acgtaaaaac gaatagcttc caaggcgttg attacgtgca ggcagaggta aagagaacgc 126720
attagttcat atttggcagt tttaacacct tcactgaact catggtattc ttctaaagca 126780
ttttggtatt tacgtgtttt ctcaataaca tcgtcgtaat aacgaccaat ggattcggcc 126840
cgtttcatga tagcgtcatc taacagaatt tcatcaaata ccttcgatgg gtctgtatag 126900
aggttgcgca tgatatgagt atatgaacga gagtgaatgg tttcactaaa tgtccatgta 126960
gccacccatg tatcaaggct agggtccgaa atcaatgctt ggagtgcagc agaaggggcc 127020
cgtccttgga tactgtccag aagtgattga tacttcaggt tattggtaaa aatattttgt 127080
tggaattgtg gaagcttatt aaactgcgcg gcatccatca tcaagttaac ttcttctggg 127140
cgccagaaga aactcaactg cttttcacaa agctcttcga atactttatg gcgttggata 127200
tcgtaacgag caatacccaa tcctgaacca aagaacatag gttctgttaa aacatcaact 127260
ggggtggtat taaaaactgt agacatatta ttctcatttg ttagtgactc atccatgagt 127320
caattataat cagagtttct taaagcttac aagctgcaca atcatcggct ttaggggttt 127380
cgatttcata gtcatcggta ccggagccat cacgggtatt atgataatag agattttttc 127440
cgccataata ccagaaatat agcaggtcgt caagcattac agacatcgga acttttcctt 127500
ttggaaaaat ctgtgggtca taatacgtgt tagctgatgc agattggcat acccatttca 127560
acataatcgc cacttgggta agataaggtt tattaccttt cttagcgagg gtccaagcat 127620
aatcatacag cccttggtta tgttctacat taggaactac ctgacggaag ttaccttctt 127680
tagattcttt aatacttacc gggccacgcg gaggttcgat accgtttgta gagttggaaa 127740
cctggctgct tgattcgcat ggcataagtg ctgataatgt gctattacgg atgccatgtt 127800
tagccaagtc ttcccgcaac gacgtccagt cacaaacgta ttttggagct gcgatttggt 127860
caattttttt attgtaccag tcgataggta attcgcctcg agaccattta gtgtctgaat 127920
aatactcgca aggtcctttt tcttcggcca gcttgattga tgctcggata agtccatatt 127980
gtaatctctc aaacagttca tgagttaaat cgttagcgtc ttcataagaa gcaaagtttg 128040
aagccaacca agcggcgtag ttcgtaacac ctacacccag gttacgacgt ttcttagcct 128100
tcagagcttc aggaacagga taatcttggt agtccaacag gttatcaagt gcacgtacct 128160
ggacttcagc aagttcgttg attttgtctt ggtcttgcca atcgaagtta tccagcacaa 128220
atgcagacaa cgtacacaat ccgatttcag cgtccgggct attcacatca gtagtcggga 128280
tagcaatttc acaacacaag ttgctctggc gaataggagc tttctcacga ataaatggtg 128340
tgaagttgtt agtgttatca acgaattgag gataaattcg tgcagtgcct gaacgttcag 128400
tcatgaacaa ttcaaaaagg tcacgtgcct taatacgttt cttacgaata ctagggtctt 128460
tttctgcagc ttcatacaat tcacggaaac ggtcttggtc ttcgaaataa gaatggtaaa 128520
gctcaccact catttcatga ggactaaaca gagtaatgta atcatttttg ccgaaacgtt 128580
ccatcatcag gtcgttcaac tggattccgt agtccatatg acggatacgg ttctcatcga 128640
caccccttgtt gtttttcaga acgagcagat tttcaacttc caaatgccaa ataggataat 128700

```
aagcagtagc agcgccgcca cggattccac cttgtgaaca tgatttaaca gcagtctgga 128760
aatgtttcca gaacggaata acaccagtat gtttgacttc acccatgcca atacgagaac 128820
cttcagcacg aatcatacca acgttgatgc caatacctgc acgtttagaa atgtattcaa 128880
ttattgagtt agcagttttg ttaatagatt tcagtgagtc gcctgcttca ataaccacac 128940
aagaactaaa ttgacgggtt ggtgtacgag cccctgccat aataggcgta ggcaacgaaa 129000
cctgacgagt acttacagca tcataaaaac ggatgatatg agctaaacga ttaccaggtt 129060
cttcttggtg caacgccata ccaatacaca taatagcgaa ctgaggagtt tcgtagattt 129120
taccggttgt tttatcttta accagatatt tctctttaag ctgcatcgca cctgcatatg 129180
tcaattcaaa gtcacgttca tgcttgatat gagattctaa gaaagtaatt tcttctgcag 129240
aatatcgaga cagcaattca gggtcatatt taccttcgtt aacacaatag gaaatatggt 129300
cgataaaact acgcggttca aactggccgt aaacttcttt acgaagagca aacatcaatt 129360
gctttgcagc aacgtattgg taatcaggct cttcaaccga aataaggttg gctgcgacct 129420
taacagtcag attctggata tctttggtag tcataccatc acgaagatga gatttgattt 129480
cttcgtataa ttcatagggg tcgatttggg ttccttcaca gccccaagtc agaactttaa 129540
taatttttttg tgcgtcaaaa tcttgggata caccactact tttttgtact tgcataattt 129600
cctcaatatg ttaggttcta caattattct atcatagaac ctgttaagca tggactgata 129660
tttatagaat gaaattcagt ccgaccataa taaccaaaaa cagagtacag attatttgaa 129720
ttttcatata gccatcttag ccttaatagt agggtgtgat tcgtaacctt taaggacgaa 129780
atctttaggt ctaagtttaa gaacatattc caattgttct ttagtagaaa gatggcggaa 129840
tttataaggc aatccaccta ttaccagttc acaaagctct ttaggttcac ggcgcaatac 129900
ttcctggcat tgttcaacat ggttggaata gatgtgcgta ttgccgcctg agaacactaa 129960
atcacctgga ataagattac acatcttagc tacgatatgc acaagagcgg cgtaagaggc 130020
gatattaaat ggtaatccta agaacacgtc aacagaacgt tggtaccact ggaggtcaag 130080
gtgaccatta cgaacgttga actgataaaa acagtggcat ggtggaagag ccatcttatt 130140
aatttctgct gggttccatg ctgatacgat ttgacgacgg tcattaggca ttttcttaat 130200
gcgttcgaca atctctacaa cctggtcgat accaccaaaa tctcgccatt gtttcccgta 130260
cacaggaccc agttcgccat cagaatatcc caaatcaatt gcttgatttt catagttttc 130320
gtcccaaata gttttacctt cagtacgcga gccatgagta cgttctctga ggtcattaac 130380
attagtcgaa cctgacaaga accaaaggag ctcagcaata caggctttcc atgctaattt 130440
tttagttgtt accgctggga agcctttagt taaatcaaaa cgtaatttag taccgaacag 130500
ggcaattgta ccagtgccag tacggtcgtc agtttcgtag ccattttcca ggatatcttt 130560
aattaaaaat tggtattgtt tcatttgtat actgtttccg tcagtgtagt aagttcgtct 130620
attttatacc aatgggtttc aagcatttca cgttgacgaa tttcatgaag gaagttttct 130680
tccaattgaa ccgtagagtt aacccgatgg catttctcaa tacgagaaac aactacttca 130740
tcagcataag gcaatgctgc atataacaga gcagggccgc cgattatgct tactttagag 130800
cttggtccaa gcataggttc aaagaacgta ttaggacttg atacttggat ttcaccacct 130860
gtaataaagg ttacgtactg cgcccatgtg atatagaaat gagcgaaatc accatcttta 130920
gtttcaggat aatcacggtc aaggtcacaa actacaatat gactacgtcc agggagtaat 130980
ccaggcaatg attggaatgt cttagcaccc ataatcatga ttgtgtcttc agtacgtgct 131040
```

ttaaaattct gaaggtcctt tttaacccgt ccccatggaa gtccatcacc tagtccaaat 131100
gcattttggt cgataccatc aactgttttg gttggagaat aagcgaacac taatttaatc 131160
ataatttcct cacgctttct tagcgatttt ccagtctgct ttaaattggt caacatcaga 131220
gtggtgaatc cagaaaccag atgagctacc atcttcataa agaggacaac catcacactc 131280
atctttccaa cccatcgcac acaaagcctg ttcagctttt tctagagctt ccggattatt 131340
accttggatt gtgaagtacc atttgccttt aacttcagaa tcgttgattg attcacgttg 131400
taatttcatt ttattctcct caagttgaca aggctatagt atcactacca tagcctgagg 131460
taaacttatt tttgaatcaa gcccatataa aattcagcat cttcggcatg cataccgtca 131520
caatactcgt cagccataaa gcgggtaagg tcttcaagag gaccttggac ttcaatttgc 131580
atactacaga attgcgtatc tttaatatag gtcataacta aagaaggata acgattacgg 131640
ataacttcat aagtgtattc aaaatcaacg atatcgatat taaccttagc cattttattt 131700
tcctcactcg ttagttgata ggtctatagt atcatgttta aaggcattgt aaaccattaa 131760
atgccaaaaa agggaagacc gaagtcttcc cattataaat caataactta tagaccagct 131820
aacaggtcgt ccagaccatc gtcatcagaa ggacttactg acggctcagg agtagtggaa 131880
cgagttggtg tagacggttt ggaatcatat gcatcaaggt ctgcactgaa tgcgtccagg 131940
tcatcaccaa tcttgtcagc ggctgcagaa gctttagcgg cagcaccacc aagagcagct 132000
gtaccaacaa ctttcttaaa cttggcttcg ttagtttcga atgatttgaa atcaagcagt 132060
ttagaaaggt cgtgcatttc ttccatcaat ttagcttggt aagcttcatc attgatgtta 132120
ggaatttcag actgacccat gaatttggaa tcgtcgtagt tcttgaagtc gccaactttc 132180
ttagatttca gtacgaagtt cgcaccatca aacggacatg ttacgtcaac cggcacttca 132240
ccaatatcag tatcaacttc aaccatctgg ttgattttat ccataatttt ctgaccgaaa 132300
cggaatttaa acactttacc ttcgttagca ggcactgcac tatccttaat aacaaggatg 132360
ttagcccaga aggaagtttt acgtttcatc agtttgtatt cggcattatt agtattaaag 132420
gtatcattct ggttcatgta tttacataca ggacatgaat cgaaatcgcc gtgagtagac 132480
gtacatgatt caatatacca ttgaccattt ttcttaaagc cgtggttaac aagtttaata 132540
aatggcgatg ggttagcttc gtttttcgaa ggaaggaatc taataaccgc tgtcccgaca 132600
ccattgtcat ctttcaattt ccactctgat ttatcatcgg aagagaaaga actaccacct 132660
ttaagggcat taagttgggc ggcaagctga gaagggtcac gacgtttgaa catagacata 132720
ttatttacct tatttgatat atttaattaa tttattaaca gttggtgtta tcacatgtac 132780
cttgataact aggttttgtt gatgaagtaa ttatatacta cttcatgtta agcattttaa 132840
tttaataaac tcagggtctt cgttaggaat ccatccttta ttaaattgtt taatcatact 132900
tttagctgtt gtttcactaa cagaaatacc agaacctata agacgacgcc aaccgcacgt 132960
tcttccttgt gaatttatta taatatattt attataagca atatcactaa gtttccaatc 133020
attaggattt gctctggaag ttttccaagg gcgataatca ggttgattca tgtaattaga 133080
agctttcata ttagctctaa cttcagggcg tttagccgga tgggtatgtc caaagactcc 133140
aaatcctccg ccggtgtaaa ctaaattaaa ataatcatcg ttatctctag cttgaacttt 133200
caattgttca gaacgttcaa tattgataac aatatcaaat ggcgttatag ccaaaatttc 133260
gactataggc ttttcttctt caatggctct tttaaatctg ggttgttcgc aagaagtcca 133320
atactcttta cctttacaat caaacattac accattttca aaagtacaat tagttttaga 133380
acctatatac aaaaatggtt taatgttatc actttgcctc ttaggccata tcattttata 133440

```
tactatattc aaaatttaca acccttaatt gtttcaatga acaatttacg agcttctaaa 133500
ttatcgatta taaggatttt cttataagca tttaatttag tcgaatactt agaccacact 133560
aaatcgttgg tctgttcatc atgtttattt attatatcca taaatgaatc aagcaaaata 133620
aacgtttcga atgaaataac attcgactga aggagcttaa aaatatagct cgagttaact 133680
tttttattat aatcaaaaat ttcagaaagc gcttgaactt ccactttctt actaaaataa 133740
taaatgtttt ttatatcatc ctcaaaaact tgttttattc ttttaagtct accgatatat 133800
tctcggtaaa agactaaggc gtcagcatca ctgatgtcgc caatccatgc gtcttggtta 133860
gccaccaagt tactcatgaa gataagagca agctctttca aagtgtattt atcactcaat 133920
ttctcaaaga aatatttgtc acgacgtttt tgataagccg tatcggagat tcgcatgacc 133980
cagttatatt ttataacgtc gtatttggcg ttgaagtgat gtttgagcat taagtatagt 134040
gaatatacgc tcttaccatt caccatacgg ttattgtttg gtggcatgcg aatcttaatc 134100
ataacaagaa atccagggta ttagtctttt gcgttcgggc cattgaaggt cgaagcaagt 134160
tatcatcaat ggcttcgttc ataattttat caataattcc tgcaggcaaa taacgagcaa 134220
agttaccttc agggatgctg ttctcttcca accatgcggt agccgcttcg aggtaactac 134280
aaccttcagc ttcaacaaag gcctcaatat caaggccgtt ctgttgtttg tttaccaata 134340
catggacagg ttcggaagcg gtattaaccg ctccatcaaa atcattcaaa gattgtgtca 134400
tacagttcta ccacttcagt tttttcgtct tcgaaacgtt cacgagtgcc tttatggtac 134460
agggagaaca gttggttaaa cattttaccg tctacaccaa gttcagtctt agcacggtct 134520
ttgatatctt taatttcgtc accgtaagct tccattttta atttagtatc ggaagccgac 134580
ttaatcaact gagcaagggt attgccatgt tcttcttgat tgaattcaac tttcactttt 134640
tctttagcca ttatattcac cttaatagaa atcagctact gtagcggtta gtttagacaa 134700
accagattta acgaaataag gataaacttt agatttcgaa ggtttgttat acgtattata 134760
tctttcagta attaaagcaa caatatcatc tggaataaag tccatatcga ttaagatttg 134820
gttttcacag aaacgttcat attgttcttc agtaagaagt gttttaatta tatcatggtc 134880
ataataatta agagcaattg cttcaagttc cttggcacga gtgctaggag tacgttcgcc 134940
ttcaaccatt gtcaaccagt aatcaccacg aactttaata ctcgcgacgt tatctttacg 135000
gtcaccttta accactttag ttacacaatc cagtaatgag tcaccggttt ttgttttaac 135060
gaatttttc tgcattggag accattgctt aacgccaggg aatttatgga gttgagtaaa 135120
gtcaccgtcc gaagaaccaa tcattaccgg atggcctaaa gccgtaagga tacgagtcaa 135180
tacagcaata tggtcatctg cctcgacagt atcgatgttc ataacaatat aaggcatgtt 135240
atgttcgagc tcatcaataa tcaaatgcat tgctgtgaat aaaccttccc aatcaaataa 135300
tgattcttca cgagccttgg cacggttttt cttataataa gaagaataac gacgacgcca 135360
ataacctgat ttagagttat cgacacaaat gattaattgg ttgtaacctt gtttttaaa 135420
gtctttaata tttttcttaa ttgaattcaa cacgaggtgt cgaagcattg ctgtagttac 135480
tttaggaaat ccggcatttt caccaaattc ttggaatgcc gcagccataa tgatttggct 135540
aaagtctaac aacaagaatc catctttttg acgttcttct tcaggaagta aaaaatctaa 135600
atcgttcata tgaacctctg tccaattagt gtagaggttc attatatcat gaccctagaa 135660
gaagtaaaca ctttgctata aatagttcta taccctgaaa acgaaaagga aataaaatgg 135720
ctgatatttt aaaacctgca ttccgtgcta catccggact cgatgctgcg ggcgagaaag 135780
```

-continued

```
ttatcaatgt tgccaaagcc gattacaatg tattagatga tggcgtcaac gttgaattct 135840
ttatagatga gaacaccatc caggcgtacg acgagacgcg cggatataag aaagggtttg 135900
cagtaatcca tgaccaacgt atctgggttg ctcaacgtga tatcgatgcc cctgcaggaa 135960
cttttactcc gggctattgg actgctaccc gtaccgaccc taaatggatt accgtagcgt 136020
ctcctacacg ccagctggct tccggtgaat atattgcagt agattctgct gctagcttta 136080
ctacatttac cctgcctcct aaccctacag atggcgatac cgttgtaatt aaagatattg 136140
gtggacgtgt tggttataac gaaatcaagg tccaatctag ttctgctcct ggtggtggta 136200
accagaaaat tgttcgtttt ggtaatcagt ttactgagac cttaattaca aagccttttt 136260
cttataacat gattatcttt gctaaccgtc tttggcattt ctgggaagca ggtaatgaag 136320
aacgcggtat tcgggtagaa ccgaacatgg cccagttcca atcacaagca ggtgataacg 136380
ttctccgtcg ttatacttca ggtgcagtaa ttaagtttac tcttcctaag tatgcgaacc 136440
aaggcgatat gattaaaacc gttgatattg atggtttagg aagtaagttc cacttaatcg 136500
ttgaaacgtt tgatgcttca tcttcattag gtaagcttgg tcagcatagc atggaattcc 136560
gtacctccgg tgatggattc tttgtttata actctaccga aaaattatgg tatgtttggg 136620
acggtgaccg tcaaactcgt ttacgcgtaa ttcgtgacga tgttgagctc ttggctaatg 136680
aaagtgttat tgtttttggt cctaataata cgacgccgca gacgattaat atcacattac 136740
ctacaggtgt agcccagggt gatgtcgtta agattgctct gaactatctc cgtaaagctc 136800
agacggtaaa tattaaggct gctgtaggag ataaaatagc ttcttcggtt caattgctcc 136860
agttccctaa acgttcagaa tatccgccgg atactgaatg ggtattgaat gatgtattga 136920
ccttcaatgg taacttaagt tatactccgg ttattgaact gagttatatt gaagacacca 136980
ctacaggtgg caaatattgg gttgttgctc agaacgttcc tactgtagaa cgtgtggatt 137040
ctaaggatga tttaactcgc gctcgcttgg gtgttattgc tctggcgtca cagacccaag 137100
caaacgtaga ccatgaaaat aatcctgaaa aagaactggc tattactcca cagactttag 137160
ctaatcgtgt agctactgaa tcacgtcgtg gtattgctcg tattgctaca accgctcagg 137220
taaaccagaa tactggattt gcattccagg acgatttgat tatttctcct aagaaattaa 137280
acgaacgtac cgctaccgaa actcgtcgtg gtgtcgctga aattgctacg caacaggaaa 137340
ctgatgcagg tgttgatgat acaaccatta tcactcctaa gaagctacag acgcgccagg 137400
gaactgaaaa cctgtctggt atagtaaaat acgtatccac cacgggaacc actcctgcga 137460
cttctagagc aactgtaggt actaacgttt ataataagaa cacaactact ttagttattt 137520
ctcctaaagc tttggaccaa tataaagcta actatgagaa ccaaggcgct gtatatcttg 137580
ctacgcaagc cgaagttaat gcgggtgcta ctaacccagg ttttagtaac tcagttgtta 137640
cacctgaaac attaggtgct cgtcgtgcta ctgatactaa tcacggttta attgaaattg 137700
ctacgcaaca ggaaactgat gctggaactg attatactcg tgcggtaacg cctaagacgt 137760
taaatgatag gaatgctact caaacactta ctggtattgc tcgtattggt actcaagtag 137820
aatttgatgc aggtgtatta gataatgtta tttcaactcc gttgaaagtt aaaacaagat 137880
ttaatgatac tgctagaact tctgtctcag cagccagtgg tttgattgaa tcaggaacct 137940
tatggaacca ttatacacta gatatccgtg aagcaagtaa tactcaacgt ggtacggctc 138000
gtttggctac ccaaactgaa gttaatactg gtattgatga caaaacaatc atcactccac 138060
ttaagcttca agctaaaaag gctaccgaaa acgctgaagg tattatccaa ctcgctactc 138120
aggctgaagt tattgctggt acggtaagta ataaagcgtt tagtcctaag cattacaaat 138180
```

atatcgtcca acaggaaaaa tcctgggaag ctacttctgc tcgtagagga tatgttaaat 138240
taaccacagg tacagccact tgggaaggtg acgatactaa tggttctgtt gccaacctgg 138300
ctaaatttga agattccggc tttgctattt ctcctcttca aatgaatacg gcattaactc 138360
actatcttcc gattaatggt aaggcttttg attccgataa attagatgga tttgatagca 138420
cgcagtttat tcgtcgtgat atagcacaag atattaatgc taatatgaca tttaaacagc 138480
ctgtaagaat tgaaaacact ttagcggtta ccggtgcggt taatttgagt ggttctgtta 138540
cttcaaataa tactacgtta accggtgcta ctgcaatcaa tagcaattct actgtaggcg 138600
ctttgaatta cattgagttc acttcacttt cgcaaggctc gggtacttgg atctctcaac 138660
atgatagcaa tgttaaagct cctgtatttt taaatataac tactccagcc ggcgcatcta 138720
gatacgttcc tttaattaag caacgttata aagatggaac atttaccttt ggtacattga 138780
taaatgaacc tacctcaaat gatgaaggtg cttttattct tcattatata gatgcagtaa 138840
aaacccagag caaatggacc tttagacgga atggtgattt agaaataact gcaggtaatt 138900
tcgttcttgg taatgggact gctgtaatta atggtggtct taatgttact aaagcatctg 138960
gtattactac tacaggattg gttgcttccg ctgcatcaag atttgatggt agtgttgcaa 139020
ttaataatac attaactgtt cgagaccctt tgacagctaa tggtggttta acagttaact 139080
cgagaattcg ttcacagggt actaaacctg ccgaccttta ttcgagaaaa cctaatgcag 139140
ataataccgg tttctggtcc gttgacgtta atgattcagc cacatataac cagttcccag 139200
gttattttaa aatggttgaa aaaactaacg aagtaacagg actgccgtat ttggttcgtg 139260
gtgaagaagt taaatcgcct ggtacgttaa ctcagttcgg taacactctg aattcacttt 139320
accaagattg gattacctat ccaaatactg cagacggaag cactactcgt tggactcgta 139380
cttggcagca aaataaaaat gcttggtctg gatttgttca ggtatttgat ggcggtaacc 139440
caccacaacc atctgatata ggtgctttgc cttctgacaa cgcttcaatg agtaacttga 139500
ccattcgtga ttggttaaga attggtaacg tacgtattgt tccggacccg gtaactcgtt 139560
ctgttaaatt cgaatggatt gatacaccat aagaggtaat atggaaagat ttatggctga 139620
atttggacaa gattacgttc aaattcctgt actatctgaa aataatgccg ttagttataa 139680
acttagtata gcaggaagct gtactaagtc cactaaaaag gcttatatca aatttcaaga 139740
tgaggacttc ggtcctcaga atttccaatc tggcctaaat ttggttgaaa tagacccgac 139800
aaataacaca atagtgacta caaaatcata cgcatttacc aaagaccatg atgttatttc 139860
ccaagcgttt ataacttata tttcgtctat acctgctggt agaattgttt gctttatttc 139920
ttccggtaaa ttaaacgcct cacaggtatt aattgattgg tttagggctt ctggctctac 139980
agcatttcca gataaatggc tcattgataa agtggatact tcttattcag ctttttatgt 140040
ttcaggaaga aatgctattg taatggaaca tgtgctttat aacgacggcg ttttggtaga 140100
agacgtttcc accccattag aagtcgttta tgacaacttt aatgatgtag gaggaaccgg 140160
gttccctgtt agagtcattg aagatgaaac cacttattat agtggagcta ctcaagaaat 140220
taaaaggttt cctgccgaat ccaccataac tccttgtgct ggttataata tggttcctgg 140280
agatttcttt tatctcaaat tccaaatgac ctacgaccag gctttaaaag atttagggac 140340
aacccagatg tccatacgat tttttaatgg ccaggaaatg attcaatcca ctgatatcaa 140400
tattcctgta ggagcgggct ctccaccagc aggcgcatgg atgtcttttg agcgcgtaat 140460
agaagttccg ccgaatgcta atggttttac attatattgt agaaaaactg tctcaggcgg 140520
agtaggaggt gttaggaatg ttatgtttgg tgaaatagct agacctgaag atactcctaa 140580
atccgctgaa attggtgtta atggtattcg tatgagctat ggcaccgaaa cccgttcaat 140640
gggtaatgtt attgcacaat tgaatgacaa atcatccggt aacgcaggta aggtgtttgt 140700
tcaagagttt aaagaaaaat attaagggac cgtaaggtcc ctttttgcta taaatacgtt 140760
atctaataaa gaggaataac tatggctgat ttaaaattag gctcaaccgc tggaggttcc 140820
gttatatggc accaaggtaa ctttccgctg acgccagtat caaatgatat tttatataag 140880
acctacaaaa tctatactga atttaataag cctcaagctg cagataatga ctttgtttct 140940
aaagctaatg gtgggaatta tttaggtaca gtaaactttg ataaagacct acaatttaaa 141000
gattctgatg gatactgggt taaattaggt agaaaaacca atacaacccc aatgtcatcc 141060
acatattctt tctcattcag aatgagtaaa ggcatgggtc ttgaaacagc tgatggggtc 141120
ccgtttgtaa ttttcgaccc gactactgtt gtaggtgcaa accgacttac tgtaatgggt 141180
gatatccttg gtcgacagat taaagatgaa tctggaagag tgttttctcc agggaatacc 141240
ccgacaaaag cccaagtcgg attaagtgat gtggataacg caaaacaggt ccaaataaat 141300
aatagtaaca tacaatctat ggctggcgtt ctttcagccc cgaatttcat atctaggaac 141360
ccaggtacat tgaacgaaca cgttcctcgt attgaccagg ttgttcttag aggtacatct 141420
gaagattttg gatattatta agaggcatta tggctacttt aaaatcgata caatttaaaa 141480
gaagtaaaac accaggagcc aagcctactg cagctcagtt agatgaaggc gaactggcta 141540
ttaacttgcg tgaccgcact atttttacta aatcagacca gggacagatt atcgatttgg 141600
gctttgcaaa aggcggacaa gttgatggcg atgttaatat taacgggacc ctgaatttaa 141660
atggtcctga aattgttgcc tccggtggtt atatagaatt taactatcgt acgacaggta 141720
gtggctcttg ggcgggtcag cacaatgcca aagctcctat tttgctgat ttaagtgcgg 141780 ctgcatctac ttcagaatac aacccactga ttaaacaacg ctttaaagat ggaacatttt 141840
cagcaggtac actagtaagc gaaggcagtt ttaaattcca ttatattaat gaagccggtg 141900
attcgaaata ttggaccttt aatcgtaatg gtaattttca agttgatact ggcggcttga 141960
cagttacagg cggtagtatt tccacttcag gaaacgtagc tgcttccggc tttttatcag 142020
caccacaggt taatagtaaa aatattattc ttgattcgaa aaatttcgga cagtatgacg 142080
tccaatcttt agttaactac gtatacccag gcacaggcga aacgaatggt gtaaactatc 142140
ttcgtaaagt tcgcgccaaa tccggcggca ctatgtggca tgagctttgt actgctcaat 142200
taggccaagc agatgaattg tcttggtgga caggtaatac tccatcatct aaacaatttg 142260
gcattcgtaa tgacggacga atggctggcc gtaatagcct tgcattaggt acattcacta 142320
cagatttccc gtctagtgat tatggtaacg tcggtgtaat gggcgataag tatcttgttc 142380
tcggtgacac tgtaactggt ctgaaatata ttaaacaata tgtttatgat ttagttggtg 142440
gaggttattc agttgcttct attactccag atagtttccg tagtactcgt aaaggtttat 142500
ttggtcgttc agaagaccaa ggcgctactt ggattatgcc aggtacgaat gccgcatttt 142560
tatcagccca aactcaggct gacgggaata cagctggcga tggtcagacg catattggtt 142620
ataactccgg tggaaaaatg tcgcactatt tccgcggtaa aggtcaaaca aatattaaca 142680
cccaagaagg catggagctt aacccaggta ttcttaaact ggtaaccggt gcaaataatg 142740
tgcagtttta tgctgatgga actatttctt ctattcaacc tattaaattg gataatgaga 142800
tatttttaac tacctctaat aatactgcag gccttaaatt tggcgcccct agcggagtta 142860
atgaaacaag agctatccag tggaacggtg gtactcgtga aggacagaat aaaaactatg 142920
tgattgttaa agcatggggt aactcattta atgccgccgg tgataaatct cgcgaaacgg 142980
ttttccaagt atcagatggt caaggatatt atttttatgc ccatcgtaaa gctccaaccg 143040
gcgacgaaac tattggacgt attgaagctc agtttgctgg agctcttaat gctaaaagta 143100
ttaatgccat cgaaaatttt aaagttaatg gattaagcac tttagtcggc ggagttacaa 143160
tgagcaatgg acttaattta actggcggtg ctaatatcag cgggccagtt aaaatcggcg 143220
gcgtcaccaa tgcattaaga atttgggact ctcgctatgg cgccattttc cgtcgctcag 143280
aaacatcatt acatattatc ccaactaatg aaaatgaagg ggaaaacggt gcaataagca 143340
accttcgtcc gtttagtatt gagttaggca ccggtacggt tataatgggg gataaatcta 143400
cgggcggacc gcttttcacg gtcgacaacg taagtaaatt cgtccagacg gactgtagat 143460
tccgtgttaa catggattct gatggtattg ttgttaacgc ctcatctcaa gcagcatcta 143520
actttattca aggtcgtaag gctgatgtga ctaaatggta tttgggtatt ggcgatggcg 143580
gcaacgtcgt tcgtatgcac aactacacat attctcacgg tattgcgtta aactctgata 143640
ctgtcgatat tactaagcct cttaaagttg gaaatgccca actaggaact gacggtaata 143700
ttacaggtgg tagtggtaat ttcggtaatt taaatactac catcgagaat atgaaagccg 143760
atattgttac cagttaccca gtcggtgccc ctattccatg gccaagtgat tcagttcctg 143820
atggatttgc tttgatggaa ggtcagacct ttgataccgc agcttatcct aagctcgcta 143880
tagcatatcc taccggtact attccggata tgcgtggaca aactatcaag ggtaaaccta 143940
gtggacgggc cgtgttaagc gcagaagcag atggtgttaa gtctcataac cactccgcat 144000
cggcatcaac tactgctttg acaggcacaa ccaatggtac ggacttgggt acaaaaactg 144060
tcagcactgt tgatataggg cgtaagtata ctaataacgc aggagcgcat actcacacgt 144120
tctcaggaac aactagtacg aacggcgacc ataaccaccc agcttcactt ggtaacaacg 144180
ccaacgttca atcaggtcgt tttgcagcat ctaactcagg tcagtctgct atagcatata 144240
ccaacaacgc tggtaaccac agtcacacgt tctcaggaac tacgtctgca ggcccagagc 144300
acagtcacta cgttgatata ggtactcata accataccgt agcaatgggt tcgcataccc 144360
atacgttctc tattgcggct catggtcata ccatcactgt aaataacact ggtaatacag 144420
aaaacacagt taaaaacatt gcttttaact atattgttcg tttagcttaa ggagagggac 144480
ctcggtccct tttaaatatg aaaatttatc acttttattt tgatactaaa gaattttaca 144540
aagaagaaga ttataaacct attaagggtt taggtctccc ggcccattcc acagctaaaa 144600
aacctttaga acctaaagaa ggatacgcgg tagtttttga cgaaagaatt caagattgga 144660
tttacgaaga agaccaccgc ggtaaagatg tttggactta taataaagaa catcttatta 144720
taaattctat tggaagttta tatggggtca catttgacga gcccggcgaa tttgatatat 144780
ggactgatga cggttggaaa gaagacgagg cttataaacg agtaaccatc cgaaataaga 144840
aaatagcctt gctacataaa gaattccagg tattaagtaa tatggttgaa gcttcagtcg 144900
cagataaaaa ggaaaaattc tatcatcaaa accttaaacg gttctttgct cttttagaaa 144960
agcatgagca tttaggtggt gaattccctg cgtggcctga aaaagaacgg aagccttggt 145020
ataagagatt tttcaaataa tacttctgta ttataaatat ctttaaagga gaaaagtatg 145080
gaaccaaaag taggaatatc attatcagac ctactttttg gacttcttga tagaattttt 145140
aaagatactt cttccgggaa agtagttttt tcccgggtcc tagtcgtgat attattgttc 145200
tttatggccc tggtttggta taaaggcgaa tatattctaa acttttacaa agagacaact 145260
tatgcctctt atactgaaat gattagacaa gaccaggaca atagatttaa aattgcggct 145320
atcgagcagc tccgaatagt gcattcttct tcaggtgcag acttcacagc aatatattct 145380
tttaggccga ccaacatgaa ttattttgtg gatatggtag cttatgaggg taaattaccg 145440
gaaacggtag acgcaaaaaa cacgggaggg tttccaattg acaaaacgtc agtagaatat 145500
atggcgggag ttaacgggaa ctattttgaa tcaagtaccg aaactgtatt ccttcctaca 145560
aagaagaaaa cacaattcac gtatatgttt tcatgcccgt tttttaattt ggataacgtc 145620
tacgccggct cgatatcgtt gtactggtat gatatcaaac cggatttagg atttcctaga 145680
ctttcgtcta tgtgtggtca agccggaagg acattaggtc gaactcgtta gaaattggag 145740
gtatacatca ttaagtaacg gtgtatatct tcatatcctt cattaaattg ctcaataaga 145800
gtgtcacgct catcttcagt taatgactta aacaatttgt tataagacaa accattaagt 145860
tcctttccat gttcattacg aatacctaac tcattcaaaa aggcaataaa ctcatcacga 145920
cgttgcatga tgtcttcaca atccgtttta atcaaaatgg aaacaatagt ggcaatttcg 145980
gaaacgattt caattttagt cataatattc tcttcaattc agtacgacat tatctgatag 146040
ggctatacta acatatcctt agggattgta aacatgttct tcgttctttt taacatattc 146100
ctgatacatc tcttctattg gttcctggaa cttaaaatca gctcccagga attcctcaaa 146160
ggacgcctgt tcacgtgtac gcatacctgt tacggtattc tctaagttat gactcatagc 146220
ctttaccctt atgtttctgc ttacgcttgg actctttaaa atttttcttc ttgtctttat 146280
gaacagaagc cttattgaaa tcgtgcttag ctaccagatt gttcacgtaa tttccttaat 146340
tgatattcaa gagagccgat aatttcttta ttagttgcaa tatacatatc acgtaggaat 146400
ggcttcaacc cttccatatt cccatggatt gtcttggaac taatattctt tatatattca 146460
tggtctaaag catcccaagc cggttggttg acataagttc cccaattatc ttccaccgtg 146520
acattcagtc gtttaacatg attaatatgg gcttcgattg catcaatctg gagttgttta 146580
agattcatta gtaaaggtcc tcagagtaaa gttctttttc actaccacca cgttcaatac 146640
gtacttgatt agcataagta gcaataatca ttgcttcttc gcgagtccaa taattgctgt 146700
attggtcgat aaatccttgg tcatcgccac aaacatggtc tgacacaagt ttatcactta 146760
cttggtcaag cacttctgcc atatctttgg aataatgacg agctcctgga ataactagag 146820
tcccaccgtc cttcagttta aaacggttgg ctgcgcatac aatcctgcgc tgatattttt 146880
cattgttgtt ccaatgtgca atctgccaac agatttcagg gacttcattc aaaacatctt 146940
gttctgtata ttcgtatcca tatgactgta atttggcagc cagactttca ggggtctcac 147000
gtgacagagc tttatctaac agagctaaac gttcttcaaa agttttcatt tgaaccatcc 147060
tttaacacgt tgccagaggc ttttctgttg agctttattg acaccgatcg agcgaataac 147120
aggttgtgat tcttggtatt ctttatagtc agctttataa acttcgtatg cggcatcaac 147180
aaaggaagaa atagcagcca tataattttt acgaatacca actgaggcat tatcattttc 147240
gcgaataatc agatattggc ctgctttaac cttaacgata gaaccgagat aagcgccatg 147300
gtaccagatg tcccaacctt cttgagtagg ttctgcacaa cgacgaagtt cattaacaat 147360
attcagcttg ttcataataa tttcctcagt cagttaaatt gcgttggtta cggctttgat 147420
aacttcagat gatacgtttt ggaagtcgat ataagtattc ttaccaccag tcttaatctt 147480
aacatcaaga ttcaaggaag taaacacttg tttttcttta tcagtcatat tataaccgaa 147540
gatgcgcatc attccatcac ggcgaacttc gatttggcga ataccattgg tacgtttggc 147600
gaatctaact tcaaggttgc tacggttttc agctatttca cggatttcaa tacggtcttc 147660
taataaagct ttaacttcat cagcaaatac caccatttca ggagtaacgc cacgtgaact 147720
acgtgtttta cgtttttcca gcatctctgg ggcattttca gaagcgaaca aatcagcagc 147780
tttttgaact aggtccattg cttcacctgt agccactaaa ccatcgccag atttttcgat 147840
gaatcctttc ttaatcaaca caccgatgtt agagttaact accgcagcac taaattgctc 147900
actcagggct tcacggactt cgcctgaagt gatgaagtta tgcttgatga tatgtactaa 147960
gatcgaagca gtttttcat tcaggacgtc ttcagaagct ttgatgatat aagtaatttt 148020
agacatttta atctccgata accatttatt tgataggtct atagtatcat gtttaaagca 148080
gaagtaaaca ctttttcac taaacccaaa aaaggaaccc gaaggttcct tactttttaa 148140
agtgggctgc tattaaacct atagctaagc ctgttgccag gcctagaata acagcaaaga 148200
tacagagtaa caagaactcg actccaaggc tcatagagcc tccaaatctt taacatactc 148260
agttaccaca tcagtggttt tccagtattg gtgctcttct ttcttagctt tagcttcgag 148320
ggccagtttc ttggcttcat cggaagtgat atggaaaatg ttcatggcca ctagtttatc 148380
agcatattcg ccgtagactt tattaccagc caattcttcg gttaaaacct tacgagtctt 148440
accttggata accactacgc cgtcaataac atctttgatg aatgtggctt tagccaatgc 148500
cagtttaaaa gcttcttcgg tttcgatgat tttaccatca atacgtttct gtacaaaggt 148560
cttacggacc tcaacgaaat cacgaatcag ttcaactgca tcttcgtaaa ccttaagttt 148620
acctttttca ttaatgacgg tcaggttttg tgaacgacgt tcgattaacc caaagtcctt 148680
catgattttt tcatgcttct tattttcttc ggagggcaat tcgtattctt tacgaatctt 148740
aaccttgaag ccaaaaccat tctcgtcaca gtcatcatca tatgtgatat accctttgtc 148800
ttccagaggg tctaatatct tggccacata tgtttcacgg tcatatttgt acgggatttc 148860
cgtgatatgc atttgggttc gagatgtgaa cttataggtt ccgcgaatct cataactacc 148920
tggttcaatc tcaaccactt caccacggaa ttctggataa gccactttag gcttggttac 148980
tcgtttttcc tgaagaactt gtagtacagc tttcttaaca gaatcaaaac tatgaggaag 149040
aatattagtt gcataaccag ttgcaatacc ggaaatacca ttaagaagaa cagtaggaat 149100
aataggcaga taaaaagccg gtggcttatg ttcgacatcc gcatgaaccg gagcatattc 149160
tgtgtcctta taaacttttg caaagttact tccaatacgt gcaaagatat aacgagaggc 149220
cgcagctttt tgaaccaatc gggaaccaaa gttaccttga ccgtccaaca aaggataatt 149280
gttattccat gtgttagcca ttagtgctaa agcttcttgg gccgaattct caccatgatg 149340
ataacccaag tcggcaacac caccggcaat agaagctagt ttatggaatt tgtctttatt 149400
tcctttaccc atttccaaag ctctacaaac accgaaacgt tggactggtt taaagccgtc 149460
aatcatatta ggaatggctc ggttttcaac cgtatacatt gcataggcca gggcttcgtt 149520
gtcaataatg ctttttaaat cacgagttgt taattccata gcaatcctct ttaaattgat 149580
ttatcaatct agtataacta atattatcat atcccatagg aataataact tttttaaagg 149640
ctttatcacc cggtttattt aatttaatcc ataaattgta aagcgtatta taattttccc 149700
aatgtttacc ttttctaaat gctttcttta atgctttaga atgtcgttct ttaactttag 149760
ggtccttaaa agccttttta acagaatcgg ataacttttt aactgattcc gggttttgcc 149820
acgtgtcttt tgctcttaaa gaagcttcta atctttcttc ttcgccccac cattctttta 149880
cagatttcga taatttatct ctttttcttt gagagctcca aacagattta gaattcaacg 149940
atatttttag tctaacttca ggtgaattca tggcctctaa atggttcttt acatattccg 150000
ggttcttaaa aagagcttta gtagcatcag actttttctt tctggtttta tctgtattgg 150060
cttgtctttt tattcctttg gagtgcgatt ctttatttat tgggtctgcc caataaattc 150120 tcatttttc agatagaatt ttagaagcct tttctttagc tatagaatat cctatagaat 150180
tcaaccttat tcctttagga ctgcctgaag tataaaatga ccaatatgct aaataaagac 150240
cattagaatt gggataaatc tttgttagta tccaatgggc tatataatgc tctctagcgc 150300
ttaaaagaac tttattttca ggagtatcgg ggcctcctat gcattccggg attatatgat 150360
gaacttccga ataaaaatcc aatttgcctt ttttgagccc tcttccttta cccctatcaa 150420
ttattgcttt gtacaaatta tgataattca tttataattt taccatacta gtgaatgaat 150480
agccataata acatcggaaa taaaaagcac aacttggata agtccgaaca ttactccata 150540
atacagtgct actaataaag cagcaagggc tactgagtag cccaagattt gtttaatcat 150600
ttttaatcat cttaagtaaa ccgacagaag tagaaagaat ccagccaata aacagaaaac 150660
ttaagaatac cggaccaggg gtccacacac ctaaaaagaa gcaaaccgaa cagacaatag 150720
ccataataag ctcaataaaa actagaataa ccatattttc ctcattagcg tccgaagacg 150780
cctttagttt taagattgtt acgatagaac tgcatcacat gttcgttatg gaaattgctc 150840
attagtatgc ctgcagaatg aatttaaagt tatcagccaa catgcggttc atttcttcca 150900
gtgtctggag gtcggaacta tgattgcgag tgaaagccgt tgcaatttga cccttaccaa 150960
aacctgtagt cagaggtttc attttagaag ccggtacata aagaacttca tacacaacac 151020
cattcactgc catagtgcgg gctgattgag aacgtttctt acgaatgtta gccacgatac 151080
cgtcgagacc ttgagccgaa cgttgattac cgacataaaa acgagccgct acgacacgag 151140
aatcagctcc gcctttaaca aagaagtaga agcctggctg agcagagatt tctttagaag 151200
gtttaccatt ttgatattca ccgttcttaa cataagcaac ggtagtagca ccagcagaca 151260
gaacgttacg gcgagtcata taagtattca tatcaatttc ctcagtagat taatgttttg 151320
ttatccagtc aacgagaacc attataacat gattctcgag gttgtaaact atttttgtag 151380
ctgttctaaa ataaatccgc tggtataaaa ggtagcatta taaaccttgt tcagcgggct 151440
caaagcctgt ccgtaagtat cacgtagttc tttgataaca ttttcataac tcacataata 151500
gccgctatga taatacgggt ccatactcat acggaattta atgaaccgat aaaagcctgt 151560
ttccgggtct tgaacgaaaa cgaaatcagc actcgtcata atttttgaat ctacgccggg 151620
aatcatactt tgattgaatg ccaccgatgc atcctgaagg ctgagttgtt taaagaacat 151680
taccttagca ttaccaaaaa agattttaga catgataatt tccttattca acgtcaacag 151740
aaatagccat cagttcatca acagtaagac actgtacact ggggcctaca caaaaacgct 151800
tagtcgaatc ataaaggtct gtagcattaa caggttgtaa ttcggtccca acttgcaaag 151860
gagaaatgcg aatcagttgt tggccgttat gcaatacaaa gctctcacca actgcaacat 151920
ctttaaaaag tttcataata ttttccttag aagttaaaga atacacgtac atggtcaatc 151980
ataaaaacga ttgggaaaat gctcaacacc attaacaaca caaacatgtt ccaaattgct 152040
ttaagtaagt ttttcataat catctccatt agttgatagg tctataatat catgattaat 152100
ggagatgtat actgatttat gccaatttcc acaacaataa actaaaacat acgcaaatca 152160
ctgggataca ggccatccaa ataaggcacc acattttgct actcaaaaca ccacctcttt 152220
tatctcaatc aatcccctgt acaatgcagt gcggaggtca taaagaatat ctatgccgtc 152280
gacattatct agtttaccgt cgataagttt ttgtaaatct tcctttgatg cgattaaggg 152340
acggagaaat ttacattcag aaagagataa ctctgtagta acatcatcac cttcacctga 152400
cgcgtcatac atagcggcaa caaccatacc tgtaactttg tgtttagcgt aatataattt 152460
gatatccatt ttgttctcct ctcaagttga taggaagata gtaacaccat ccgtggtgta 152520
tgtaaacact tattttaaaa aattataagg cgagatacca gccgttgtaa ttgctcttac 152580
ggactagctt tttgatggct tctctgtcac cagagaactt aggagtgaac aggacgtcgc 152640
ctgcctcatt tactgaagtg tcgaatataa ttatacagtc tgcaacttta tgattcaaga 152700
gcggccccag gttaatccct gttccatacg ggaagtcacc cgagtatcct gtagtacagg 152760
aaatccactt agaatctgat tgatgggtct tgacctctac acgtagtcca caatacatag 152820
gatgggctaa aacgtcccat gcataggtat aagggtcatc atggtcttcc aaaccactat 152880
taacataccc tttcaaccaa tcagcaacca tgtactcggc gtacgttgca atgacacacc 152940
gagtcaatac ttctttctta tcttgggacg ggtcttgact taaggaatac aatacggtat 153000
ccttaatctt aaccttcatt tcgcctgtta aatcagatgt cttcagggta aatgtcggca 153060
tcgctgccaa tcggagtagc cccgggttcg tcttcaccat aaatgcctcg aatatgaagt 153120
tcgccgtaat aaattcggtc gtcgggttct aaagtatcag aatcaattaa aggaaattca 153180
ccttcgacca cctcatcgca ttctaaaaaa gcgtaatgaa catcaccagg gtgtttaaca 153240
agcttagcac aataaacagt acctgcttta tggaacccac gcaaattaga aatcttgata 153300
tcacgttcac cgacattcag ataattaatc attttactca ccgaaataag aaatacgaac 153360
ctctaaacaa tgagcatatg cacccatcgc atccagttgg gcaatcagta acccttgttg 153420
acggatatca agagtttcaa aaacaccgcc tttaataaag gtttctagtg cattaatttt 153480
aagaactaac tggtcgtatt cttcaattaa acgtgcttgg taacctaaca taatttcctc 153540
ttaggaggcc gaagcctccg tttagtttta acgtaaatct gatttaaact gttcggtaac 153600
gtcttccaga acttcataat aacatacgcg cattttagca tcgccataat caacaggaat 153660
actaacaaca tcacgtgggt taactttaca tgaaactaca cggttgtttg aattaccaaa 153720
tgcaccgata tagctacgag agcaaacgtg tagaccgctt gaacaagtta ctgtgtcgtc 153780
attgtttaca cgtgaacgag gcattttaac cggtttgcct ggtgagttat caaacgtacc 153840
agtacggcag tcggtgtaat cggagttaac caccttccac gtaataaagt ggccatcttc 153900
agtaattttg atatcgtttg caaccaggaa gtcgaacaaa cgttgtacag ctttttcgct 153960
tgggttttct aacaggttct caaggaacgg caggtagaat tcgaagtctt cgccattttc 154020
cattgaagca ataatacggc caatcaaccc tgaacgcaat tcaacgcctt ggtaaaccag 154080
acgtccacct tcaatacgaa cgttaccttt gacgaagacc ttaacagctt ctttaatgga 154140
aatcagttta atcgcgtcgt caaaacggga ttctttaaga gcctgtacga tggcatcaaa 154200
atgtttattc ttattagtgg tgttccatac tgtacggcct tcggtgatgg acacgaattt 154260
agaactggca ttccaaataa tttcagggcg agaaccaccg atagtaatat caaccggaac 154320
tacacgaggc tcgttaggaa ccgttacttt gatatttccg gtaataacca cttctgttgg 154380
ggcattaaga ggtacagtag gcgctttttt aagcgattcg gctaattctt tagccacttg 154440
agaacgttta gcttcttcag catttttcag gactttacga atggtatcaa ccgaaacact 154500
gtaccaatcg gctagttctt gctgagtata attaccggat ttatagaggg aaactacttt 154560
ctcttgttca gatttagcca gacacttaat attgtacata atatttcctt agattaagcc 154620
gcttccacgg ctttcatgaa tttaacgatt tgagctacag aagcctcggt aatggatgtt 154680
ccacgacgat acatgtagtc cgaaactaaa tggtaatcag attcaaactg taaagtcatt 154740

```
ttatcattgt tgcttgaagc attattggtt aacgtattaa acgtggtgtt acaaattttc 154800
ttgataacag aaagcttgtc atcagtgata taaccatgga aattcatata acggaatata 154860
tcatagaaat tactcagacg agtatatgct tcagtcaccg gcttatcact aaaatacttg 154920
gtcatgaaac cgagctcagg gaacttggca atgatttcaa ggtaataccg agcacgggta 154980
ttactaccaa ggtagtcatc aacatctacc gcgtctaggg cttcagcata ggcttctaat 155040
gtagcttcca tcaggcattc acactggcct aactttttaa tctttttggc aatctgaggg 155100
cgaatgatat ggaattctgt tacaccaatc aaattagcca tacgacacat ggtagtggta 155160
ttgatgtcaa agataccata agcttcgtcc attcccatga tatcagaacg actgccaaac 155220
agaacataac ctgtaatttc ttctgcttct gcggcggtca aatacatggt ctctgtttgc 155280
caacgtccat ctttaatgaa ccaacgataa gcactcggtg ttttaggacg aggttctgat 155340
gagcgaacag taactggaat ccatggctta acaattttat tcagttcaga gactttataa 155400
aaatgaattg tgtcaccttt aaaaagttct ttaacctttt caagctgctg catttgcagc 155460
aaagaattag ggtcgacaaa aataaggtct gttccgtatt taggaatatt gtgctcttta 155520
acaattttct tggctgaagc actgttgtcc attgccagag cccaaagtcc tcgaactaat 155580
ggaacacggc ccttttcatc atcataaaca acatggattt ctttcttatt aatgcctaat 155640
aaattactaa gtcctgctac tgaagaagta ttaccgcttg acttaattcg tttcaaacgt 155700
gggtctgaaa cgacttcgta aaccacacct aaattaataa ggtcgttttg aagggtataa 155760
cgctggtata atttctcata tgtcaatttt tctgtagtaa acaggctagt tccacctttt 155820
ttagtaagat agtcacgagc gctgtagcca aggttagaaa ggtcacgata aacatggcgt 155880
ggattatcag attcaaccca ttcctgtgta tcgtttttaa agactaccgc atccagtgct 155940
tcgatacggg ttgcaatatt ttccatcgta cgtttatcaa gagacaacac ttcacgagac 156000
ggagcaatat ccagtgaacc catagggaac ttaatataaa ccacatcatg gcgagtacgc 156060
atccatgtgc ctttaatata ggcggaatcc aatggataaa caataccacc gtaaacagca 156120
taaagtcctg aacgttcgaa gctgccataa tttgtagtgg ttacaggatg gtaatcgtca 156180
aattcaggga aataatcaac ttcaacacca tcgacatcac caagaccaac aaatggacgc 156240
atgatataac gaatttcggt ttcaaactta cggaaatctg attcatctac aggaactgtg 156300
atttcaatgc ctgttttatc acctggctgc ataggttcga cgaaagtggg tttaatctgt 156360
gggccatcac cgtccatata agctacataa ccacgaactt caccattatg ccatgacgtg 156420
atattaaacg tttccgtata actaaatgga gattttgaac caagtccaaa gccgccgatg 156480
aaatcattag aagaggtttt agaagaagca aaataagaat tatacagacc tggttcttca 156540
tcattaccac gaatctggaa atcactcatg cctggaccaa aatcacggca tacgaaacgt 156600
gggtccagtt taccaggaac ctgtactttc cagcgttctg tattaccatt cagcatatgg 156660
gcatcaatca tgttagtaat cagttcacgt actacagcac gtactttatt actataaagg 156720
tctgatgaca gaattttaaa gaccttaggc gaggcctgga tagtaaagcc tgtggactta 156780
gcgccattac caatgatttg ttctttttcg gtttcaataa tcatattttt ctcaattcag 156840
gttacgttta aaaatgtctg ccacttcaag gagctcgtcc ttagtagcga tgtcgttgag 156900
tattttatat ctgatttctt taaagcgttc tttaaaatcc tcagctgcat tgatatcaaa 156960
aaatcgctgg attagccgga attctttatg gacggcttta tcgaacaaat caatattcac 157020
tttaaagttt gtcattttta actacctcat gttgaacata ttctctggta gaacctagtt 157080
cagccagaat tcttctcata gaacccattg tacttttgtg ctctctgtgg cgatacatta 157140
```

```
tctctaaaac cttttcctgg acaacaggag agagcgcctg gttatcttta atctttaagg 157200
caatagattt tacagccttt aagtattcga gtcccttacc gcttgtagtc actactcctt 157260
catctttaca gttacgaata gccgtttcca taaaggataa agccaggttg tcagtattca 157320
ctatactgtt atcttgcata atcatattct cacctctaga taatcctatc acagttttgt 157380
tatgttgtaa accccgaaaa gggcccgaag gcccttaatt attcaatttt gtagacttgt 157440
cctcgaactt gataaaattc gccttcccag gtttctacca taatggtcac gtactctgcg 157500
aacaaaggtc tcttctcagc ccagagatat ccaaattcac cggtggctag cgttatccag 157560
tactttctca taaagtctcc taattgtatg gcactcatgt accatacata tttattacga 157620
catccaggcc ttacggagtt gagggtcgtt tcctaggagc atttcgaact gttctttcca 157680
atcttcaggc aattgaacta catcaaattt agggtcttga atcattcgac ggtattcaac 157740
tttctcaaga gaaccgagac ctttgatata acgaatggag tgttttggta gagagtcctt 157800
agctttggta taactaggga catcgtagaa ccattcctgt tctttaccaa cctgagcaat 157860
aatcactgga gttttacaga accgcactcg gccttgttcg aacaattcag gccattgact 157920
aaagaaggct agcaatgatg gataaatcga acccgtacca tccacatcgg catcggtcat 157980
gatggcaata ttacgatagt tagttttctc tgcaggttca ccaataacca gtccagtgat 158040
tgcacagata tcaaatagtt ccttgttctt catgatatct gttgctgtca ttccccaggt 158100
attcataacc ttaccacgta atggataacc accttgaagg tctttattac gaacttcaat 158160
gaaaggaccc atagcggaat caccttcggt taggaacagg gttgtatctg catctttgcc 158220
gtataagtta gctttaatat gcttatggac cttggcttta gaagctttct tagcggcttt 158280
agtttcagct gccttttcag ctgctaattt acgtgctaaa gccgcttcaa cgataggcat 158340
aatcaaccct tcgtctttaa gaatatactg tgagattttc tttgcatcaa tttgaatatg 158400
gttacgaatt tcaccgaatg gtgacgtcaa acgttcttta gtctgggaat caaaacgcat 158460
attactcata tcgcgaatga acatcagcat agttaagcat tctttaactc gtgccttact 158520
tacttcgatg cctttatatt tcttcttgat gcctggcaag agatgttcgc agatatcatc 158580
aaacacacat tcaacatgat gaccaccatt cttagtatga atattgttca cataagttag 158640
gtgacggaat ccatccggag atgtagtaaa tgccattgag acattatcgg tttcttgaat 158700
tactacatct ttaccaaatt gattagcata ctttttaaag ttaccatcta ctttttttacc 158760
attaaaagta aattggatac taggataaat tacagctaga gttttaagac gatctagagt 158820
aatatccaga taaatttgtg atagagagtt ctcttcaaaa tgattaaagt ctggagtgaa 158880
tataaccgaa gtacccttac ctttagattt cttagtagac caacctttgt tttccattcc 158940
attggaacag ttaactgtaa tttcattctc gccatcagag gtgatgcctg tgaacaaaac 159000
agagaagata ttagttaaac tactaccgac accattcatg ccgcctgtct tacgctcagc 159060
gtcatctcca aagttaccgc cagcctttgg aatagtccat gcagctacag gacctggaat 159120
ctgttcacca ttttggtcgg tgaccattgc ttgtggaata ccacgaccat tatcagaaac 159180
cgaaacctgg ttattcttaa tttgaacatc aattttattt gcgaatttaa aattggtacg 159240
aatagcttca tcgacagagt tatcaatgat ttcgtcaatt aatttaacca gtccaggaac 159300
atagtttacc tgtgtaaaat taccaaacag gaatcgaccg tgggcttcat tagcactgga 159360
gccaatatac atcccactac gttttttgat atgttcaatg tcggacagta ctttaatttc 159420
attcttaatc atgttatttc ctcatgtagt aggagaatat tatcccattt cacttaaagc 159480
```

```
ataaaagggc cgaagccctt aatcaaatcg aatggtcgac tttttaaaga ataatccaga 159540
acaaacagtt ccttcaaccc ttttacccgt cggacccaca gcaataaagc ctgtacgttg 159600
gaaatcatct tcagaacagc caaataggtt atatcctgtg atttggattt gttcgtagcc 159660
atttgcatcc aatacacggg tagcattatc agcatcagta caaccgacca acgaaaccgc 159720
cagtaccagc gcggcaatag aactattaat gtatttcata atttctcact tagtcagcag 159780
gtcgtaaaaa ccgccattaa catgtttagg agccgagact aaccgaacag ccagccgatg 159840
gcagtcaggg caaacatcat tatctctttc agagattttc ttgatttttt cgtattcttt 159900
tgcacagtct tcagattggc atttgtaatc ataaagtggc attataagtc tccttccaga 159960
attcagtgcc ttcagcagtg atttcacgga acactgcata gataggggtt ttatcacctt 160020
gattttcgta tacataaacc gatgataaat gagaaaacgt atcagaatgt tccttttgaa 160080
ccacgattaa atctgggttg aacagaacat cttcaaattc ttcacgagtc gagttcatag 160140
taactttagc cattttattt tcctctcatt tgttgatagg gtaatcttat cactacccta 160200
ccatattgta tactgttttt ttaaacttta tgcaaaatga atatcagcat actcaacgat 160260
aaagctctca ggaacaacct taaaggttcc aaggaacacg atgttataga gcttaacgcc 160320
ttcttcaacc cactggtcgg tgatgtaacc ggacatacta gtggtttcat aagtcggacc 160380
gtacttgcac ttgtattcaa acggtttagg tgaaacgaaa aagacacctt tacctaattt 160440
ccatttgaaa tcaacaccaa catgagattg gtcaatagtt tcaacgtctt gagctactac 160500
gccacggata tcattgcttt cacatacata cccatcatgg gattcaactt cttcaactac 160560
aggagcgatg tatccagtga attcagtcga ttccaagaat ttagcacgca cataagcgaa 160620
ttgagtttca gtctggccat ttttaggaat gatacgcact tttacttcag aattttctac 160680
actgacacct tctttaagtt ggatactaac aacttcaact aaacggcctg cagcttttga 160740
acgagacttt ttggatacac gaacgatacc gccgatatcg gaaatagtaa tcataatttt 160800
tctctcttgg ttaaaggttt attctccatg agagccatta taacatggct ctcgataaag 160860
taaactatta attcaataca ttaaccactg cactacgagg tactacacta aaatcaccag 160920
catgtacaac gttcaggagc tcaacaccgt cttcaatcca ttggtctgtt acccaaccac 160980
agataggatt atcaaaagga cgacggatag acacagcagc acacaacagg tcggtagggc 161040
cttgttcttc aacttcttgg aacaggatga actcatcttc ataaaccagg gttttctcta 161100
ttttgttatt atctaaccgg cgaccgtgga tgacgtaaga tttagtaaac cagtcacttt 161160
tggcaaattc ttcaacaata aattcgcctt cgccaaaaac atcagtcaga gttttataac 161220
cagaaatcaa ggccttagtt ttaatttcag gttcaaccag tttgtaggtt ttgccgattt 161280
cgatagtctg agtagtcata ggtgattcct taatttccag tggtttaaca gggcatacat 161340
aagtgcttaa aacatcaaaa tcaatcagtt tagctgccgg attcggggta tatttagggt 161400
tataattaaa tttcatattg ttctcaattc aataaaatct acgagttcgg catgggattt 161460
gcggaacatt acttggcggc caccaatgac aacctcatct tctggtattt cgtaaacagc 161520
aaggtagaat cctttagaag ataattcttc acgctcttca cgagtgaacc agcgcatcat 161580
atcatactca ctggcaaaag caaaatggta gaggttaaca aaccaacctg gaatataatc 161640
gtcagagcct tcataatcag gccgtttcca cttagttcta atggctttat tagaattttc 161700
taccaacaac ttatcttgac ttggtagtgg aatattttta ttgacggtat gatggtgcct 161760
aaacttaggt ctgtcgaaac ctacttccaa taaccatcct tcactccatg agtccattgt 161820
acttctatat ggagtcattt gggtacagag gtctcgtcgt attgttatag catcttcaca 161880
```

```
atctaggata ctgaacgatg actccactcg ataaattttc attttgttct cctcatgttg 161940
atagggtaga taatatcatg tcatgaggag aagtaaacac ttttatcgat tttttatact 162000
taatgggtcg ggattctcag ggacatcttc caggcccaag gcgtatcgtt gggcatattt 162060
aagcatcaag atatccttag cacagtcatg gatggagtca tgagcaacaa agccgttcaa 162120
tgttccgtta ggcagaggac acatgctcaa tccacgagtc aatgaatatg cttcaatagc 162180
cgtacggatg tcacgttggt tccagaattt aaccggttct aatttgctgg tatcgatttc 162240
attctcaggg acaccttcag aacgataagc atcgcgaata aggtcgacta agataggaaa 162300
gtcaaaggac attccacggc accacatctg agatttccat tggtctactt cgtttttacg 162360
gcagtattcc aggaaattac caaggccgat agaagtggtc acatcaattt cggacggcgc 162420
caggttttta cgtgcttcag gcccttgctc tttccaccac tgcaacgtgc ttttagaaaa 162480
cagtcgttta tcacgttgag aagcgaggtc aaatttaata cgaaggcctc gttgagtaag 162540
ctcttcaaac gtttctacaa cctctggatt ggggtcataa gcaattacag cgaggtcgat 162600
aaccgcggca ttttgggttg tggcaaaggt ttcaaagtca ataattatat ctttcattta 162660
acgtacctca taaggtctcg gatttggccg acggtgtagt cttcaatata aaccgaagag 162720
atattgtcgt ccattagacg ctgtattgca ataaaatcgt attcaatctc tttaagagaa 162780
tgcaagacct tatgggcctt gccacggata ttggtatcgt cttggttgac cttaataata 162840
tattcagttt caaatttcaa cttataaaat tggtctttgg ttactttaat catattttcc 162900
tcaaacgtaa taagcgtcag tacgagcacg agtaatacta acataagcca gctgtgaagc 162960
taaactcaca tcagccatat gcatacacgg cgtatagatg aaactgttct ggactgtgag 163020
gccctgggat ttatgaacgg tgctcaccgg aagagctcga accttagtaa acattctctt 163080
agctttccaa aaatcggccc acttaggttt cttaccacta ccacgcatgg ctttgtattc 163140
agtagcaacc ttagccaaga aataatggaa cttctcgact gaagcctcat ctataacctt 163200
taagtgctct acgtaatact catcatcttc atcgatagat tctacttgca ggtcccagta 163260
attaatcatt tgacgggtgc ctacatcctt agcagacaag aacaatgagg tgtggttcac 163320
atccagaata cgaaccattt gaccgttatt aaaaatggtt tcagagaatt tcttaccgtc 163380
gtattcaagt tccttcataa aaggctcttg catcaccagg atttcaccct tgatataagg 163440
tgcgtcggtt tcataaagct tttacgaat aatgctattc agcttttcaa ccgatttatt 163500
tgtataagca aacatcctat tctcaaacag tgcatcagca tcctttacaa tggaaaaata 163560
attcatcata aaatctttta atgctgtttg agatttaaaa ccatggacac catgtccttc 163620
gaatacacaa tctctaaacc acccaccatt acggatttca gtagcaacct caatgatagg 163680
ggcattacta cgcattactt cggtcaaatg caattgcttg atttttggat gagtaaagaa 163740
cggagacaac tgcggactac catcacttcc aggttccact ggctgtagct gagctcggtc 163800
gccaatccct aatacagtac accatggagg cacggaagat tcgataatct taaacagctt 163860
accatcaatc atcgagcctt catcaacaac taacacatta catttgctca agtcaggagc 163920
ttcgcgttgt tcaaagatat cctggtcttc gtatgtagta gggttaatct ttagaattct 163980
gtggattgtt gatgcttctt gacctgcgag tttcgacaac accttttttgg ccgcatgggt 164040
aggtgcagtc aaaataactc cgagttcacc attcttgact agatggtcaa gaataaattt 164100
ggtaagggtt gttttacctg taccagcagg gccattcaat gtaatccatt cgcccttacg 164160
tcgtttaata gcttcaatga tttctttaaa agccgtcctc tggccgatgt tcaagtcttc 164220
```

aaatgtaatc atgccaattt tactcgctta acatataaag tgtctaaaac taatttaagt 164280
tctcgggctc gttcttcggt aggatacacg gttttagttt cccacttatc aaaccaccat 164340
tttctaggtg tgcacaccgt ttcaaggcgt ccaagccgaa gatatctttt tgtcgccatt 164400
tcataaacgg atagagcggt atcggctcca atctttgtcg aatacaaagt cacttcacca 164460
gcctcttcta atggaatttc gtacccgtct ttgtccttgt gaactaatac gtatgcatag 164520
tacatcacgt taacctctaa tcagtgaaaa aattgaagca ttcagcggaa gacctttttt 164580
caacttcatt ttgtcaataa aagaaaggtg ttctaaacgc tccagacctt ggataatttt 164640
atcatacata tcgtaacgcg tttctgcttc agacaattta aacttgacgc gccaatcagg 164700
cccaccaatt aaagatttaa gaccctttc catagtaccg attgaagcgt tagaaccatg 164760
gatacgagcc ttaaccgcga tgacagaagg ggtcttatca gtagctcctg atttaataag 164820
gtccttaaga cgtttttcac gctttttaag gcctctttga gtatctttaa tatttttaac 164880
tattttacga attttataat aattatcggg ggttacttta aaactattag gcattttaga 164940
actacctgaa atacggaccg ctaaacgggt ttgtgcacgt ttcaattcat ctagagacaa 165000
atcggcacgt aagctattgt acttgacttt aactgggatt acattaccct caatatagcc 165060
gatatcatta ttaaaacgtt caaatgaaat cttatcacta actgaattct catcaaagct 165120
ctcgcctgaa taagcacaca ctttttgttc gagaagtcta cgaatgtact tactagacag 165180
gttaaagtcc ttaccacgtt tcttggcaga ggctttagtg tgttcgcgac gtttgtaaac 165240
ctttaactca aattcagtag tcatgatatt tctcatctta cggacgattg gttgataggt 165300
ctatagtatc atgttgcccg ataaagtaaa caactttttt gctttaaatt ttcgacggta 165360
taatgaatca aggactttgt ctttcaatta aaccgggagg ttcagtaaga aagaacggaa 165420
agattccaaa tggtgtaatt attccattta ggatttctct caatagagtc tacgcgcagc 165480
gtagttcccg cagggaacat catctcatct tcatcattga ttaattgtaa gtttgctaca 165540
cgggtagatt caggaaatgc gcctgggaac tcttcagggg gcgcagcaca taacatttta 165600
aagatttctt cctgataatt gtacacaaat ggtgcatcat taatacaaaa gatattaaat 165660
gtgccgtaga agttataaga cgcgaaattc cttgccacgt tgaagtcttt agagaagctc 165720
atcacgcggt cgaattcaat taccgcacct acacacattg tggactctag atacttcata 165780
gtctttttag atatgccacg atagagctta tcaggcacta cagaagtcag attcttacgg 165840
ataattttat tcagagtttc ctggatagta tctggtttat tttccataca ctgccagagc 165900
gtgctctgtt ctaaatcaga atacacctca tcaatttcta tctgagtatt ctcacggaaa 165960
tcatcgcatt tagcgttgtt gataaattct gctaatttat ggcttgggta taacatatta 166020
ttctcctcag ttgatataaa gatagtacca caagcctcct tgcctgtaaa ctaaaaatcc 166080
aacattttta aatgaattgt tttatactcg atttcgtacg ggtctctttt gacggtttcg 166140
attgcaacaa tctcaaatcg cgattggctg gagaccatga actcacattc ggtttcgacc 166200
atatcataga ggtcaatacg ggtttcatca atttcaaggt cgtctacatt acctgcaaga 166260
acaaggtcaa tagcatggtt gtagtagtca aaaatgaatg gtgcattcct gagacttaaa 166320
atggttttgg ttccatattc ccatgcccct gcaaactgac gagcctgaga gtattgtgta 166380
ctaaaagaag taacgcgacc aggagaccat tgacaaccta ctgaaaggag ctctaattgc 166440
tcaagttctc tgggggtaat cccacgatac aactctactg gaaccgctga agtaacatgc 166500
ttgcgaacca gtttgtcgag gtcgtaatgg aagttagggt cctttttagc atccagacat 166560
ttctctaaca aggcttgttc agattttgaa aatttggaat tgattcggtc ttgataaaga 166620

```
catttttgtt cgatgttcat atgacctcca gtgatttaga ggtcattata acatgaaggg 166680
aggaggtgta aactacttaa acacaccaag tgggacgcca aacactgcaa tgtcagcagc 166740
catgcctaat gaggattggg tatatgaagt ataggagctt tttgattcat acgagctttt 166800
tgtttctggc ttctcggctt caatcttaag agctttcgcc tgaatatttt tttgctcggt 166860
ttccttacga gcctgtttac ggtcgatatc caacgccgat gtaggtatat tagtcagcca 166920
attcattatt ttacccaagg agcccatggt ggagggtcta agtaataaga agcaaggtca 166980
ctaaggacct ctttaggcaa cttaaaaccg tgcttctgta taatcatatc aagttcgttg 167040
acaaggtcaa caggcggctc ctgggttgtt tcaggctcag ggtccggaat gacaaacata 167100
tcaaataagt ccattagtag ccacctatag gaccgtactc gtacatacga gctcgcacct 167160
tagcatcacg aatagcgtct tcagtcatgg taaagcgcaa tccaatatca aagtgcttcc 167220
aaatctgacg ttcaacttca ataaggtctt cggtagcgga aataagataa gtacgacctt 167280
taagacgttc gttggacatt ctatcggtat ctttatagaa aatgtccatt gttccttcgc 167340
catacgggtc cggatggcga taacccttga tatgcaatgc ttcagccagg ctaaaaggac 167400
aatcttcagc aacatcaaca tttttgttat ggtaagcctt catcataata ttttctggca 167460
gcttaatatc ttttaatcgt gtttctaact gggttataga attcgtacca ttatcgacaa 167520
ggataagaca cgctgtagca tcataaggtc gcgtttgtcc ggcagaatca cgaacaaaga 167580
attctagttc ataaactttc attatgtttt cctcttctta gtttacctac taaaggacca 167640
tccggaattt tattttcttg gatgtatttc tcgttttctt ccatcatttt actaccaatt 167700
ttaagaagca aatccagtgc ctctttagcg tgtttttcag cctcttcagt agtcatgatt 167760
tatccccata gatgtcacgc ataatcctaa gggcctcgcg ttctaatttc ttttcgcgtt 167820
cttcacggat acctttaaga atccattctt cggagtcacg tttcatttct gcattggctt 167880
ggtctaacca cccgtcatca agataatcac taggacggtc cagccaatct ttaagccatg 167940
ataaaggttt cattaatcac acgagctaga cgacgagtca cagcttcctg agtcataaga 168000
cgaataagaa gaatcaccag tccaagaact gacagcagcc gcaaccataa taggagtggt 168060
atcaatatgg cttgtgcgac gagcttctaa atgttctttt aactttttag atttcaaagg 168120
aagagcgccc gggcctacat taccagcttt ttcaggttga cgaataactt cttccatcat 168180
accatcgcct acataaacat attcccttaa cttaacgtct gatggactaa taggaaccgg 168240
cccttcgcca ggggtaatct tgaaaaaatt cttaagccaa caaatcataa gaaacctcgt 168300
ttaaattcaa ccttatcaat atcatcagtc tcgtgacgga tttcggcatt aaattcgata 168360
gaaccgtctt catgcatcat aaatgaatgg acaataactt cggtatacca aggagtataa 168420
aagtactttt tcaatacatg attagcgata atttcatcca aagttttatt tggtttaatc 168480
caacgattta acatagtgtt ctcctctata agataagacc atcttaacac aaccttccta 168540
aaaagtaaac ccttaagacc aaaaaaagga acccgaaggt tccttataat taaactactg 168600
gggtcggcgt gaacattgct gcgttcttag ttcgccaatc ggctgcatca gtcactacag 168660
tagtataggc tgcaacggcc gaagggaaag tctgataatg agagtctgca atacggtgct 168720
cgtttgaata aatctcaaac gggaccgaaa cctcagtacc tttaacttct ttaccttcac 168780
cagctggatg cgtaaaagtt ttgatattaa cgaaaccacc cataattaac tcctttgttg 168840
tttaattaca ggtgtattta ttacgcatat ttcttatcaa tataaaagtg tccaccgcct 168900
ttaacaaaga cccagaatag atttctatcg tctgtatccc gacaataaaa atcatctaac 168960
```

```
tggaaatagt tttcttcagg gaattcaaga tgccggccga gttctattgc atcagaacca 169020
aacgctttag tagcgggacg accatcatcg tcccatttct tgaaattgaa tttcattaat 169080
aaccacggtc ctgacgagca aagttctcag cgtttttcag gtaatacaat ttaaagattt 169140
cttcagcagt cagaccgaga ccttggaaca tgttcagaac gaaatggaga atatcaatca 169200
tttcgaattt aatttcgagc tggtcttcag gagacaaatc gttaatcagg gtttcacgac 169260
gttcagcatg ttgagctttc caaggcttcc atactgcaga tgcatctttt tcgccattgc 169320
tcatgccacc aagagaagtc agaagttcac ggaattcatc atcaatataa tctttctgat 169380
tacgcaacca atcaacaact tcacctgcag tggccaaatc atcaggatga cggttatatt 169440
caggtttatc tttagccaaa cgggcctgta atgatttctg catatcaagc ataacctgca 169500
gagggtcttt atcttcgtga atcagagcat taaaataagc ttcctcagct ttatcaacac 169560
cagcaatcaa accactacat tcattaaaat gagccattat attttccttt ttcaattcat 169620
taataagtta gataattata acattaaaat ttataagcaa ttaggaagac cacccggtga 169680
atttgcgttg tcctgaatcc cagtgaacac ccacgtcagg agaataccta taattaaaat 169740
caccatagga ttctgaaatt tctaaaatat atcttacaaa atattcacaa agctcattag 169800
accatgaatc agaatacacc acgaagtgga aagatgattg gtcctcatca tcgacatcaa 169860
tccacacacg ttttaattta ccttccggcg aatcataaac acctgaaata tattcacctt 169920
taaccgaaag gctcccttct tcaaaagcgg tattcaaaac aagccctaat tctccagggc 169980
tagattcttc tacccaatca tcatgggtat tcaataaaat cttaatcata atatttcctt 170040
aaaaatcaaa tatgtctaat aacgaattgg tggtattaat atgaaccacc ggagctacat 170100
aatcatccat ccattctgga tatttacgcc cttcagatcg gtcattaggg tctaatgtat 170160
ttgcatatgc aaagttatat gaaattatat ctcgatgttc tttagtatca ccaacaatat 170220
ttaagatacg ttggcataaa aaatcatagt tatctttcat atactcaata caatatatat 170280
cttttaaagc ttgggttggt gatactccaa tttccaattt cttacggata atggcttcaa 170340
caagattacc atctcctgct gaaggttcaa agaatgtatt acccgcctta aaagattctt 170400
caccgcaaag ctttaaaaga atttttgtac agtaatcatt agtgaatacc tcatcagtag 170460
atttctggcg ttctcttgtt atttcaccgt tttttcttga ttcatcaatt gctaatttca 170520
tcaaggctca ccccattcac aacattttct gcatactgcc attctaaatc ggtaatgttg 170580
aagcgttctt gaatcatttc acgagtccat ttcttagtaa aatcgaccac aggagcattt 170640
tcaaccattt ttttgcctgc agtaccacca ccaagtccgg cataataagt gcatgctact 170700
ttaataggag gcatattata gaatgctata gcattttcag cttcttcaac agtatcaaac 170760
gaggcccaac attttttgta attacctgaa ttatccccac cgtgtggatg tgaattctcg 170820
attttggttg ctccgttcac aagaccgtta tagaaatcat tacccattat aattttagaa 170880
cctgctaaat gtactgataa tttacggttg aagtttacat aaaccggttt ttcaataccg 170940
ttataaccat ttaatttctc ttcagtgcga gttttatctg caatagattt tgcactaata 171000
ttgttaagaa ttaatgaaac aaactcatta ttcatatact cgtatttggc tttagagcac 171060
ccgttaacca aggtataact aggggattca tctttagtaa atttagccaa agccagatga 171120
gttcctacgt tagccgagaa atatttgtta tcacggttat cgtcaataat tgctattttc 171180
aaacgttttt tagcttcagg ccggtgagca ttgacaccca ttgtgtggag atatgaagcc 171240
ggggttatgg caataacgtt atcagcacaa gctaaggctt tatcaataaa tgctgtatca 171300
tattggaaag gcgggttcat aataattgta ttgaatttca ttttcttagg ggccttaatg 171360
```

```
aattcaaatc cagagaaaca tccgaaagta tcaaatacat aacgggcctt atctgaatca 171420

gttgaaatga ataagatatc ggaagtatca taaccgataa gagataataa tgaaactact 171480

tcaagggatt ctataacac                                              171499
```

BACTERIOPHAGE AND COMPOSITION COMPRISING SAME

TECHNICAL FIELD

The present invention relates to a novel bacteriophage having a specific ability to kill enterotoxigenic *Escherichia coli* (ETEC), a composition including the same, and a method for preventing or treating infectious diseases of animals using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *Escherichia coli* are non-pathogenic and can cause opportunistic infection, but some highly pathogenic strains cause various intestinal diseases and sepsis in animals including humans.

*Escherichia coli* can be classified into enterotoxigenic *Escherichia coli* (ETEC), enteropathogenic *Escherichia coli* (EPEC), enterohemorrhagic *Escherichia coli* (EHEC), enteroaggregative *Escherichia coli* (EAEC), enteroinvasive *Escherichia coli* (EIEC), necrotoxigenic *Escherichia coli* (NTEC), and the like, and, particularly, enterotoxigenic *Escherichia coli* is known to cause infectious disease in pigs.

Currently, with the trend toward large-scale group housing in pig farming, porcine colibacillosis has emerged as the most frequent and bothering disease in pig farms. Recently, outbreaks of porcine colibacillosis, which stunts piglet growth due to diarrhea and mortality, have been increasing in Korea, causing enormous economic loss to pig farmers.

For prevention and treatment of porcine colibacillosis, although various antibiotics have been applied to pigs in the related art, abuse or misuse of antibiotics can induce antibiotic resistance in pigs or can cause the antibiotics to remain in the pigs' body, leading to global restrictions on administration of antibiotics.

A bacteriophage refers to a bacterium specific virus that prevents and inhibits growth of a bacterium infected with a specific bacteriophage. As bacteriophages have stronger host specificity than antibiotics, and recent emergence of bacteria resistant to antibiotics is a growing problem, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the aviculture industry including poultry farming, due to enterotoxigenic *Escherichia coli* are still insufficient, and therefore there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases caused by *Escherichia coli*, the present inventors isolated a novel bacteriophage ΦCJ28 (KCCM11466P) having a specific ability to kill enterotoxigenic *Escherichia coli* from natural sources.

In addition, the present inventors identified morphological, biochemical, and genetic properties of the novel bacteriophage, confirmed that the bacteriophage has excellent acid resistance and heat resistance, and developed antibiotics, disinfectants, additives for feeds, and other compositions using the bacteriophage, a composition for preventing or treating infectious diseases caused by *Escherichia coli*, and a method for preventing or treating diseases using the same.

It is an object of the present invention to provide a novel bacteriophage ΦCJ28 (KCCM11466P) having a specific ability to kill enterotoxigenic *Escherichia coli*.

It is another object of the present invention to provide a composition for preventing and/or treating infectious diseases caused by enterotoxigenic *Escherichia coli*, including the bacteriophage ΦCJ28 (KCCM11466P) as an active ingredient.

It is a further object of the present invention to provide antibiotics, additives for feeds, additives for drinking water, feed, drinking water, disinfectants or detergents, including the bacteriophage ΦCJ28 (KCCM11466P) as an active ingredient.

It is yet another object of the present invention to provide a method for preventing and/or treating infectious diseases caused by enterotoxigenic *Escherichia coli* in non-human animals using the bacteriophage ΦCJ28 (KCCM11466P) or the composition including the bacteriophage ΦCJ28 (KCCM11466P) as an active ingredient.

Technical Solution

One aspect of the present invention provides a novel bacteriophage ΦCJ28 (KCCM11466P) having a specific ability to kill enterotoxigenic *Escherichia coli*.

Another aspect of the present invention provides a composition for preventing and/or treating infectious diseases caused by enterotoxigenic *Escherichia coli*, including the bacteriophage ΦCJ28 (KCCM11466P) as an active ingredient.

A further aspect of the present invention provides antibiotics, additives for feeds, additives for drinking water, feed, drinking water, disinfectants or detergents, including the bacteriophage ΦCJ28 (KCCM11466P) as an active ingredient.

Yet another aspect of the present invention provides a method for preventing and/or treating infectious diseases caused by enterotoxigenic *Escherichia coli*, including: administrating the bacteriophage ΦCJ28 (KCCM11466P) or the composition including the bacteriophage ΦCJ28 (KCCM11466P) as an active ingredient to a non-human animal.

Advantageous Effects

The bacteriophage ΦCJ28 (KCCM11466P) according to the present invention has an effect of having a specific ability to kill enterotoxigenic *Escherichia coli*.

Further, the bacteriophage ΦCJ28 (KCCM11466P) according to the present invention has excellent acid resistance and heat resistance, and thus can be employed not only as an agent for preventing or treating infectious diseases caused by enterotoxigenic *Escherichia coli* at various ranges of temperature and pH, but also as antibiotics, additives for feeds, additives for drinking water, feed, drinking water, disinfectants, detergents, and the like, including the bacteriophage ΦCJ28 (KCCM11466P) as an active ingredient.

Further, the present invention provides the bacteriophage ΦCJ28 (KCCM11466P) or antibiotics including the same as an active ingredient, and the antibiotics have effects in that the antibiotics have specificity for enterotoxigenic *Escherichia coli* as compared to prior antibiotics and thus selectively kill specific pathogenic bacteria; and that the antibiotics do not induce antibiotic resistance, resulting in extension of lifetime of products as compared to prior antibiotics.

Further, the present invention has effects of preventing or treating infectious diseases caused by enterotoxigenic *Escherichia coli* by administrating the bacteriophage ΦCJ28 (KCCM11466P) or the composition including the bacteriophage ΦCJ28 (KCCM11466P) as an active ingredient to a non-human animal.

DESCRIPTION OF DRAWINGS

FIG. 1 is an electron microscope image of a novel bacteriophage ΦCJ28 (KCCM11466P) (hereinafter referred to as 'ΦCJ28').

FIG. 2 shows results of pulsed field gel electrophoresis (PFGE) of a novel bacteriophage ΦCJ28.

FIG. 3 shows results of sodium dodecyl sulfate polyacrylamide gel electrophoresis (SDS-PAGE) of a novel bacteriophage ΦCJ28.

FIG. 4 is a graph depicting results of acid resistance experiment of a novel bacteriophage ΦCJ28.

FIG. 5 is a graph depicting results of heat resistance experiment of a novel bacteriophage ΦCJ28 at 60° C.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ28 (KCCM11466P) (hereinafter referred to as 'ΦCJ28') having a specific ability to kill enterotoxigenic *Escherichia coli* (ETEC).

Enterotoxigenic *Escherichia coli* is a Gram-negative *bacillus* and an aerobic or facultative anaerobic bacterium which decomposes lactose and fructose to generate acids and gases. Enterotoxigenic *Escherichia coli* grows well on common media and is capable of growing at a temperature of about 7° C. to about 48° C. with ideal growth temperature ranging from about 35° C. to about 37° C. Further, enterotoxigenic *Escherichia coli* can grow at pH ranging from pH 4.5 to pH 9.

Since enterotoxigenic *Escherichia coli* produces enterotoxins similar to those produced from *Vibrio cholera*, a patient infected with enterotoxigenic *Escherichia coli* exhibits symptoms similar to a patient infected with *Vibrio cholera*. The produced enterotoxins can be broadly classified into heat-labile enterotoxin (LT) and heat-stable enterotoxin (ST). The heat-labile enterotoxin loses its activity when heated at about 60° C. for about 10 minutes, whereas the heat-stable enterotoxin does not lose its activity when heated at about 100° C. for about 30 minutes.

Enterotoxigenic *Escherichia coli* proliferates in an upper portion of the small intestine, and when the concentration of enterotoxigenic *Escherichia coli* approaches about $10^7$ colony forming units (cfu) to about $10^8$ cfu per unit volume (1 ml) of intestinal juices, enterotoxigenic *Escherichia coli* can cause infectious diseases including colibacillosis caused by *Escherichia coli.*

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ28 according to the embodiment of the present invention is a bacteriophage that has species specificity of selectively infecting enterotoxigenic pathogenic *Escherichia coli* and morphologically belongs to Myoviridae having an icosahedral capsid structure with a contractile tail (see FIG. 1). Homology between a nucleotide sequence of the bacteriophage ΦCJ28 and decoded nucleotide sequences of other bacteriophages is compared and results are shown in Table 1. The bacteriophage ΦCJ28 shows stable acid resistance at pH 3.0 to pH 5.0 without losing activity (FIG. 4), and in terms of heat resistance, the bacteriophage ΦCJ28 shows activity decline of about 1 log or less when exposed to 60° C. for 30 minutes, and activity decline of about 3 log or more when exposed for 60 minutes or more at the same temperature (FIG. 5). DNA nucleotide sequence of the bacteriophage ΦCJ28 is set forth in SEQ ID NO: 1 of Sequence List.

The bacteriophage ΦCJ28 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11466P.

Another embodiment of the present invention provides a composition for preventing or treating infectious diseases caused by enterotoxigenic *Escherichia coli*, including the bacteriophage ΦCJ28 as an active ingredient.

Since the bacteriophage ΦCJ28 exhibits antibacterial activity capable of specifically killing enterotoxigenic *Escherichia coli*, the bacteriophage ΦCJ28 can be utilized in prevention or treatment of diseases caused by infection with enterotoxigenic *Escherichia coli*. Examples of infectious diseases caused by enterotoxigenic *Escherichia coli* to be prevented or treated using the bacteriophage ΦCJ28 include colibacillosis, specifically porcine colibacillosis, without being limited thereto.

Herein, the term "colibacillosis" refers to a disease occurring due to infection with a pathogenic *Escherichia coli* in animals, and symptoms thereof include sepsis, diarrhea (infant diarrhea and post weaning diarrhea), toxemia (edema and cerebrospinal angiopathy), and the like. Thereamong, sepsis is an acute systemic infection with high mortality which occurs mainly in infancy within two to three days after birth. Diarrhea is a gastrointestinal infection symptom frequently occurring during suckling within one week old to two weeks old and directly after weaning, which is a cause of mortality or stunted development. Toxemia mainly occurs after weaning in piglets at 8 week old to 12 week old and can frequently cause sudden death after exhibiting edema and neurological symptoms.

Herein, the term "preventing" or "prevention" refers to all actions to inhibit the diseases or delay occurrence of the diseases by administering the bacteriophage ΦCJ28 and/or the composition including the bacteriophage ΦCJ28 as an active ingredient to an animal.

Herein, the term "treating" or "treatment" refers to all actions to improve or ameliorate symptoms of infectious diseases by administering the bacteriophage ΦCJ28 and/or the composition including the bacteriophage ΦCJ28 as an active ingredient to an animal.

The composition for preventing or treating infectious diseases caused by enterotoxigenic *Escherichia coli* according to this embodiment may include the bacteriophage ΦCJ28 in amounts of $5\times10^2$ pfu/ml to $5\times10^{12}$ pfu/ml, specifically, $1\times10^6$ pfu/ml to $1\times10^{10}$ pfu/ml.

The composition for preventing or treating infectious diseases caused by enterotoxigenic *Escherichia coli* according to this embodiment may further include pharmaceutically acceptable carriers, and may be formulated with the carriers to provide foods, medicines, additives for feeds or additives for drinking water, and the like. Herein, the term "pharmaceutically acceptable carriers" refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer's solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, and granules.

Methods for administering the composition for preventing or treating infectious diseases caused by enterotoxigenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, and elixirs.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by enterotoxigenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ28 as an active ingredient.

Herein, the term "antibiotics" refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ28 as an active ingredient have effects in that the antibiotics have specificity for enterotoxigenic *Escherichia coli* as compared to typical antibiotics and thus kill specific pathogenic bacteria, but not beneficial bacteria; and in that the antibiotics do not induce antibiotic resistance, causing extension of lifetime of products as compared to typical antibiotics.

Yet another embodiment of the present invention provides an additive for feeds or drinking water, which includes the bacteriophage ΦCJ28 as an active ingredient.

The additives for feeds or the additives for drinking water may be used by separately preparing additives for feeds or additives for drinking water using the bacteriophage ΦCJ28 or the composition including the same and mixing feed or drinking water with the additives, or directly adding the bacteriophage ΦCJ28 or the composition including the same in a process of preparing feed or drinking water.

The bacteriophage ΦCJ28 or the composition including the bacteriophage ΦCJ28 as an active ingredient used in the form of additives for feeds or additives for drinking water according to this embodiment may be a liquid form or a dried form, for example, a dried powder form.

For example, the bacteriophage ΦCJ28 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as

*Bacillus subtilis* capable of producing proteases, lipases and/or glycosyltransferases; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feed; and yeasts such as *Saccharomyces cerevisiae* and the like. These microorganisms may be used alone or in combination thereof.

The additives for feeds or additives for drinking water according to this embodiment including the bacteriophage ΦCJ28 as an active ingredient may further include other additives as needed. Examples of usable additives may include binders, emulsifiers, and preservatives added for prevention of quality deterioration of feed or drinking water; amino acid, vitamin, enzyme, probiotics, flavoring agents, non-protein nitrogen compounds, silicate, buffering agents, coloring agents, extracting agents or oligosaccharides that are added in order to increase utility of feed or drinking water; and other supplements to feed, and the like. These additives may be used alone or in combination thereof.

The additives for feeds according to the present invention may be present in amounts of 0.05 parts by weight to 10 parts by weight, specifically 0.1 parts by weight to 2 parts by weight, based on 100 parts by weight of feed. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ28 against enterotoxigenic *Escherichia coli* to be sufficiently displayed.

Yet another embodiment of the present invention provides feeds or drinking water prepared by adding the additives for feeds or the additives for drinking water including the bacteriophage ΦCJ28 as an active ingredient to feeds or drinking water, or directly adding the bacteriophage ΦCJ28 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ28 as an active ingredient. Dosage forms of the disinfectants or detergents are not particularly limited, and any dosage forms commonly used in the related art may be used.

In order to remove enterotoxigenic *Escherichia coli*, the disinfectants may be sprayed to habitats of animals, slaughterhouses, dead regions, kitchens, and cooking equipment, without being limited thereto.

The detergents may be used to wash a surface of the dermis or body parts of animals that are exposed to or can be exposed to enterotoxigenic *Escherichia coli*, without being limited thereto.

Yet another embodiment of the present invention provides a method for preventing and/or treating infectious diseases caused by enterotoxigenic *Escherichia coli* using the bacteriophage ΦCJ28 or the composition including the bacteriophage ΦCJ28 as an active ingredient.

Specifically, the prevention method or treatment method of this embodiment includes administering a pharmaceutically effective amount of the bacteriophage ΦCJ28 or the composition including the bacteriophage ΦCJ28 as an active ingredient to a non-human subject that is exposed to or can be exposed to enterotoxigenic *Escherichia coli*. Suitable total amounts of the bacteriophage ΦCJ28 or the composition including the same per day may be determined by a physician within proper medicinal judgment, as apparent to those skilled in the art.

A concrete pharmaceutically effective amount of the bacteriophage ΦCJ28 or the composition including the bacteriophage ΦCJ28 as an active ingredient may be determined by taking into account the sorts and degree of reaction to achieve, age, body weight, general health condition, sex or diet of corresponding individuals, administration time and administration routes of bacteriophage ΦCJ28 or a composition including the same, and secretion rate of the composition, treatment period, and the like, and may differ depending upon various factors and similar factors well known in the field of medicine including ingredients of medicines that are used simultaneously or at different times.

The bacteriophage ΦCJ28 or the composition including the bacteriophage ΦCJ28 as an active ingredient may be administered in the form of a pharmaceutical preparation to an animal by intranasal spraying, or directly added to feeds or drinking water for animals so as to be digested, and may be mixed in the form of additives for feeds or additives for drinking water with feeds or drinking water and then administered to an animal.

Routes and methods for administration of the bacteriophage ΦCJ28 or the composition including the bacteriophage ΦCJ28 as an active ingredient are not particularly limited, and the administration may be realized by any routes and methods so long as the administration allows the bacteriophage ΦCJ28 or the composition including the same to reach desired tissues. Namely, the bacteriophage ΦCJ28 or the composition including the bacteriophage ΦCJ28 as an active ingredient may be administered by various oral or parenteral routes, and examples of administration may include oral, rectal, topical, intravenous, intraperitoneal, intramuscular, intra-arterial, trans-dermal, intranasal, and inhalation, without being limited thereto.

Hereinafter, the present invention will be described in more detail with reference to a preferred example. It should be understood that these examples are not to be construed in any way as limiting the present invention.

Example 1

Isolation of Bacteriophage that Infects Enterotoxigenic *Escherichia coli*

Example 1-1

Bacteriophage Screening and Single Bacteriophage Isolation 50 ml of a specimen obtained from pig feces collected around Samwhawonjong farm in Gwangcheon, Hongsung-gun, Chungcheong Province and environmental samples was centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}$=2) of enterotoxigenic *Escherichia coli* (2618) separated by veterinary infectious disease laboratory of the Department of Veterinary Medicine, Seoul National University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 μm filter. Subsequently, a mixed solution consisting of 3 ml of 0.7% (w/v) agar and 150 μl of a shaking culture solution ($OD_{600}$=2) of enterotoxigenic *Escherichia coli* (2618) was poured and solidified on an LB medium plate, to which 10 μl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 μl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution. Subsequently, 100 μl of the bacteriophage solution was mixed with 5 ml of 0.7% (w/v) agar and 150 μl of a shaking culture solution ($OD_{600}$=2) of enterotoxigenic *Escherichia coli* (2618), which was used to perform a soft agar overlay method using an LB medium plate having a diameter of 150 mm wherein cultivation was performed until the bacteriophage was completely lysed. After completion of cultivation, 5 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 μm filter, thereby obtaining a final specimen.

Example 1-2

Large Scale Culture and Purification of Bacteriophage

Bacteriophage obtained in Example 1-1 was cultured at large scale using enterotoxigenic *Escherichia coli* (2618), and then the bacteriophage was purified therefrom.

Specifically, enterotoxigenic *Escherichia coli* (2618) was shaking cultured, and inoculated at $1.0\times10^{10}$ cfu, followed by centrifuging at 4,000 rpm for 10 minutes and re-suspending in 4 ml of SM solution. To this solution, the bacteriophage was added at $1.0\times10^{7}$ pfu with multiplicity of infection (MOI) of 0.001, and then left at room temperature for 20 minutes. 150 ml of LB medium was inoculated therewith, and cultured at 30° C. for 5 hours.

After completion of cultivation, chloroform was added to a volume of 1% (v/v) of the final volume, followed by stirring for 20 minutes, to which DNase I and RNase A as restriction enzymes were added in a final concentration of 1 μg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 1 ml of chloroform was added thereto with stirring, followed by centrifugation at 4° C. with 4,000 rpm for 20 minutes, thereby obtaining a supernatant. The supernatant was filtered through a 0.45 μm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill enterotoxigenic *Escherichia coli* from samples collected from pig feces, which was designated as "Bacteriophage ΦCJ28" and deposited at the Korean Culture Center of Microorganisms (KCCM) (361-221 Hongje 1-dong, Seodaemun-gu, Seoul, Korea) on Oct. 25, 2013 under accession number KCCM 11466P.

Example 2

Morphology Examination of ΦCJ28

The bacteriophage ΦCJ28 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water. The carbon film was mounted on a copper grid, and stained with 2% uranyl acetate for 60 seconds, dried, and examined under a transmission electron microscope (JEM-1011, 80 kV, magnification of ×200,000) (FIG. 1).

FIG. 1 is a transmission electron microscope image of bacteriophage ΦCJ28, in which the bacteriophage ΦCJ28 had morphological characteristics of an icosahedral capsid with a contractile tail, indicating that the bacteriophage belongs to family Myoviridae.

Example 3

Total Genomic DNA Size Analysis of ΦCJ28

Genomic DNA was extracted from the bacteriophage ΦCJ28 purified in Example 1.

Specifically, to a cultured solution of the purified bacteriophage ΦCJ28, 20 mM ethylenediaminetetraacetic acid (EDTA), 50 μg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol:chloroform=1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 10% (v/v) of 3M sodium acetate based on the total volume, followed by the addition of 2 volumes of 95% cold ethanol, mixing, and standing at −20° C. for 1 hour. The resulting substance was centrifuged at 0° C. and 12,000 rpm for 10 minutes, from which a supernatant was removed to obtain a precipitate, which was dissolved in 50 μl of TE buffered solution (Tris-EDTA, pH 8.0). The extracted DNA was diluted 10 fold, and then concentration of DNA was determined by measuring absorbance at $OD_{260}$.

Next, 1 μg of DNA was loaded on a 1% PFGE (pulsed field gel electrophoresis) agarose gel, and developed using BIORAD PFGE SYSTEM NO. 7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ28, and it could be seen that the genomic DNA size of the bacteriophage ΦCJ28 was 98 kb or more. In FIG. 2, M corresponds to DNA ladder as a standard for size measurement.

Example 4

Protein Pattern Analysis of ΦCJ28

15 μl of purified bacteriophage ΦCJ28 solution ($10^{10}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ28, and it could be seen that main proteins had a size of about 67.9 kDa, about 50.8 kDa and about 6 kDa.

Example 5

Analysis of Genetic Properties of ΦCJ28

In order to determine genetic properties of the bacteriophage ΦCJ28 purified in Example 1, DNA of the bacteriophage ΦCJ28 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterPro Scan.

Nucleotide sequence of the bacteriophage ΦCJ28 showed similarity to nucleotide sequence of previously reported bacteriophage (Enterobacteria phage Bp7), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ28 and decoded nucleotide sequence of the prior reported bacteriophage in the art.

TABLE 1

| Query | | | | Subject Description | E-Value | Identities Match/Total | Pct. (%) |
|---|---|---|---|---|---|---|---|
| Name | Length | Start | End | | | | |
| SEQ ID NO: 1 | 171499 | 94429 | 108404 | Enterobacteria phage Bp7, complete Genome | 0 | 13319/14021 | 94 |

DNA of the prepared bacteriophage ΦCJ28 was analyzed using a DNA sequencer and total nucleotide sequence is set forth in SEQ ID NO: 1.

Example 6 pH Stability of ΦCJ28

In order to identify whether the bacteriophage ΦCJ28 can maintain stability at low pH like stomach conditions, stability of the bacteriophage ΦCJ28 was examined at various pH (pH 2.0, 3.0, 4.0, 5.0).

For the experiment, various pH solutions (sodium acetate buffer solutions (pH 4.0 and pH 5.0) and sodium citrate buffer solutions (pH 2.0 and pH 3.0)) were prepared at a concentration of 2M.

180 μl of each pH solution was mixed with 20 μl of a bacteriophage solution with $2.9\times10^9$ PFU/ml titer to allow each pH solution to have a concentration of 1M, and then the resulting solution was left at room temperature for 2 hours. For a control group, 20 μl of a bacteriophage solution with $2.9\times10^9$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

FIG. 4 shows experimental results of acid resistance of the bacteriophage ΦCJ28. In FIG. 4, it could be seen that the bacteriophage ΦCJ28 did not lose its activity and maintained stability from pH 3.0 to pH 5.0, as compared with the control group.

Example 7

Heat Stability of Bacteriophage ΦCJ28

If bacteriophages are formulated into additives for feeds among dosage forms of bacteriophages, heat can be generated during formulation procedures, and thus, the following experiment was performed in order to determine heat stability of bacteriophages.

Specifically, 200 μl of bacteriophage ΦCJ28 solution with $2.9\times10^8$ PFU/ml was left at 60° C. for 0 minute, 30 minutes, 60 minutes and 120 minutes, respectively. Thereafter, the resulting experimental culture solution was serially diluted, and 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ28. As shown in FIG. 5, it could be seen that bacteriophage ΦCJ28 showed activity loss of about 1 log or less until bacteriophage ΦCJ28 was exposed to 60° C. for 30 minutes and activity loss of 3 log or more when bacteriophage ΦCJ28 was exposed for 60 minutes or more.

Example 8

Examination of Infection Range of Bacteriophage ΦCJ28 on a Wild-Type Isolated Strain, Enterotoxigenic *Escherichia coli*

Lytic activity of bacteriophage ΦCJ28 was tested for 99 strains of the wild-type enterotoxigenic *Escherichia coli* isolated by College of Veterinary Medicine, Seoul National University (SNU), College of Veterinary Medicine, Konkuk University and Korea Animal and Plant Quarantine Agency (KAPQA), in addition to enterotoxigenic *Escherichia coli* (2618) used in the present experiment. The isolated strains consist of 37 strains of F-serotype F4 type, 30 strains of F5 type, 7 strains of F6 type, 20 strains of F18 type and 5 strains of other type.

Specifically, 150 μl of a shaking culture solution of each strain ($OD_{600}$=2) was mixed, and 10 μl of bacteriophage ΦCJ28 solution with $10^9$ pfu/ml titer was dropped thereto and cultured by the soft agar overlay method at 30° C. for 18 hours, and then plaque formation was examined.

The results are shown in Table 2.

TABLE 2

| No. | Type | Strains | ΦCJ28 | No. | Type | Host cell | ΦCJ28 |
|---|---|---|---|---|---|---|---|
| 1 | F4 | 345 | | 51 | F5 | UK21 | |
| 2 | | 105 | 0 | 52 | | UK23 | |
| 3 | | 122 | 0 | 53 | | UK24 | |
| 4 | | 0149 | | 54 | | UK25 | |
| 5 | | JG280 | | 55 | | UK26 | |
| 6 | | F4 | 0 | 56 | | 1-1 | |
| 7 | | 162 | 0 | 57 | | 6-1 | |
| 8 | | 160 | 0 | 58 | | 9 | |
| 9 | | 107 | | 59 | | 10 | 0 |
| 10 | | R08 | | 60 | | 14 | 0 |
| 11 | | 193 | | 61 | | 16 | 0 |
| 12 | | 271 | | 62 | | 17 | 0 |
| 13 | | 3220 | 0 | 63 | | 30 | |
| 14 | | UK1 | | 64 | | 31 | |
| 15 | | UK3 | | 65 | | 34 | 0 |
| 16 | | UK4 | | 66 | | 35 | 0 |
| 17 | | UK7 | 0 | 67 | | 21 | |
| 18 | | UK8 | | 68 | F6 | 23 | |
| 19 | | UK9 | 0 | 69 | | F6 | 0 |
| 20 | | UK11 | | 70 | | 626 | 0 |
| 21 | | UK14 | | 71 | | P87 (SNU) | 0 |
| 22 | | UK15 | | 72 | | S127 | |
| 23 | | UK16 | | 73 | | 132 | |
| 24 | | UK17 | | 74 | | 133 | |
| 25 | | UK18 | | 75 | F18 | 135 | 0 |
| 26 | | UK19 | | 76 | | UK5 | |
| 27 | | UK20 | | 77 | | UK6 | |
| 28 | | 0105 | | 78 | | UK10 | |
| 29 | | UK24 | | 79 | | UK12 | 0 |
| 30 | | UK25 | | 80 | | UK13 | 0 |
| 31 | | UK26 | | 81 | | UK22 | |
| 32 | | UK29 | | 82 | | UK27 | |
| 33 | | UK30 | | 83 | | E2-4 | |
| 34 | | UK31 | | 84 | | 5 | 0 |
| 35 | | 66-1 | | 85 | | 8 | 0 |
| 36 | | K43 (KAPQA) | | 86 | | 11 | 0 |
| 37 | | K45 (KAPQA) | | 87 | | 12 | 0 |
| 38 | F5 | 2618 | 0 | 88 | | 23 | 0 |
| 39 | | 2617 | | 89 | | 24 | 0 |
| 40 | | 1 | 0 | 90 | | 25 | 0 |
| 41 | | 2 | 0 | 91 | | 28 | 0 |
| 42 | | 3 | 0 | 92 | | 31 | 0 |
| 43 | | 4 | 0 | 93 | | 35 | 0 |
| 44 | | 5 | 0 | 94 | | 42 | 0 |
| 45 | | 6 | | 95 | | 49 | 0 |
| 46 | | F5041 | | 96 | Other | UK32 | |
| 47 | | 645 | | 97 | | UK33 | |
| 48 | | K99 (KAPQA) | | 98 | | UK34 | |
| 49 | | S192 (SNU) | | 99 | | UK35 | 0 |
| 50 | | UK2 | 0 | 100 | | UK36 | |

As shown in table 2, the bacteriophage ΦCJ28 exhibits infection ability to F-serotype F4, F5, F6, F18 types, which are major causative bacteria of pig diarrhea in general pig farms, and thus is anticipated to exhibit excellent efficacy.

The invention claimed is:

1. A method for treating colibacillosis caused by enterotoxigenic *Escherichia coli*, comprising:

administering an effective amount of the bacteriophage ΦCJ28 deposited as accession number KCCM11466P to a pig.

2. A method for treating colibacillosis caused by enterotoxigenic *Escherichia coli*, comprising:

administering an effective amount of a composition comprising the bacteriophage ΦCJ28 deposited as accession number KCCM11466P to a pig.

* * * * *